(12) United States Patent
Mead et al.

(10) Patent No.: US 6,709,861 B2
(45) Date of Patent: Mar. 23, 2004

(54) CLONING VECTORS AND VECTOR COMPONENTS

(75) Inventors: David Alan Mead, Middleton, WI (US); Ronald Godiska, Verona, WI (US)

(73) Assignee: Lucigen Corp., Middleton, WI (US)

( * ) Notice: Subject to any disclaimer, the term of this patent is extended or adjusted under 35 U.S.C. 154(b) by 0 days.

(21) Appl. No.: 10/001,052

(22) Filed: Nov. 15, 2001

(65) Prior Publication Data

US 2004/0038401 A1 Feb. 26, 2004

Related U.S. Application Data

(60) Provisional application No. 60/249,594, filed on Nov. 17, 2000.

(51) Int. Cl.[7] .......................... C12N 15/63; C07H 21/04
(52) U.S. Cl. .................................... 435/320.1; 536/23.1
(58) Field of Search ....................... 435/320.1; 536/23.1

(56) References Cited

FOREIGN PATENT DOCUMENTS

WO    WO 98/38298    9/1998

OTHER PUBLICATIONS

Bernard et al. (1994) Gene 148:71–74.*
Current Protocols in Molecular Biology Online (1999) Chapter 3. Example 3.16.1. John Wiley & Sons.*
Gil and Bouche (1991) Gene 105 17–22.*
Podbielski et al. (1996) Gene 177:137–147.*
Brosius (1984) Gene 27151–160.*
Brückner (1992) Gene 122:187–192.*
Fitzgerald et al., Nucleic Acids Res. 14:3753 [1992].
Sanger et al.., Proc Natl Acad Sci USA 74:5463 [1977].
Tabor and Richarson, Proc Natl Acad Sci U S A 92–6339 [1995].
Smith et al., Nature 321:674 [1986].
Prober et al., Science 238:336 [1987].
Church et al. (Science 240: 185 [1988].
Creasey et al., BioTechniques 11: 102 [1991].
Cherry et al., Genomics 20: 68 [1994].
Wiemann et al. Anal. Biochem. 224. 117 [1995].
Bolivar et al., Gene 2:95 [1977].
Slilaty et al., Gene 213:83 [1998].
Henrich & Plapp, Gene 42, 345 [1986].
Bernhard et al., Gene, 148: 71 [1994].
Egholm et al., Nature 365: 566 [1993]).
Chang AC and Cohen SN, J. Bacteriol. 134: 1141–1156, 1978.
Rose RE, Nucleic Acids Res. 16: 355, 1988.
Vieira J and Messing J. Gene 19: 259–268, 1982.
Quandt J and Hynes MF, Gene 127:15–21, 1993).
Hoffmann–Berling H, Virology 22: 305, 1964.
Geider K et al.,Gene 33: 341–349, 1985.
Reynolds et al., J. Mol. Biol., 224:31 [1992].
Liu and Schwartz, Biotechniques 12:28–30, 1992.
Schmitt et al., J Bacteriol., 173:1536–43, 1991.
Weimann et al., Anal. Biochem. 234: 166 [1996].
Lipman et al., PNAS, USA, 86:4412, 1989.
Chen et al., Gene 55:179–187 (1987).
Dillard et al., J. Bacteriology, Aug. 173(16):5185–9 (1991).
Chen et al., Gene 64(1):155–64 (1988).
Padidam et al., Biotechniques 31:328–334 (2001).
Kholod et al., Biotechniques 31:322–328 (2001).

* cited by examiner

*Primary Examiner*—David Guzo
*Assistant Examiner*—Daniel Sullivan
(74) *Attorney, Agent, or Firm*—Medlen & Carroll, LLP

(57) ABSTRACT

The present invention relates to systems, methods, and compositions for cloning and sequencing insert nucleic acid sequences. In particular, the present invention provides vectors and vector components configured for multiplex cloning, multiplex sequencing, and fixed orientation cloning. The present invention also provides vectors and vector components that allow insert sequences that are deleterious to a host cell to be successfully cloned.

15 Claims, 16 Drawing Sheets

FIGURE 11 (SEQ ID NO:41)

```
TGATCGGCACGTAAGAGGTTCCAACTTTCACCATAATGAAATAAGATCACTACCGGGCGTATTTTTTGAGTTATCGAGAT
TTTCAGGAGCTAAGGAAGCTAAAATGGAGAAAAAAATCACTGGATATGCCACCGTTGATATATCCCAATGGCATCGTAAA
GAACATTTTGAGGCATTTCAGTCAGTTGCTCAATGTACCTATAACCAGACCGTTCAGCTGGATACTACGGCCTTTTTAAA
GACCGTAAAGAAAAATAAGCACAAGTTTTATCCGGCCTTTATTCACATTCTTGCCCGCCTGATGAATGCTCATCCGGAAT
TCCGTATGGCAGTGAAAGACGGTGAGCTGGTGATATGGGATAGTGTTCACCCTTGTTACACCGTTTTCCATGAGCAAACT
GAAACGTTTTCATCGCTCTGGAGTGAATACCACGACGATTTCCGGCAGTTTCTACACATATATTCGCAAGATGTGGCGTG
TTACGGTGAAAACCTGGCCTATTTCCCTAAAGGGTTTATTGAGAATATGTTTTTCGTCTCAGCCAATCCCTGGGTGAGTT
TCACCAGTTTTGATTTAAACGTGGCCAATATGGACAACTTCTTCGCCCCCGTTTTCACCATGGGCAAATATTATACGCAA
GGCGACAAGGTGCTGATGCCGCTGGCGATTCAGGTTCATCATGCCGTTTGTGATGGCTTCCATGTCGGCAGAATGCTTAA
TGAATTACAACAGTACTGCGATGAGTGGCAGGGCGGGGCGTAAATGCAAAGCTTGCATGCCTGCAGGTCGACTCTAGAGG
ACCGGGTACCGAGCTCAGATCTTAGCATGGGACGTTTATATAGTGGTAATCTGGCAGCATTCAAGGCAGCAACAAACAAG
CTGTTCCAGTTAGACTTAGCGGTCATTTATGATGACTGGTATAATGCCTATACAAGAAAAGATTGCATACGGTTACGTAT
TGAGGACAGATCTGGAAACCTGATTGATACTAGCACCTTCTACCACCACGACGAGGACGTTCTGTTCAATATGTGTACTG
ATTGGTTGAACCATATGTATGACCAGTTGAAGGACTGGAAGTAATAAGATCTTTGGTCCTGCAGGGAGCGTTAACATTTA
AATCGTTGCTGGCGTTTTTCCATAGGCTCCGCCCCCCTGACGAGCATCACAAAAATCGACGCTCAAGTCAGAGGTGGCGA
AACCCGACAGGACTATAAAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTGTAGGTATCTCAGTTCGG
TGTAGGTCGTTCGCTCCAAGCTGGGCTGTGTGCACGAACCCCCGTTCAGCCCGACCGCTGCGCCTTATCCGGTAACTAT
CGTCTTGAGTCCAACCCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGAACAGTATTTGGTATCTGCGCTC
TGCTGAAGCCAGTTACCTTCGGAAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAGGATCGTTTGATCTTTTGGGCCC
```

FIGURE 12
A.
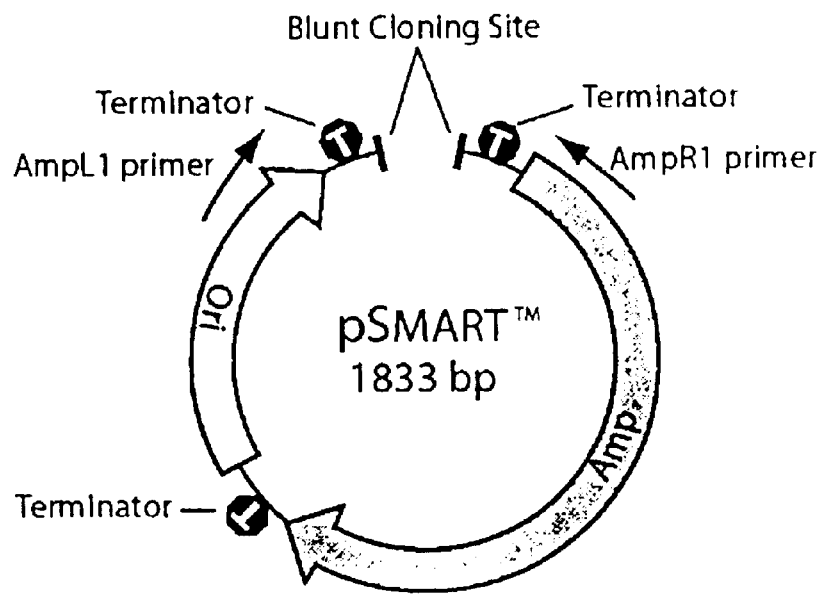
B.
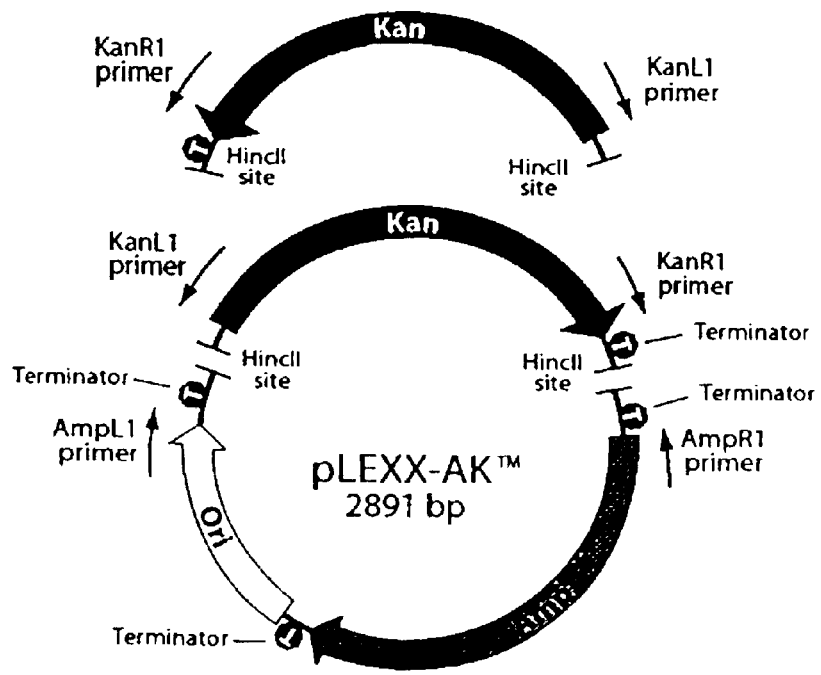

FIGURE 14

A. SEQ ID NO:85

```
GACGAATTCTCTAGATATCGCTCAATACTGACCATTTAAATCATACCTGA
CCTCCATAGCAGAAAGTCAAAAGCCTCCGACCGGAGGCTTTTGACTTGAT
CGGCACGTAAGAGGTTCCAACTTTCACCATAATGAAATAAGATCACTACC
GGGCGTATTTTTTGAGTTATCGAGATTTTCAGGAGCTAAGGAAGCTAAAA
TGAGTATTCAACATTTCCGTGTCGCCCTTATTCCCTTTTTTGCGGCATTT
TGCCTTCCTGTTTTTGCTCACCCAGAAACGCTGGTGAAAGTAAAAGATGC
TGAAGATCAGTTGGGTGCACGAGTGGGTTACATCGAACTGGATCTCAACA
GCGGTAAGATCCTTGAGAGTTTACGCCCCGAAGAACGTTTTCCAATGATG
AGCACTTTTAAAGTTCTGCTATGTGGCGCGGTATTATCCCGTATTGACGC
CGGGCAAGAGCAACTCGGTCGCCGCATACACTATTCTCAGAATGACTTGG
TTGAGTACTCACCAGTCACAGAAAAGCATCTCACGGATGGCATGACAGTA
AGAGAATTATGCAGTGCTGCCATAACCATGAGTGATAACACTGCGGCCAA
CTTACTTCTGGCAACGATCGGAGGACCGAAGGAGCTAACCGCTTTTTTGC
ACAACATGGGGGATCATGTAACTCGCCTTGATCGTTGGGAACCGGAGCTG
AATGAAGCCATACCAAACGACGAGCGTGACACCACGATGCCTGTAGCAAT
GGCAACAACGTTGCGCAAACTATTAACTGGCGAACTACTTACTCTAGCTT
CCCGGCAACAATTAATAGACTGGATGGAGGCGGATAAAGTTGCAGGATCA
CTTCTGCGCTCGGCCCTCCCGGCTGGCTGGTTTATTGCTGATAAATCTGG
AGCCGGTGAGCGTGGGTCTCGCGGTATCATTGCAGCACTGGGGCCAGATG
GTAAGCCCTCCCGCATCGTAGTTATCTACACGACGGGGAGTCAGGCAACT
ATGGATGAACGAAATAGACAGATCGCTGAGATAGGTGCCTCACTGATTAA
GCATTGGTAATGAGGGCCCAAATGTAATCACCTGGCTCACCTTCGGGTGG
GCCTTTCTGCGTTGCTGGCGTTTTTCCATAGGCTCCGCCCCCTGACGAG
CATCACAAAAATCGATGCTCAAGTCAGAGGTGGCGAAACCCGACAGGACT
ATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGA
AGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGA
CACGACTTATCGCCACTGGCAGCAGCCACTGGTAACAGGATTAGCAGAGC
GAGGTATGTAGGCGGTGCTACAGAGTTCTTGAAGTGGTGGCCTAACTACG
GCTACACTAGAAGAACAGTATTTGGTATCTGCGCTCTGCTGAAGCCAGTT
ACCTCGGAAAAGAGTTGGTAGCTCTTGATCCGGCAAACAAACCACCGCT
GGTAGCGGTGGTTTTTTTGTTTGCAAGCAGCAGATTACGCGCAGAAAAAA
AGGATCTCAAGAAGATCCTTTGATTTTCTACCGAAGAAAGGCCCACCCGT
GAAGGTGAGCCAGTGAGTTGATTGCAGTCCAGTTACGCTGGAGTCTGAGG
CTCGTCCTGAATGATATCAAGCTTGAATTCGTT
```

B. SEQ ID NO: 86

```
GACGCATATCTGGATCCTGCAGCCGATACGGTCGTCGTCCGTTTAAACGTTGTGTCTCAAAATCTCTGATG
TCACGTTGCACAAGATAAAAATATATCATCATGAACAATAAAACCGTCTGCTTACATAAACAGTAATACAA
GGGGTGTTATGAGCCATATTCAACGGGAAACGTCTTGCTCGAGGCCGCGATTAAATTCCAACATGGATGCT
GATTTATATGGGTATAAATGGGCTCGCGATAATGTCGGGCAATCAGGTGCGACAATCTATCGATTGTATGG
GAAGCCCGATGCGCCAGAGTTGTTTCTGAAACATGGCAAAGGTAGCGTTGCCAATGATGTTACAGATGAGA
TGGTCAGGCTAAACTGGCTGACGGAATTTATGCCTCTTCCGACCATCAAGCATTTTATCCGTACTCCTGAT
GATGCATGGTTACTCACCACTGCGATCCCAGGGAAAACAGCATTCCAGGTATTAGAAGAATATCCTGATTC
AGGTGAAAATATTGTTGATGCGCTGGCAGTGTTCCTGCGCCGGTTGCATTCGATTCCTGTTTGTAATTGTC
CTTTTAACGGCGATCGCGTATTTCGTCTCGCTCAGGCGCAATCACGAATGAATAACGGTTTGGTTGGTGCG
AGTGATTTTGATGACGAGCGTAATGGCTGGCCTGTTGAACAAGTCTGGAAAGAAATGCATAAGCTTTTGCC
ATTCTCACCGGATTCAGTCGTCACTCATGGTGATTTCTCACTTGATAACCTTATTTTTGACGAGGGGAAAT
TAATAGGTTGTATTGATGTTGGACGAGTCGGAATCGCAGACCGATACCAGGATCTTGCCATCCTATGGAAC
TGCCTCGGTGAGTTTTCTCCTTCATTACAGAAACGGCTTTTTCAAAAATATGGTATTGATAATCCTGATAT
GAATAAATTGCAGTTTCACTTGATGCTCGATGAGTTTTTCTAATCAAATAAAACGAAAGGCTCAGTCGAAA
GACTGAGCCTTTCGTTTTAATCTGGAAAAACCACCCTGGCGCTGCAGGTTCCAGATTCCTGGTT
```

CLONING VECTORS AND VECTOR COMPONENTS

The present Application claims priority to U.S. Provisional Application Serial No. 60/249,594 filed Nov. 17, 2000, hereby incorporated by reference in its entirety.

The present application was funded in part with government support under grant number Grant #HG01800-03 from the National Human Genomic Research Institute of the National Institute of Health. The government has certain rights in this invention.

FIELD OF THE INVENTION

The present invention relates to systems, methods, and compositions for cloning and sequencing insert nucleic acid sequences. In particular, the present invention provides vectors and vector components configured for multiplex cloning, multiplex sequencing, and fixed orientation cloning. The present invention also provides vectors and vector components that allow insert sequences that are deleterious to a host cell to be successfully cloned.

BACKGROUND OF THE INVENTION

Prior to the 1990's, DNA sequencing was a time consuming, labor intensive, manual protocol by which individual researchers read 100's of bases per day from a single DNA template. It has since evolved into an automated, robotic process by which major genome sequencing centers read tens of millions of bases from tens of thousands of DNA templates per day. This vast increase in sequencing capacity has broadened the scope of DNA sequencing to entire genomes rather than individual genes. It has likewise created a need to increase the rate of throughput in all stages of the sequencing process.

The most prominent example of large scale sequencing to date is the Human Genome Initiative, an effort to sequence all 3.3 billion bases of the human genome. Begun in 1990, the Human Genome Initiative was declared "finished" on Jun. 26, 2000, by the major genome centers involved. The public draft genome released by the National Institutes of Health consortia was 85% assembled, with 97% of the genome covered by clones whose location is known. This project required reading some 25 million DNA sequences. In a completely independent effort, Celera Corporation claimed to have 99% of the genome sequence assembled at a 3x redundancy level, which required 27 million DNA sequencing reads.

The public effort for "complete and accurate" sequencing, typically defined as 5x coverage and an accuracy of not more than 1 mistake every 10,000 bases, will require sequencing millions of additional plasmid clones over several more years to obtain high quality data on the entire genome. Because so much of the human genome is not characterized, a more complete understanding of it will be facilitated by sequencing the genomes of other organisms for comparison, such as the mouse, rat, dog, and chimpanzee. In fact, Celera claims to have sequenced three mouse genomes during the year 2000, while the NIH consortia of university and international genome centers have begun work on the mouse and rat genome. The NIH has also initiated funding of pilot sequencing projects for the chicken, puffer fish, and zebra fish.

At the 12th International Genome Sequencing and Analysis Conference in Miami, Fla. (Sep. 12–15, 2000), Celera presented data showing that over 200,000 plasmid template purifications a day are required to sustain their ongoing sequencing efforts. The NIH consortia purify a similar number of templates on a daily basis. Genome sequencing facilities at other large corporations, overseas national genome projects, and smaller academic labs sequence an additional 500,000 plasmid templates per day. Thus, the worldwide rate of sequencing is rapidly approaching 1,000,000 templates per day.

The generation of clone banks, or libraries, of DNA is an important intermediate step in sequence analysis of whole genomes. In a process called shotgun cloning and sequencing, large molecules of DNA, often more than 100,000 bases (100 kb) in length, are fragmented and reduced to libraries of numerous sub-clones of approximately 1–4 kb for propagation and sequence analysis. Most large-scale DNA sequencing strategies depend on a multi-step process to randomly fragment the target molecule into these smaller pieces, which are then enzymatically joined (ligated) into a cloning vector in a reaction that inserts one or more DNA fragments into a single site in each vector molecule (Fitzgerald et al., Nucleic Acids Res. 14:3753 [1992]). This ligation mixture is introduced into specific strains of *Eschericia coli* (*E. coli*), with each bacterial cell propagating one vector along with any DNA fragments it carries. The vector DNA, which may or may not contain an insert, is purified from each cell line and used as a template in an enzymatic sequencing reaction (Sanger et al., Proc Natl Acad Sci USA 74:5463 [1977]; Prober et al., Science 238:336 [1987]; Tabor and Richarson, Proc Natl Acad Sci U S A 92:6339 [1995], all of which are hereby incorporated by reference). The reaction product is analyzed by automated sequencing instruments to determine the linear sequence of the sub-cloned DNA fragments (Smith et al., Nature 321:674 [1986], hereby incorporated by reference). Computer algorithms are used to assemble the data from the library of sub-fragments, typically producing sequence information for 80–95% of the original DNA molecule. "Gap filling" techniques are used to determine the remaining 5–20% of the target DNA.

Although most DNA sequencing methods utilize one template or primer per sequencing reaction, there are exceptions to this pattern. In early examples, Church et al. (Science 240: 185 [1988]) and Creasey et al. (BioTechniques 11: 102 [1991]) performed multiple Sanger dideoxy sequencing reactions in a single set of four tubes, using vectors containing unique sequence tags. The reactions from each set of tubes were run on a sequencing gel and transferred to a nylon membrane. Each sequence reaction was then detected by sequentially probing the membrane with an oligonucleotide specific for the tag on each vector. Other variations on this theme have also been developed (Cherry et al., Genomics 20: 68 [1994]).

Subsequently, Wiemann et al. (Anal. Biochem. 224: 117 [1995]; Anal. Biochem. 234: 166 [1996]) showed that fluorescently labeled sequencing primers could be used to simultaneously sequence both strands of a dsDNA template. Recent examples have demonstrated multiplex co-sequencing using the four-color dye terminator reaction chemistry pioneered by Prober et al. (Science 238: 336 [1987]). At the 10th International Genome Sequencing and Analysis Conference, (Sep. 17–20, 1998, Miami Beach, Fla.), Uhlen (Royal Institute of Technology) and Chiesa (PE Biosystems) independently showed that biotinylated oligomers could be used to specifically capture an individual sequencing reaction from a pool of multiple reactions in a single tube.

Numerous vectors are available for cloning DNA into *E. coli*. Conventional plasmid vectors are normally double stranded circular DNA molecules containing restriction enzyme recognition sites suitable for inserting exogenous DNA sequences, an antibiotic selectable gene, an origin of replication for autonomous propagation in the host cell, and a gene for the discrimination or selection of clones that contain recombinant insert DNA.

One of the first recombinant DNA cloning systems used a dual antibiotic resistant plasmid such as pBR322 (Bolivar et al., Gene 2:95 [1977]). One of the resistance genes served to select for those cells taking up plasmid DNA. This gene was typically the beta-lactamase gene (Amp or ampR), which confers resistance to ampicillin (amp). The other resistance gene, Tet or tetR, encoding resistance to tetracycline (tet), was used indirectly as the indicator for recombinant clones. The foreign DNA fragment was inserted into any of a number of restriction sites within the Tet gene, resulting in inactivation of the Tet gene and sensitivity of the transformed cell to killing by tetracycline.

Thus, to find those clones that might have contained foreign insert DNA, the transformed cells were first spread onto ampicillin-containing plates. Those colonies that grew were replica plated onto tetracycline-containing plates. The colonies growing on the ampicillin but not on the tetracycline plates were likely candidates for further analysis. This screening method required additional labor and time compared to newer methods and is rarely used now.

The predominant cloning system in use for the last two decades is the "blue screen" method. Blue screen vectors contain a selectable marker such as the ampicillin resistance gene described above. However, the tetracycline screen is replaced by a color discrimination technique based on insertional inactivation of a genetically engineered gene that encodes beta galactosidase (βGal). The bacteriophage M13mp series and plasmid pUC series of cloning vehicles are ubiquitous examples of this screening method. These vectors encode the N-terminal 60 amino acids of the βGal gene, the so-called lacZα peptide, which is inactive as such. Another inactive, truncated portion of lacZ (the lacZΔM15 allele) is carried on an F' episome of the host bacteria, which can complement the lacZα peptide to restore βGal activity. Cells containing non-recombinant vectors therefore produce functional βGal, which can hydrolyze the indicator chemical XGAL (5-bromo-4-chloro-3-indolyl-beta-galactoside) to produce a blue colored product.

The lacZα fragment in the vector also contains a series of cloning sites, termed the multiple cloning site, situated such that insertion of foreign DNA into any one site disrupts the lacZα peptide. An insertion into a site generally, but not always, inactivates the lacZα fragment. Thus, cells containing an insert in the vector generally do not produce active βGal. These recombinant clones therefore remain white.

The advantage of the blue screen is that it is a visual assay to discriminate recombinant clones from non-recombinants. However, there are a number of disadvantages to this cloning strategy. One disadvantage is that the substrate XGAL is expensive, unstable, and awkward to use. Another chemical compound, IPTG (isopropyl-β-D-thiogalactoside), a gratuitous inducer of the lac promoter that drives lacZα in these vectors, is also often required for this cloning system. Another disadvantage is that the high percentage of non-recombinant (blue) colonies compete for nutrients and space with the desired recombinant colonies. A need exists for cloning systems that eliminate the requirement of exogenous chemical additives for screening.

A more significant problem with blue screen cloning technology is the issue of false negative and false positive results, as well as results that cannot be easily classified (Slilaty et al., Gene 213:83 [1998]). False positive results are colonies or plaques that appear white or uncolored, yet do not contain a foreign DNA insert in the lacZα cloning vectors. Among the external factors responsible for generating false positives are: (1) contamination of the restriction or modifying enzymes used to process the vector (e.g., exonucleases that remove bases from the termini of the lacZα fragment, creating frame-shifts that inactivate the fragment), (2) spontaneous mutations in the lacZα fragment or in the lacZΔM15 allele, and (3) loss of the F' episome carrying the lacZΔM15 allele. False positive results are carried forward and analyzed as real positive clones, eventually being detected as empty, deleted, or otherwise mutated vector DNA when further analyzed.

False negative results are blue colonies or plaques that actually do contain foreign DNA inserted in the lacZα based vector. There are two principle causes of false negative results using blue screen vectors: (1) in-frame insertion of DNA fragments containing one or more open reading frames, and (2) reinitiation of translation within the mRNA transcribed from the inserted DNA fragment. Either event results in the synthesis of the lacZ α-peptide fused to a foreign peptide, which often does not impair its activity. Because the fusion peptide restores βGal activity, these clones produce the blue color and are erroneously discarded as non-recombinants.

Another problem is the hypersensitivity of the XGAL assay system. Because very little beta-galactosidase activity is required to produce a color reaction, inserts in blue screen vectors often result in "light blue" and "dark white" colony phenotypes that complicate the interpretation of cloning results. These blue false negatives are rarely carried forward for analysis and can lead to erroneous conclusions that the DNA fragments they carry are "non-clonable." This bias against certain sequences malt lead to excessive gaps in shotgun DNA sequencing results as well. Thus, a need exists for cloning systems that do not rely on the blue screen technology.

A cloning procedure that selectively eliminates the background of parental non-recombinant vector would be advantageous in any DNA library construction or sub-cloning experiment. It would also eliminate the screening process, as well as the need to buy, weigh, and mix the required screening chemicals. Various cloning vectors permitting direct selection of recombinant clones have been described in the scientific literature.

Most positive selection vectors (or "suicide" vectors) are based on the insertional inactivation of a lethal gene product (Henrich & Plapp, Gene 42, 345 [1986]). Insertion of a foreign DNA fragment disrupts the lethal gene, allowing recombinant cells to grow. Bacterial clones that carry a parental vector do not survive, resulting in selection for clones that carry foreign DNA fragments. The use of suicide vectors for positive selection is an efficient strategy to suppress an undesired background of non-recombinant clones that do not carry the desired DNA insert.

Other examples of positive selection are based on abolition of a particular sensitivity towards metabolites, selection by means of DNA-degrading or RNA-degrading enzymes, or selection by means of unstable long palindromic DNA sequences. Several problems can arise when using the available direct selection cloning vectors. One problem is a high number of false positive clones, i.e., viable clones without an insert. False positives may arise from mutations in the selection genes or their controlling genetic elements (so called revertants), or by inadequate expression of the toxic gene using an inducible genetic system (Bernhard et al., Gene, 148: 71 [1994]). False positive clones are typically carried forward as real positives and are only detected as false positives after analysis of their sequence. Thus, a need exists for a positive selection cloning system that minimizes the number of false positive clones.

Another problem with available direct selection vectors is a high number of false negative clones, i.e., clones with inserts that do not grow or grow very slowly. Similar to the situation described above for blue screen method, certain DNA fragments may not completely inactivate the function of the toxic gene product, which can result in a functionally diminished but nevertheless toxic protein. In other cases, insertion of a particular DNA fragment may not in any way adversely affect the lethal properties of the selection gene. Thus, no clones with the desired insert are obtained. This may occur in particular with small DNA fragments or/and those fragments whose nucleotide sequence is in frame with the selection gene. False negative clones are rarely detected, because they cannot grow on the plating media. Thus, a need exists for a direct selection cloning system that minimizes the number of false negative clones.

Yet another disadvantage of direct selection vectors is that, as in the blue screen vectors, the vector contains a promoter that actively transcribes the region into which the insert DNA is to be cloned. Therefore, insert DNA that encodes toxic or deleterious peptides or proteins will be harmful to the bacterial host cell in which it is carried. Thus, a need exists for a low-background vector that does not transcribe the inserted DNA fragment.

A further disadvantage in some positive selection schemes is the need to make up complex nutrient media to utilize the selection mechanism. Thus, a need exists for direct selection cloning systems that do not require the use of exogenous chemical compounds.

Despite the rapid evolution of sequencing, it is nonetheless still constrained by the significant effort needed to generate libraries of DNA templates, identify recombinant clones, and purify the DNA from those clones. The process of constructing a random clone library is technically challenging, inefficient, and involves numerous steps. The present paradigm for shotgun cloning requires one cloning reaction to generate a library of several thousand templates, each template containing 1 or 2 primer extension sites, which are anchor sequences for the enzymatic method of dideoxy sequencing typically used today. Once a library is made, a vast number of DNA templates must be grown, purified, and sequenced to deduce the sequence of a large genome. For the human genome project, two approaches were used to determine this genetic blueprint. One method was the whole genome shotgun cloning approach used by Celera Corporation. A few shotgun libraries were constructed, but tens of millions of random clones were sequenced using this approach. The other approach, used by the NIH consortia, was to create an ordered array of cosmid, BAC and P1 clone libraries, with average clone sizes of 40–100 kb. An arrayed library covering the entire genome requires approximately 100,000 cosmid clones or 40,000 BAC or P1 clones, assuming a 20% clone overlap. Thus, a minimum of 40,000 to 100,000 shotgun libraries are required to sequence the human genome with this approach. Assuming 400 templates are needed to sequence a 40 kb cosmid clone, or 1000 templates per 100 kb BAC or P1 clone, approximately 40 million templates will be grown, purified, and sequenced. An alternative strategy using large insert BAC clones (150 kb average inserts) and minimal overlap predicts that 20,000 BAC clones will be sufficient to sequence the genome. If 1500 templates are needed to sequence each of these large insert BAC clones, then a minimum of 30 million templates will be grown, purified, and sequenced. Additional genome projects and failed reactions can be expected to double or triple the number of libraries, as well as templates, required for this undertaking. Such high-throughput demands of large-scale sequencing necessitate improvements that will minimize rate-limiting steps. The growth, purification, and sequencing of tens of millions of templates are significant rate-limiting steps in the sequencing of any large genome. What is needed are methods, compositions and systems for cloning and sequencing insert DNA sequences that are faster, more economical, produce very low levels of non-recombinant vector background, and exhibit less discrimination against fragments containing promoter-like sequences or open reading frames.

SUMMARY OF THE INVENTION

The present invention relates to systems, methods, and compositions for cloning and sequencing insert nucleic acid sequences. In particular, the present invention provides vectors and vector components configured for multiplex cloning and multiplex sequencing. The present invention also provides vectors and vector components configured to reduce or minimize transcription into and out of insert sequences.

In some embodiments, a circular vector (e.g. recombinant plasmid) is formed from at least two vector components containing selectable marker sequences. In particular embodiments, this vector (e.g. recombinant plasmid) is formed from at least two vector components containing selectable marker sequences and at least two insert DNA sequences. The formation of a vector (e.g. recombinant plasmid) may occur, for example, in a single ligation reaction (e.g. the two vector components and insert sequences, all separate, are joined together in a single ligation reaction). In some embodiments, the compositions of the present invention permit multiplex sequencing (e.g. from a single vector constructed from at least two vector components and at least two insert sequences). In preferred embodiments, the source nucleic acid used to form the vectors of the present invention are at least two separate source nucleic acid molecules (e.g. neither of which has all of the selectable markers contained in the final vector that is formed).

In some embodiments, the present invention provides systems, kits, and compositions for cloning nucleic acid comprising at least two separate source nucleic acid molecules capable of supplying X+1 vector components, wherein the vector components are configured for combining in the presence of X+1 insert sequences to form a closed circular recombinant vector (e.g. recombinant plasmid). In certain embodiments, the present invention provides systems, kits, and compositions for cloning nucleic acid comprising at least two different source nucleic acid molecules capable of supplying X+1 vector components, wherein the vector components are configured for combining in the presence of X−1 insert sequences to form a closed circular recombinant vector (e.g. recombinant plasmid). In particular embodiments, the present invention provides systems, kits, and compositions for cloning nucleic acid comprising at least two separate source nucleic acid molecules capable of supplying X+1 vector components, wherein the X+1 vector components are configured for combining in the presence of X+1 insert sequences to form a circular vector (e.g. recombinant plasmid).

In some embodiments, the present invention provides systems, kits, and compositions for cloning nucleic acid comprising at least two separate source nucleic acid molecules capable of supplying X+1 vector components, wherein the X+1 vector components are configured for combining in the presence of X−1 insert sequences to form a circular vector (e.g. recombinant plasmid), and wherein the vector components are non-contiguous within the circular vector. In some embodiments, X is a positive integer (e.g. 1–50). In particular embodiments, X is selected from 1, 2, 3, 4, 5, and 6.

In other embodiments, the present invention provides systems, kits, and compositions for cloning nucleic acid comprising at least two separate source nucleic acid molecules capable of supplying two vector components, wherein the vector components are configured for combining in the presence of two insert sequences to form a circular vector (e.g. recombinant plasmid), and wherein the vector components are non-contiguous with the circular vector. In some embodiments, the present invention provides systems, kits, and compositions for cloning nucleic acid comprising at least two separate source nucleic acid molecules capable of supplying three vector components, wherein the vector components are configured for combining in the presence of three insert sequences to form a circular vector (e.g. recombinant plasmid), and wherein the vector components are non-contiguous with the circular vector.

In some embodiments, the present invention provides systems, compositions, and kits, comprising at least two separate source nucleic acid molecules configured for supplying X+1 vector components, wherein the X+1 vector components are configured for combining in the presence of X+1 insert sequences to form a circular vector such that the X+1 vector components are non-contiguous within the circular vector. In certain embodiments, the systems, compositions, and kits further comprise the X+1 insert sequences.

In particular embodiments, the present invention provides systems, compositions, and kits comprising X+1 vector components, wherein each of the X+1 vector components are configured for combining in the presence of X+1 insert sequences to form a circular vector such that the X+1 vector components are non-contiguous within the circular vector. In certain embodiments, the systems, compositions, and kits further comprise the X+1 insert sequences.

In certain embodiments, the present invention provides compositions, kits, and systems for fixed orientation cloning. In certain embodiments, vector components with selectable marker sequences (e.g. all the same selectable marker sequences, or different selectable marker sequences) are utilized for fixed orientation cloning. In other embodiments, vector components without selectable marker sequences are utilized for fixed orientation cloning. In further embodiments, some vector components with selectable marker sequences and some vector components without selectable marker sequences are utilized for fixed orientation cloning. In some embodiments, the present invention provides kits, systems, and compositions for fixed orientation cloning comprising X+1 vector components, wherein each of the X+1 vector components comprises two different sticky free ends and are configured for combining in the presence of X+1 insert sequences to form a circular recombinant vector, wherein each of the X+1 insert sequences comprise two identical sticky free ends that are unique among the X+1 insert sequences. In preferred embodiments, each of the two different sticky free ends (of the vector components) binds one of the X+1 insert sequences. In other preferred embodiments, the X+1 vector components are non-contiguous within the circular recombinant vector.

In certain embodiments, each of the X+1 vector components comprises; i) first and second free ends, and ii) a selectable marker region comprising at least one selectable marker sequence unique among the X+1 vector components. In particular embodiments, each of the X+1 vector components further comprises; iii) a first transcriptional terminator between the first free end and the selectable marker region, and iv) a second transcriptional terminator between the second free end and the selectable marker region. In some embodiments, the first transcriptional terminator is configured to terminate RNA transcripts entering the selectable marker region from the first free end. In other embodiments, the second transcriptional terminator is configured to terminate RNA transcripts entering the selectable marker region from the second free end.

In some embodiments, each of the X+1 vector components comprises a non-promoter sequence between the first free end and the selectable marker region, wherein the non-promoter sequence is unable to serve as an operable promoter in a bacterial host cell. In preferred embodiments, the bacterial host cell is *Escherichia coli*. In other embodiments, each of the X+1 vector components comprises a non-promoter sequence between the second free end and the selectable marker region, wherein the non-promoter sequence is unable to serve as an operable promoter in a bacterial host cell. In preferred embodiments, the bacterial host cell is *Escherichia coli*. In certain embodiments, there is a selectable marker after the selectable marker region.

In certain embodiments, one of the X+1 vector components comprises SEQ ID NO:85 or a sequence that is at least 90% identical to SEQ ID NO:85 (e.g. at least 95% or at least 98% identical to SEQ ID NO:85). In some embodiments, one of the X+1 vector components comprises SEQ ID NO:86 or a sequence that is at least 90% identical to SEQ ID NO:86 (e.g. at least 95% or at least 98% identical to SEQ ID NO:86). In preferred embodiments, at least one of the X+1 insert sequence is a lethal or toxic sequence (e.g. will not allow the host cell to form a colony if the insert sequence is transcribed).

In some embodiments, the first and second free ends are configured such that they will not bind to each other. In certain embodiments, the first and second free ends comprise 5' ends lacking terminal phosphate groups. In other embodiments, the first and second free ends are blunt free ends or sticky free ends. In particular embodiments, at least one of the X+1 insert sequences is of unknown sequence. In preferred embodiments, each of the X+1 vector components comprises two primer binding sites (e.g. such that the circular vector formed has a pair of primer binding sites for sequencing each of the X+1 insert sequences). In certain embodiments, the circular vector is a low copy number circular vector (e.g. contains a gene causing a low copy number or an origin of replication causing a low copy number). In other embodiments, the low copy number circular vector is configured such than no more that 200 copies are produced in a host cell (e.g. no more than 100 or no more than 20 copies per host cell).

In some embodiments, the present invention provides fixed orientation cloning. In particular embodiments, each of the X+1 insert sequences comprise two identical sticky free ends that are unique among the X+1 insert sequences, wherein each of the X+1 vector components comprises two different sticky free ends, and wherein each of the two different sticky free ends binds one of the X+1 insert sequences.

In other embodiments, at least one of the X+1 vector components comprises an ampicillin resistance gene and an Origin of replication. In some embodiments, the ampicillin resistance sequence is a mutated ampicillin resistance sequence configured to reduce feeder colonies. In some embodiments, the mutated ampicillin resistance gene (e.g. derived from pUC19) comprises at least one mutation selected from: T to A at position 174; T to C at position 333; A to G at position 412, C to T at position 648; T to C at position 668; T to C at position 764; and combinations thereof. In preferred embodiments, the circular vector is a recombinant plasmid. In other embodiments, the promoter of the ampicillin resistance gene is replaced by a less active promoter (e.g. CamR promoter).

In certain embodiments, each of the source nucleic acid molecules is configured to supply no more than X of the X+1 vector components. In some embodiments, at least one of the source nucleic acid molecules comprises at least one of the X+1 vector components. In particular embodiments, at least one of the source nucleic acid molecules comprises a template for generating at least one of the X+1 vector components.

In some embodiments, the present invention provides kits comprising at least two separate source nucleic acid molecules configured for supplying X+1 vector components, and one other component (e.g., buffer, product insert, sequencing primers, ligase, etc.). In other embodiments, the present invention provides kits comprising X+1 vector components, wherein the X+1 vector components are configured for combining in the presence of X+1 insert sequences to form a circular vector such that the X+1 vector components are non-contiguous within the circular vector, and one other component (e.g., buffer, product insert, sequencing primers, ligase, etc.). In additional embodiments, the kits further comprise an insert DNA end repair kit (e.g. comprising a polymerase and kinase). In certain embodiments, the kits of the present invention further comprise a written insert component (e.g. comprising written instructions for using the kit).

In certain embodiments, the present invention provides compositions comprising a vector component, wherein the vector component comprises: i) first and second free ends; ii) a selectable marker region, iii) a first transcriptional terminator between the first free end and the selectable marker region, and iv) a second transcriptional terminator between the second free end and the selectable marker region, and wherein the vector component is configured to form a circular vector when combined with an insert sequence. In preferred embodiments, the insert sequence is a lethal or toxic insert sequence (e.g. will not allow the host cell to form a colony if the insert sequence is transcribed). In certain embodiments, the insert sequence has at least 65% A/T content (e.g. at least 65%, 75%, 80%, or 85% A/T content).

In some embodiments, the vector component comprises a non-promoter sequence between the first free end and the selectable marker region, wherein the non-promoter sequence is unable to serve as an operable promoter in a bacterial host cell. In preferred embodiments, the bacterial host cell is Escherichia coli.

In certain embodiments, the vector component comprises a non-promoter sequence between the second free end and the selectable marker region, wherein the non-promoter sequence is unable to serve as an operable promoter in a bacterial host cell. In preferred embodiments, the bacterial host cell is Escherichia coli. In some embodiments, the first and second free ends comprise 5' ends lacking terminal phosphate groups. In other embodiments, the first and second free ends are blunt free ends. In certain embodiments, the selectable marker region comprises first and second selectable marker sequences. In some embodiments, the selectable marker region further comprises a transcriptional terminator. In particular embodiments, the transcriptional terminator is between the first and second selectable marker sequences. In other embodiments, the first selectable marker sequence is an Origin of Replication. In certain embodiments, the second selectable marker sequence is an antibiotic resistance gene comprising a promoter sequence and a protein encoding sequence. In preferred embodiments, the promoter sequence is closer to the first or second free ends than the protein encoding sequence (e.g. transcription of the selectable marker sequence proceeds "away" from the free ends).

In certain embodiments, the present invention provides compositions comprising a circular vector, wherein said circular vector comprises: i) a cloning site comprising at least one unique restriction site for insertion of exogenous DNA; ii) a selectable marker region, iii) a transcriptional terminator following the selectable marker region, oriented so as to terminate any RNA transcript initiated from the selectable marker region; iv) a ["5'-end"] transcriptional terminator between the cloning site and the 5' end of the selectable marker region, oriented so as to terminate RNA transcripts entering the 5' end of said selectable marker region from the cloning site, and v) a ["3'-end"] transcriptional terminator between the cloning site and the 3' end said selectable marker region, oriented so as to terminate RNA transcripts entering the 3' end of the selectable marker region from the cloning site. In other embodiments, the circular vector is configured such that it may be cleaved to generate a linear fragment. In some embodiments, the circular vector further comprises i) a gene that is toxic when expressed in a host cell, ii) restriction sites that allow excision of the toxic gene, and wherein the circular vector is configured [e.g. by excision of said toxic gene or by PCR amplification to generate a linear fragment. In some embodiments, the present invention provides circular vectors comprising i) a gene that is toxic when expressed in a host cell, and ii) one or more unique restriction sites within the toxic gene, and wherein insertion of exogenous DNA into any of the one or more unique restriction sites is likely to result in disruption of expression of the toxic gene, allowing maintenance of the resulting recombinant vector in host cells.

In some embodiments, the present invention provides compositions comprising a circular vector, wherein the circular vector comprises; i) a toxic gene sequence, and ii) a nucleic acid sequence, wherein the nucleic acid sequence comprises; a) first and second ends, b) a selectable marker region, c) a first transcriptional terminator between the first end and the selectable marker region, and d) a second transcriptional terminator between the second end and the selectable marker region. In certain embodiments, the circular vector is configured to generate a vector component having first and second free ends upon removal of the toxic gene sequence from the circular vector. In other embodiments, the 3. The first transcriptional terminator is configured to terminate RNA transcripts entering the selectable marker region from the first end. In particular embodiments, the second transcriptional terminator is configured to terminate RNA transcripts entering the selectable marker region from the second end.

In some embodiments, the selectable marker region comprises a transcriptional terminator configured to terminate RNA transcripts encoded by at least one selectable marker sequence in the selectable marker region. In other embodiments, the nucleic acid sequence comprises a first non-promoter sequence between the first end and the selectable marker region, and a second non-promoter sequence between the second end and the selectable marker region, wherein each of the first and second non-promoter sequences are unable to serve as an operable promoter in a host cell. In preferred embodiments, the host cell is *Escherichia coli*.

In certain embodiments, the selectable marker region comprises first and second selectable marker sequences. In other embodiments, the selectable marker region further comprises a transcriptional terminator configured to terminate transcription of at least one of the first and second selectable marker sequences. In further embodiments, the nucleic acid sequence further comprises two primer binding sites. In some embodiments, expression of the toxic gene sequence prevents growth of a host cell. In particular embodiments, the circular vector further comprises a cloning site positioned such that introduction of an insert sequence into the cloning site diminishes or prevents expression of the toxic gene sequence. In other embodiments, the nucleic acid sequence comprises a promoter sequence between the first or second end and the selectable marker region.

In some embodiments, the selectable marker region comprises an ampicillin resistance sequence. In preferred embodiments, the ampicillin resistance sequence is a mutated ampicillin resistance sequence configured to reduce feeder colonies. In some embodiments, the mutated ampicillin resistance gene (e.g. derived from pUC19) comprises at least one mutation selected from: T to A at position 174; T to C at position 333; A to G at position 412, C to T at position 648; T to C at position 668; T to C at position 764; and combinations thereof. In certain embodiments, the natural promoter of the ampicillin resistance gene is replaced with a weaker promoter.

In certain embodiments, the circular vector is a recombinant plasmid. In preferred embodiments, the circular vector is low copy number vector (e.g. produces less than 300, or less than 200, or less than 100 or less than 50 or less than 20 copies per cell). In some embodiments, the vector component further comprises two primer binding sites. In preferred embodiments, the vector component comprises SEQ ID NO:85 or a sequence that is at least 90% identical to SEQ ID NO:85 (e.g. at least 95% or at least 98% identical to SEQ ID NO:85).

In some embodiments, the present invention provides kits comprising; a) a vector component, wherein the vector component comprises: i) first and second free ends; ii) a selectable marker region, iii) a first transcriptional terminator between the first free end and the selectable marker region, and iv) a second transcriptional terminator between the second free end and the selectable marker region, and wherein the vector component is configured to form a circular vector when combined with an insert sequence; and b) one other component (e.g., buffer, product insert, sequencing primers, ligase, etc.). In certain embodiments, there is a transcriptional terminator after the selectable marker region. In additional embodiments, the kits further comprise an insert DNA end repair component (e.g. comprising a polymerase and kinase). In certain embodiments, the kits of the present invention further comprise a written insert component (e.g. comprising written instructions). In certain embodiments, the selectable marker region comprises at least one selectable marker sequence.

In certain embodiments, the vector components of the present invention comprise at least one selectable marker sequence selected from an ampicillin selectable marker, a chloramphenicol selectable marker, a kanamycin selectable marker, a gentamycin selectable marker, and a plasmid origin of replication (e.g. serving as a selectable marker). In certain embodiments, the vector components comprise at least one transcriptional terminator. In some embodiments, the vector component comprise at least two, or at least three, transcriptional terminators (e.g. flanking a selectable marker). In certain embodiments, each selectable marker, including Ori as a selectable marker, is flanked by transcriptional terminators (e.g. strong transcriptional terminators). In particular embodiments, each of the X+1 vector components comprises at least one transcriptional terminator that is downstream of the selectable marker sequence (i.e. the transcriptional terminator is 3' of the stop codon in the selectable marker sequence, see Amp selectable marker sequence in FIG. 12B). In other embodiments, at least one of the X+1 vector components comprises first and second transcriptional terminators, wherein the first transcriptional terminator is downstream of a selectable marker sequence, and wherein the second transcriptional terminator is upstream of a selectable marker sequence (i.e. 5' of the start codon of the selectable marker sequence oriented to terminate transcripts entering the selectable marker sequence).

In particular embodiments of the present invention, at least one of the vector components comprises at least a portion of one of the at least two separate source nucleic acid molecules. In other embodiments, at least one of the vector components is amplified (e.g. using PCR) from at least a portion of one of the at least two separate source nucleic acid molecules (e.g. one of the separate source nucleic acid molecules is exposed to primers that amplify at least a portion of the sequence of the source nucleic acid molecule). In preferred embodiments, the vector components are linear (e.g. the vector components have ends that are not connected to each other). In other preferred embodiments, each of the vector components comprises at least two primer binding sites (e.g. to allow insert DNA adjacent to the vector components to be sequenced).

In some embodiments, the present invention provides systems, kits, and compositions for cloning nucleic acid comprising at least two separate source nucleic acid molecules capable of supplying X+1 vector components, wherein each of the source nucleic acid molecules is configured to supply no more than X of the vector components, and wherein the vector components are configured for combining in the presence of X+1 insert sequences to form a circular vector (e.g. recombinant plasmid) such that the X+1 vector components are non-contiguous within the circular vector. In particular embodiments, at least one of the at least two separate source nucleic acid molecules is a replicable vector (e.g. a vector that has an origin of replication and is therefore capable of being copied by a host cell). In some embodiments, the replicable vector is selected from a plasmid, a BAC, a cosmid, or a viral vector (e.g. bacteriophage).

In some embodiments, at least one of the at least two separate source nucleic acid molecules is a direct selection vector (e.g. a vector with a lethal gene that has a cloning site in it). In other embodiments, at least one of the at least two separate source nucleic acid molecules is a conditional replication vector. In particular embodiments, at least one of the source nucleic acid molecules comprises at least one of the vector components. In certain embodiments, at least one of the source nucleic acid molecules is a vector component.

In other embodiments, all of the source nucleic acid molecules are vector components. In certain embodiments, at least one of the source nucleic acid molecules comprises a template for generating at least one of the vector components (e.g., by amplification of the template by PCR).

In certain embodiments, the vector components are linear with free 5' and 3' ends (e.g. in a double stranded vector component, both 5' ends and both 3' ends are not linked to other nucleic acid sequences). In some embodiments, each of the vector components comprises free ends not compatible with the free ends of the other vector components (e.g. the 5' end of the vector components are not able to bind to either 3' end of another vector component, or to their own 3' end). In preferred embodiments, the free 5' ends of the vector components lack terminal phosphate groups. In some embodiments, the ends of the vector components comprise blunt free ends.

In some embodiments, at least one of the insert sequences is of unknown sequence. In particular embodiments, each of the insert sequences is of unknown sequence. In preferred embodiments, at least one of the X+1 insert sequence is a lethal or toxic insert sequence (e.g. will not allow the host cell to form a colony if the insert sequence is transcribed, which may be determined by also cloning the insert sequence in a conventional vector, such as pUC19, to see if the insert sequence when transcribed is toxic or lethal). In certain embodiments, the circular vector is capable of being maintained by a host cell when the insert sequence has at least 65% A/T content (e.g. at least 65%, 75%., 80%, or 85% A/T content). In particular embodiments, the sequence of at least one of the insert sequences is known. In particular embodiments, the sequence of at least two insert sequences is known. In certain embodiments, at least a portion of the sequence of at least one of the insert sequences is known (e.g. 5, 10, 15, 20, 25 bases are known). In other embodiments, the sequence of at least one of the insert sequences in unknown. In particular embodiments, the sequence of at least two of the X+1 insert sequences is the same (e.g. the circular vector formed has at least two insert sequences that have the same sequence). In some embodiments, each of the insert sequences is at least 20 base pairs in length. In other embodiments, each of the insert sequences is at least 100 base pairs in length. In yet other embodiments, each of the insert sequences is at least 50, or at least 200, or at least 500, or at least 750, or at least 1000 base pairs in length. In other embodiments, the insert sequences are from a shotgun cloning library. In other embodiments, the insert sequences are greater than 1000 base pairs in length (e.g. between 1001 and 7000). In some embodiments, the insert sequences are between 2000 and 6000 base pairs in length. In further embodiments, the insert sequences are greater than 7000 base pairs in length. In particular embodiments, the insert sequences are identical (e.g. all of the X+1 insert sequences have the same sequence).

In certain embodiments, each of the insert sequences is linear (e.g. its ends are not ligated to each other to form a closed loop). In particular embodiments, each of the insert sequences is double stranded. In some embodiments, each of the insert sequences is configured to bind two of the vector components. In certain embodiments, each of the insert sequences is capable of binding to: i) one of the vector components and, ii) one other of the insert sequences. In particular embodiments, at least one of the at least X+1 insert sequences comprises a DNA library. In particular embodiments, none of the at least X+1 insert sequences comprises a DNA library. In other embodiments, the insert sequences comprise DNA. In particular embodiments, the insert sequences comprise RNA.

In some embodiments, the termini of the vector components are configured to provide fixed orientation multiplex cloning vectors, in which the vector components can assemble only in a fixed orientation relative to each other upon ligation to insert DNA fragments. For example, in some embodiments, each of the X+1 insert sequences i) is configured to bind only two of the X+1 vector components, but not to itself or to any other insert sequence, and ii) is combined with X+1 vector components, each of the vector components being configured to bind only two of the X+1 insert sequences, but not to itself or to any other vector component (e.g. the 5' end of the vector component is not able to bind to the 3' end of another vector component or to its own 3' end; see FIG. 16). As such, the vector components can be assembled by ligation to the insert DNAs only in a fixed orientation relative to each other. This arrangement allows for "paired-end" sequencing, in which the ends of a given insert fragment are adjacent to a defined pair of sequencing primers. The vector components may be configured such that specific desired ends are generated by restriction digestion, by PCR amplification, or by ligation of oligonucleotide linkers. Specific desired ends of the insert DNAs may be generated by ligating oligonucleotide linkers onto each of X+1 pools of insert DNAs. In addition to providing fixed orientation of the vector fragments, this method of multiplex cloning eliminates the possibility of cloning multiple insert fragments into a single cloning site.

In some embodiments, the present invention provides kits for cloning nucleic acid comprising at least two separate source nucleic acid molecules capable of supplying X+1 vector components, wherein the vector components are configured for combining in the presence of X+1 insert sequences to form a closed vector (e.g. recombinant vector). In particular embodiments, the present invention provides kits for cloning nucleic acid comprising at least two separate source nucleic acid molecules capable of supplying X+1 vector components, wherein the X+1 vector components are configured for combining in the presence of X+1 insert sequences to form a circular vector (e.g. recombinant plasmid).

In some embodiments, the present invention provides kits for cloning nucleic acid comprising at least two separate source nucleic acid molecules capable of supplying X+1 vector components, wherein the vector components are configured for combining in the presence of X+1 insert sequences to form a circular vector, and wherein the vector components are non-contiguous within the circular vector. In some embodiments, X is a positive integer (e.g. 1–100). In particular embodiments, X is selected from 1, 2, 3, 4, 5, and 6. In other embodiments, the present invention provides kits for cloning nucleic acid comprising at least two separate source nucleic acid molecules capable of supplying at least two vector components, wherein the two vector components are configured for combining in the presence of two insert sequences to form a circular vector, and wherein the two vector components are non-contiguous with the circular vector. In some embodiments, the present invention provides kits for cloning nucleic acid comprising at least two separate source nucleic acid molecules capable of supplying at least three vector components, wherein the three vector components are configured for combining in the presence of at least three insert sequences to form a circular vector, and wherein the vector components are non-contiguous within the circular vector.

In some embodiments, the present invention provides compositions for cloning nucleic acid comprising at least two separate source nucleic acid molecules capable of supplying X+1 vector components, wherein the X+1 vector components are configured for combining in the presence of X+1 insert sequences to form a closed vector (e.g. recombinant plasmid). In particular embodiments, the present invention provides compositions for cloning nucleic acid comprising at least two separate source nucleic acid molecules capable of supplying X+1 vector components, wherein the vector components are configured for combining in the presence of X+1 insert sequences to form a circular vector (e.g. recombinant plasmid).

In some embodiments, the present invention provides compositions for cloning nucleic acid comprising at least two separate source nucleic acid molecules capable of supplying X+1 vector components, wherein the vector components are configured for combining in the presence of X+1 insert sequences to form a circular vector, and wherein the vector components are non-contiguous within the circular vector. In some embodiments, X is a positive integer. In particular embodiments, X is selected from 1, 2, 3, 4, 5, and 6. In other embodiments, the present invention provides compositions for cloning nucleic acid comprising at least two separate source nucleic acid molecules capable of supplying at least two vector components, wherein the vector components are configured for combining in the presence of at least two insert sequences to form a circular recombinant plasmid, and wherein the vector components are non-contiguous with the circular recombinant plasmid. In some embodiments, the present invention provides compositions for cloning nucleic acid comprising at least two separate source nucleic acid molecules capable of supplying at least three vector components, wherein the vector components are configured for combining in the presence of at least three insert sequences to form a circular recombinant plasmid, and wherein the vector components are non-contiguous with the circular recombinant plasmid.

In some embodiments, the present invention provides compositions comprising a vector, wherein the vector comprises; i) X+1 vector components, and ii) X+1 insert sequences; and wherein the vector components are non-contiguous within the recombinant plasmid. In particular embodiments, the vector is a circular vector. In other embodiments, the vector is a linear vector. In certain embodiments, the vector components are derived from at least two separate source nucleic acid molecules. In certain embodiments, the vector components of the present invention comprise at least one selectable marker sequence. In other embodiments, the vector components comprise at least two selectable marker sequences. In preferred embodiments, the vector components comprises at least one unique selectable marker sequence (e.g. each vector component has at least one selectable marker sequence not found on the other vector components that make up the circular vector). In certain embodiments, the vector components comprise at least one selectable marker sequence selected from an ampicillin selectable marker, a chloramphenicol selectable marker, a kanamycin selectable marker, a gentamycin selectable marker, and a plasmid origin of replication (e.g. serving as a selectable marker).

In particular embodiments of the compositions of the present invention, at least one of the vector components comprise at least a portion of one of the at least two separate source nucleic acid molecules. In other embodiments, at least one of the vector components is amplified (e.g. by PCR) from at least a portion of one of the at least two separate source nucleic acid molecules (e.g. one of the separate source nucleic acid molecules is exposed to primers that amplify at least a portion of the sequence of the source nucleic acid molecule). In preferred embodiments, the vector components are linear (e.g. they have ends that are not connected to each other). In other preferred embodiments, the vector components comprise at least two primer binding sites (e.g. to allow insert DNA adjacent to the vector components to be sequenced).

In some embodiments, the present invention provides compositions for cloning nucleic acid comprising at least two separate source nucleic acid molecules capable of supplying X+1 vector components, wherein each of the source nucleic acid molecules is configured to supply no more than X of the vector components, and wherein the vector components are configured for combining in the presence of X+1 insert sequences to form a circular vector (e.g. recombinant plasmid), and wherein the vector components are non-contiguous within the circular vector. In particular embodiments, at least one of the at least two separate source nucleic acid molecules is a replicable vector (e.g. a vector that has an origin of replication, and is capable of being copied by a host cell). In some embodiments, the replicable vector is selected from a plasmid, a BAC, a cosmid, a viral vector (e.g. bacteriophage).

In some embodiments, at least one of the at least two separate source nucleic acid molecules is a direct selection vector (e.g. a vector with a lethal gene that has a cloning site in it). In other embodiments, at least one of the at least two separate source nucleic acid molecules is a conditional replication vector. In particular embodiments, at least one of the source nucleic acid molecules comprises at least one of the vector components. In certain embodiments, at least one of the source nucleic acid molecules comprises a template for generating at least one of the vector components by amplification.

In certain embodiments, the vector components are linear with free 5' and 3' ends (e.g. in a double stranded vector component, both 5' ends and both 3' ends are not linked to other nucleic acid sequences). In some embodiments, each of the vector components comprises free ends not compatible with the free ends of the other vector components (e.g. the 5' end of the vector components is not able to bind to either end of another vector component, or to its own 3' end). In preferred embodiments, the free ends of the vector components lack terminal 5' phosphate groups.

In some embodiments, at least one of the insert sequences is of unknown sequence. In particular embodiments, each of the insert sequences is of unknown sequence. In particular embodiments, the sequence of at least one of the insert sequences is known. In particular embodiments, the sequence of at least two of the insert sequences is known. In certain embodiments, at least a portion of the sequence of at least one of the insert sequences in known (e.g. 5, 10, 15, 20, 25 bases are known). In other embodiments, the sequence of at least one of the insert sequences is unknown. In some embodiments, each of the insert sequences is at least 20 base pairs in length. In other embodiments, each of the insert sequences is at least 100 base pairs in length. In yet other embodiments, each of the insert sequences is at least 50, or at least 200, or at least 500, or at least 750, or at least 1000 base pairs in length. In other embodiments, the insert sequences are from a shotgun cloning library. In other embodiments, the insert sequences are between 1000 and 7000 base pairs in length. In some embodiments, the insert sequences are between 7000 and 12000 base pairs in length. In particular embodiments, the insert sequences are identical (e.g. all of the X+1 insert sequences have the same sequence).

In certain embodiments, each of the insert sequences is linear (e.g. its ends are not ligated to each other to form a closed loop). In particular embodiments, each of the insert sequences is double stranded. In some embodiments, each of the insert sequences are configured to bind two of the vector components. In certain embodiments, each of the insert sequences are capable of binding to: i) one of the vector components, and ii) one other of the insert sequences. In particular embodiments, at least one of the X+1 insert sequence comprises a DNA library. In other embodiments, the insert sequences comprise DNA. In particular embodiments, the insert sequences comprise RNA. In some embodiments, the insert sequences comprise ends that are phosphorylated.

In some embodiments, each of the X+1 insert sequences i) is configured to bind two of the vector components, but not to itself or to any other insert sequence, and ii) is combined with X+1 vector components, each of the vector components comprising one free end compatible with one of the insert ends and one free end compatible with another insert end, but not compatible with the free ends of the other vector components (e.g. the 5' end of the vector components is not able to bind to either 3' end of another vector component, or to its own 3' end) (see FIG. 16).

In some embodiments, the present invention provides compositions comprising a circular vector, wherein the circular vector comprises a plurality of cloning sites, each separated by at least one selectable marker sequence. In certain embodiments, the circular vector is a direct selection vector. In other embodiments, the circular vector is a conditional replication vector. In particular embodiments, the plurality of cloning sites comprises at least three cloning sites. In additional embodiments, the plurality of cloning sites comprises at least four (or five, or six, or seven) cloning sites. In some embodiments, at least one selectable marker sequence comprises two selectable marker sequences. In other embodiments, the selectable marker sequences comprises at least two primer binding sites. In particular embodiments, at least one selectable marker sequences selected from ampicillin, chloramphenicol, kanamycin, gentamycin, and a plasmid origin of replication. In some embodiments, the circular vector is a plasmid.

In some embodiments, the present invention provides compositions comprising a circular vector, wherein the circular vector comprises at least two selectable marker sequences, wherein each of the selectable marker sequences is flanked by cloning sites.

In other embodiments, the present invention provides composition comprising a circular vector, wherein the circular vector comprises at least two vector components, wherein each of the vector components comprises at least one selectable marker sequence, and wherein each of the vector components is flanked by cloning sites.

In certain embodiments, the present invention provides methods for cloning nucleic acid comprising: a) providing; i) at least two separate source nucleic acid molecules, and ii) at least X+1 insert sequences and b) treating the at least two separate source nucleic acid molecules under conditions such that at least X+1 vector components are generated; and c) combining the at least X+1 insert sequences with the at least X+1 vector components under conditions such that a circular recombinant vector is generated, wherein the vector components are non-contiguous within the circular vector. In some embodiments, the method further comprises: providing; iii) host cells, and step d) transfecting the host cells with the circular vector (e.g., recombinant plasmid) generating transfected cells. In other embodiments, the method further comprises; providing iv) selective growth media, and step e) treating the transfected cells with the selective media to select cells containing X+1 insert sequences.

In particular embodiments, step c) generates a plurality of circular vectors (e.g. recombinant plasmids), and the method further comprises step f) identifying the cells containing X+1 insert sequences, wherein the identifying is at least 95% accurate (e.g. there is only 5% that is false positives). In preferred embodiments, the identifying is at least 98% accurate. In particularly preferred embodiments, the identifying is at least 99% accurate. In most preferred embodiments, the identifying is approximately 100% accurate (e.g. 99.5% or greater). In certain embodiments, the selective growth media comprises at least X+1 selective agents. In different embodiments, the selective growth media comprises X selective agents (e.g. an origin of replication being employed as a selective marker). In some embodiments, the selective agents are selected from ampicillin, chloramphenicol, kanamycin, and gentamycin.

In some embodiments, the method further comprises providing multiplex sequencing reagents, and step d) mixing the multiplex sequencing reagents with the circular vector (e.g. recombinant plasmid) under conditions such that at least a portion of each of the X+1 insert sequences are sequenced (e.g. at least 5, 10, 15, 20, 25, 100 bases are determined from each of the insert sequences). In preferred embodiments, at least 400, or 500 bases are determined from each of the insert sequences. In particularly preferred embodiments, at least 500 or at least 700 bases are determined from each of the insert sequences. In some embodiments, the multiplex sequencing reagents comprise: i) at least two primers for each of the X+1 insert sequences, ii) a nucleic acid polymerizing agent, and iii) nucleotides, wherein a portion of the nucleotides are di-deoxy nucleotides.

In certain embodiments, the present invention provides methods for cloning nucleic acid comprising: a) providing; i) at least two separate source nucleic acid molecules, and ii) at least X+1 insert sequences, and b) treating the at least two separate source nucleic acid molecules under conditions such that at least X+1 vector components are generated: and c) combining the at least X+1 insert sequences with the at least X+1 vector components under conditions such that a circular vector (e.g. recombinant plasmid) is generated. In certain embodiments, the treating comprises exposing the at least two separate source nucleic acid molecules to restriction enzymes and/or alkaline phosphatase. In other embodiments, the treating comprises employing at least a portion of one of the at least two separate source nucleic acid molecules as a template for PCR.

In certain embodiments, the X+1 vector components of the present invention comprise at least one selectable marker sequence. In some embodiments, the vector components comprise: i) first and second free ends, and ii) a selectable marker region comprising at least one selectable marker sequence unique among the X+1 vector components. In further embodiments, the X+1 vector components further comprise a first transcriptional terminator between the first free end and the selectable marker region. In other embodiments, the X+1 vector components comprise a second transcriptional terminator between the second free end and the selectable marker region. In other embodiments, the vector components comprise at least two selectable marker sequences. In preferred embodiments, the vector components comprises at least one unique selectable marker sequence (e.g. each vector component has at least one selectable marker sequence not found on the other vector components that make up the circular vector). In certain embodiments, the vector components comprise at least one selectable marker sequence selected from an ampicillin selectable marker, a chloramphenicol selectable marker, a kanamycin selectable marker, a gentamycin selectable marker, tetracycline, and a plasmid origin of replication (e.g. serving as a selectable marker). In some embodiments, the selectable marker sequences are antibiotic resistance genes. In certain embodiments, there is a transcriptional terminator after the selectable marker sequence.

In particular embodiments of the methods of the present invention, at least one of the vector components comprise at least a portion of one of the at least two separate source nucleic acid molecules. In other embodiments, at least one of the vector components is PCR generated from at least a portion of one of the at least two separate source nucleic acid molecules (e.g. one of the separate source nucleic acid molecules is exposed to primers that amplify at least a portion of the sequence of the source nucleic acid molecule). In preferred embodiments, the vector components are linear (e.g. the have ends that are not connected to each other). In other preferred embodiments, the vector components comprise at least two primer binding sites (e.g. to allow insert DNA adjacent to the vector components to be sequenced).

In particular embodiments, at least one of the at least two separate source nucleic acid molecules is a replicable vector (e.g. a vector that has an origin of replication, and is capable of being copied by a host cell). In some embodiments, the replicable vector is selected from a plasmid, a BAC, a cosmid, a viral vector (e.g. bacteriophage).

In some embodiments, at least one of the at least two separate source nucleic acid molecules is a direct selection vector (e.g. a vector with a lethal gene that has a cloning site in it). In other embodiments, at least one of the at least two separate source nucleic acid molecules is a conditional replication vector. In particular embodiments, at least one of the source nucleic acid molecules comprises at least one of the vector components. In certain embodiments, at least one of the source nucleic acid molecules comprises a template for generating at least one of the vector components (e.g. by amplification).

In certain embodiments, the vector components are linear with free 5' and 3' ends (e.g. in a double stranded vector component, both 5' ends and both 3' ends are not linked to other nucleic acid sequences). In some embodiments, each of the vector components comprises free ends not compatible with the free ends of the other vector components (e.g. the 5' end of the vector components is not able to bind to either end of another vector components, or to its own 3' end). In preferred embodiments, the free ends of the vector components lack terminal phosphate groups.

In some embodiments, at least one of the insert sequences is of unknown sequence. In particular embodiments, each of the insert sequences is of unknown sequence. In particular embodiments, the sequence of at least one of the insert sequences is known. In particular embodiments, the sequence of both of the insert sequences is known. In certain embodiments, at least a portion of the sequence of at least one of the insert sequences in known (e.g. 5, 10, 15, 20, 25 bases are known). In other embodiments, the sequence of at least one of the insert sequences is unknown. In some embodiments, each of the insert sequences is at least 20 base pairs in length. In other embodiments, each of the insert sequences is at least 100 base pairs in length. In yet other embodiments, each of the insert sequences is at least 50, or at least 200, or at least 500, or at least 750, or at least 1000 base pairs in length. In other embodiments, the insert sequences are from a shotgun cloning library. In other embodiments, the insert sequences are between 1000 and 7000 base pairs in length. In some embodiments, the insert sequences are between 7000 and 12000 base pairs in length. In particular embodiments, the insert sequence are identical (e.g. all of the X+1 insert sequences have the same sequence).

In certain embodiments, each of the insert sequences is linear (e.g. its ends are not ligated to each other to form a closed loop). In particular embodiments, each of the insert sequences is double stranded. In some embodiments, each of the insert sequences is configured to bind two of the vector components. In certain embodiments, each of the insert sequences is capable of binding to: i) one of the vector components and, ii) one other of the insert sequences. In particular embodiments, at least one of the at least X+1 insert sequence comprises a DNA library. In other embodiments, the insert sequences comprise DNA. In particular embodiments, the insert sequences comprise RNA.

In some embodiments, each of the X+1 insert sequences i) is configured to bind two of the vector components, but not to itself or to any other insert sequence, and ii) is combined with X+1 vector components, each of the vector components comprising one free end compatible with one of the insert ends and one free end compatible with another insert end, but not compatible with the free ends of the other vector components (e.g. the 5' end of the vector components is not able to bind to the 3' end of another vector components, or to its own 3' end) (see, e.g., FIG. 16).

In certain embodiments, the present invention provides methods for cloning nucleic acid comprising; providing; i) at least X+1 vector components, and ii) at least X+1 insert sequences; and b) combining the at least X+1 insert sequences with the at least X+1 vector components under conditions such that a circular recombinant plasmid is generated, wherein the vector components are non-contiguous within the circular recombinant plasmid.

In other embodiments, the present invention provides methods for sequencing nucleic acid comprising: a) providing; i) a circular vector comprising; A) X+1 vector components, and B) X+1 insert sequences; and wherein the vector components are non-contiguous within the circular recombinant plasmid, and ii) multiplex sequencing reagents; and b) mixing the multiplex sequencing reagents with the circular vector under conditions such that at least a portion of each of the X+1 insert sequences are sequenced. In some embodiments, the multiplex sequencing reagents comprise: i) at least two primers for each of the X+1 insert sequences, ii) a nucleic acid polymerizing agent, and iii) nucleotides, wherein a portion of the nucleotides are di-deoxy nucleotides.

In certain embodiments, the present invention provides methods comprising combining a plurality of vector components and a plurality of insert sequences under conditions such that a circular recombinant plasmid containing two or more of the insert sequences is formed (in some embodiments the vector components are non-contiguous). In some embodiments, the circular recombinant plasmid contains three or more of the insert sequences. In particular embodiments, the circular recombinant plasmid contains four or more of the insert sequences.

In some embodiments, the present invention provides compositions comprising a direct selection vector, wherein the direct selection vector comprises; i) a plasmid origin of replication, and ii) a bacteriophage T7 1.2 gene sequence (or a sequence encoding a protein identical to the T7 1.2 gene product, or a sequence encoding a protein that has the same biological activity as the T7 1.2 gene, e.g. the amino acid sequence for T7 1.2 with minor deletions, substitutions, or additions, that do not alter the biological activity of the peptide). In particular embodiments, the direct selection vector further comprises at least one selectable marker sequence. In other embodiments, the direct selection vector further comprises a multiple cloning site. In certain embodiments, the multiple cloning site is derived from pUC19. In yet other embodiments, the multiple cloning site is located between the first and second codon of the bacteriophage T7 1.2 gene sequence. In yet other embodiments, the multiple cloning site is located between two other adjacent codons of the bacteriophage T7 1.2 gene sequence. In particular embodiments, the multiple cloning site comprises SEQ ID NO:29. In additional embodiments, the multiple cloning site comprises SEQ ID NO:30. In preferred embodiments, the direct selection vector is pT71.2. In other embodiments, the direct selection vector is pTM2. In some embodiments, the vector generated by the above method is pCTA1. In other embodiments, the vector generated by the above method is pCTAB4.3. In still other embodiments, the vector generated by the above method is pCTH1.4. In other embodiments, the vector generated by the above method is pATH. In other embodiments, the vector generated by the above method is pATBAG. In still other embodiments, the vector generated by the above method is pATR-G. In certain embodiments, the vector generated by the above method is pAT6-6. In other embodiments, the vector generated by the above method is pARG. In certain embodiments, the bacteriophage T7 1.2 gene is lethal in F' *E. coli* cells.

In certain embodiments, the present invention provides methods for generating a vector comprising: a) providing; i) a direct selection vector comprising; A) a plasmid origin of replication, and B) a bacteriophage T7 1.2 gene sequence; ii) a composition comprising at least one type of restriction enzyme; and iii) in certain embodiments a composition comprising a phosphatase (e.g. calf intestinal phosphatase); and b) exposing the direct selection vector to the composition under conditions such that the bacteriophage T7 1.2 gene is removed from the direct selection vector. In some embodiments, the exposing step generates a cloning vector, or vector component, lacking the bacteriophage T7 1.2 gene sequence. In further embodiments, the present invention provides a compositions comprising the vector lacking the bacteriophage T7 1.2 gene, generated by the above method.

In some embodiments, the present invention provides methods for generating a vector component comprising; a) providing; i) a circular vector comprising; A) a selectable marker region, B) a direction selection sequence (e.g. T7 1.2 gene or Barnase), C) a first transcriptional terminator upstream of the direct selection sequence, wherein the first transcriptional terminator is between the selectable marker region and the direct selection sequence, and D) a second transcriptional terminator downstream of the direct selection sequence, wherein the second transcriptional terminator is between the selectable marker region and the direct selection sequence; and ii) a composition comprising at least one type of restriction enzyme; and iii) in certain embodiments a composition comprising a phosphatase (e.g. calf intestinal phosphatase); and b) exposing the circular vector to the composition under conditions such that the direct selection sequence is removed from the circular vector, thereby generating a vector component with first and second free ends (e.g. blunt free ends). In certain embodiments, the method further comprises step c) exposing the vector component to a phosphatase (e.g. calf intestinal phosphatase), such that the free ends are dephosphorylated. In certain embodiments, the selectable marker region comprises at least one selectable marker followed by a transcriptional terminator.

In certain embodiments, the present invention provides methods comprising, a) providing; i) X+1 vector components, and ii) X+1 insert sequences; and b) combining the X+1 vector components and the X+1 insert sequences under conditions such that a circular vector is formed, wherein the X+1 vector components are non-contiguous with the circular vector. In some embodiments, each of the X+1 vector components comprises; i) first and second free ends, and ii) a selectable marker region comprising at least one selectable marker sequence unique among the X+1 vector components. In other embodiments, each of the X+1 vector components further comprises; iii) a first transcriptional terminator between the first free end and the selectable marker region, and iv) a second transcriptional terminator between the second free end and the selectable marker region. In particular embodiments, each of the X+1 vector components comprises a non-promoter sequence between the first free end and the selectable marker region, wherein the non-promoter sequence is unable to serve as an operable promoter in a bacterial host cell (e.g., *Escherichia coli*). In other embodiments, each of the X+1 vector components comprises a non-promoter sequence between the second free end and the selectable marker region, wherein the non-promoter sequence is unable to serve as an operable promoter in a bacterial host cell. In certain embodiments, the selectable marker region comprises at least one selectable marker followed by a transcriptional terminator.

In some embodiments, the method further comprises; providing iii) host cells, and step c) transfecting the host cells with the circular vector (e.g., recombinant plasmid) generating transfected cells. In other embodiments, the method further comprises; providing iv) selective growth media, and step d) treating the transfected cells with the selective media to select cells containing X+1 insert sequences.

In particular embodiments, step b) generates a plurality of circular vectors (e.g. recombinant plasmids), and the method further comprises step e) identifying the cells containing X+1 insert sequences, wherein the identifying is at least 95% accurate (e.g. there is only 5% or less that are false positives). In preferred embodiments, the identifying is at least 98% accurate. In particularly preferred embodiments, the identifying is at least 99% accurate. In most preferred embodiments, the identifying is approximately 100% accurate (e.g. 99.5% or greater)

In some embodiments, the present invention provides methods comprising, a) providing; i) a vector component, wherein the vector component comprises: A) first and second free ends; B) a selectable marker region, C) a first transcriptional terminator between the first free end and the selectable marker region, and D) a second transcriptional terminator between the second free end and the selectable marker region, and ii) and an insert sequence, and b) combining the vector component and the insert sequence under conditions such that a circular vector is formed. In certain embodiments, the vector component further comprises a non-promoter sequence between the first free end and the selectable marker region, wherein the non-promoter sequence is unable to serve as an operable promoter in a bacterial host cell (e.g. *Escherichia coli*). In particular embodiments, the vector component comprises a non-promoter sequence between the second free end and the selectable marker region, wherein the non-promoter sequence is unable to serve as an operable promoter in a bacterial host cell (e.g. *Escherichia coli*). In some embodiments, the vector component comprises a third transcriptional terminator (e.g. after at least one selectable marker sequence).

In some embodiments, the method further comprises; further providing iii) host cells, and step c) transfecting the host cells with the circular vector (e.g., recombinant plasmid) generating transfected cells. In other embodiments, the method further comprises; providing iv) selective growth media, and step d) treating the transfected cells with the selective media to select cells containing X+1 insert sequences.

In particular embodiments, step b) generates a plurality of circular vectors (e.g. recombinant plasmids), and the method further comprises step e) identifying the cells containing X+1 insert sequences, wherein the identifying is at least 95% accurate (e.g. there is only 5% or less that are false positives). In preferred embodiments, the identifying is at least 98% accurate. In particularly preferred embodiments, the identifying is at least 99% accurate. In most preferred embodiments, the identifying is approximately 100% accurate (e.g. 99.5% or greater).

In certain embodiments, the present invention provides methods for fixed orientation cloning comprising; a) providing; i) X+1 vector components, wherein each of the X+1 vector components comprises two different sticky free ends, and ii) X+1 insert sequence pools, wherein each of the X+1 insert sequence pools comprises a plurality of insert sequences, and b) treating each of the X+1 insert sequence pools under conditions such that the plurality of insert sequences in each of the X+1 insert sequence pools comprise two identical sticky free ends that are unique among the X+1 insert sequence pools, and c) combining the X+1 vector components and the X+1 sequence pools under conditions such that each of the two different sticky free ends, of each of the X+1 vector components, binds one of the plurality of insert sequences from one of the X+1 insert sequence pools. In some embodiments, the treating step comprises exposing the plurality of insert sequences in each of the X+1 insert sequence pools to a plurality of one type of linker (e.g. CCCC linkers and ligase are added to one of the pools, and TTTT linkers and ligase are added to a different pool). The present invention is not limited to the length or sequence of the linkers employed. Indeed, any type of linker oligonucleotide may be used. In preferred embodiments, each of the X+1 pools is exposed to a different type of linker. In certain embodiments, the treating step comprises exposing the plurality of insert sequences in each of the X+1 insert sequence pools to a plurality of one type of restriction enzyme (e.g. to generate sticky ends).

In particular embodiments, the present invention provides methods comprising; a) providing; i) X+1 vectors (e.g. circular or linearized), wherein each of the vectors comprises; A) an identical origin of replication (i.e. each of the X+1 vector components comprises the same origin of replication), and B) at least one selectable marker sequence unique among the X+1 vectors, ii) a plurality of insert sequences, and iii) host cells; and b) combining the X+1 vectors and the plurality of insert sequences under conditions such that X+1 recombinant vectors are generated; and c) transforming the host cells with the X+1 recombinant vectors (e.g. transforming the host cells with each of the X+1 vectors at approximately the same time) to generate transformed host cells. In further embodiments, the methods further comprise; providing iv) selective grow th media, and step d) treating the transformed host cells with the selective media to select cells containing X+1 recombinant vectors.

In certain embodiments, the selective growth media comprises at least X+1 selective agents. In different embodiments, the selective growth media comprises X selective agents (e.g. an origin of replication being employed as a selective marker). In some embodiments, the selective agents are selected from ampicillin, chloramphenicol, kanamycin, and gentamycin.

In some embodiments, the present invention provides methods comprising; a) providing; i) X+1 vectors (e.g. circular or linearized), wherein each of the vectors comprises; A) an identical origin of replication (i.e. each of the X+1 vector components comprises the same origin of replication), and B) at least one selectable marker sequence unique among the X+1 vectors, and ii) X+1 insert sequence pools; and b) combining each of the insert sequence pools with one of the X+1 vectors such that X+1 recombinant vector pools comprising recombinant vectors are generated, and c) contacting the host cells with the X+1 recombinant vector pools (e.g. transforming the host cells with each of the X+1 vector pools at approximately the same time) to generate transformed host cells. In further embodiments, the methods further comprise; providing iv) selective growth media, and step d) treating the transformed host cells with the selective media to select cells containing X+1 recombinant vectors.

In certain embodiments, the present invention provides compositions, systems, and kits comprising a circular vector (e.g. plasmid), wherein the circular vector comprises a barnase encoding nucleic acid sequence, and wherein the circular vector does not contain an operable barstar encoding nucleic acid sequence. In some embodiments, the present invention provides cells comprising a circular vector (e.g. plasmid), wherein the circular vector comprises a barnase encoding nucleic acid sequence, and wherein the circular vector does not contain an operable barstar encoding nucleic acid sequence. In other embodiments, the present invention provides cells comprising i) a first circular vector (e.g. plasmid), wherein the first circular vector comprises a barnase encoding nucleic acid sequence, and wherein the first circular vector does not contain an operable barstar encoding nucleic acid sequence, and ii) a second circular vector comprising a barstar encoding nucleic acid sequence.

In certain embodiments, the present invention provides methods comprising; a) providing; i) a plurality of circular vectors (e.g. plasmids), wherein the circular vectors comprise a barnase encoding nucleic acid sequence, and wherein the circular vectors do not contain an operable barstar encoding nucleic acid sequence, ii) host cells that do not contain a nucleic acid sequence encoding barnase, and iii) a plurality of insert sequences; b) combining the plurality of circular vectors and the plurality of insert sequences such that a plurality of recombinant vectors are generated, c) transforming the host cells with the plurality of recombinant vectors to generate a plurality of transformed cells, and d) plating the plurality of transformed cells on selective media such that transformed cells containing recombinant circular vectors with disrupted barnase encoding nucleic acid sequences are identified.

In certain embodiments, the present invention provides compositions comprising X+1 vector components configured for cloning X+1 insert sequences with a false positive background of less than 5%, or less than 2% or less than 1% (e.g. 0.5% false positives). In certain embodiments, the present invention provides compositions comprising a plurality of circular vectors configured to yield at least 98% recombinant clones when grown on selective media (e.g., approximately 99% or 99.50% or greater recombinant clones), wherein at least a portion of the circular vectors comprise at least two insert sequences. In some embodiments, the present invention provides compositions comprising a vector configured to clone at least one insert (e.g. one insert) without transcription of the insert sequence when transformed into a host cell. In other embodiments, the present invention provides compositions comprising a vector configured to clone at least two insert sequences without transcription of the insert sequences when transformed into a host cell.

DESCRIPTION OF THE FIGURES

FIG. 11 shows the nucleic acid sequence for SEQ ID NO:41.

FIG. 12A shows a schematic of a vector component (designated pSMART).

FIG. 12B shows a schematic of two vector components (together designated pLEXX-AK) configured to form a circular plasmid upon combining with two insert sequences.

FIG. 14A shows the sequence (SEQ ID NO:85) of the vector component shown in FIGS. 12A and 12B, and FIG. 14B shows the sequence (SEQ ID NO:86) of the vector component shown in FIG. 12B.

DEFINITIONS

Figure 1:
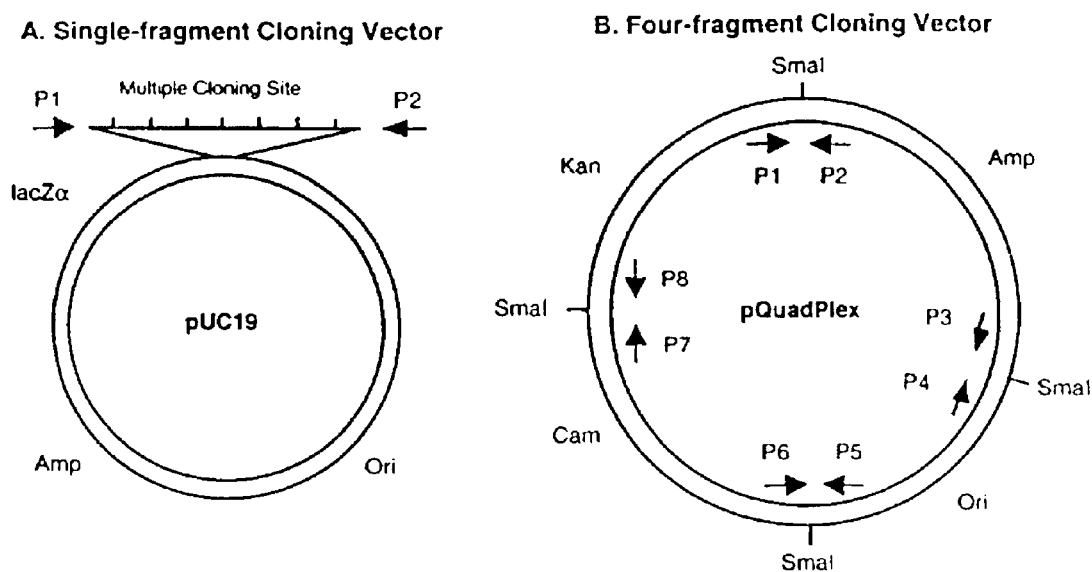
FIG. 1 shows a schematic diagram illustrating certain differences between conventional single-fragment cloning vectors and a multiplex vector of the present invention (e.g. with dispersed restriction sites) capable of co-cloning, independent insert sequences (e.g. four independent insert sequences are shown in this embodiment). The hash marks indicate restriction sites. P1–8 indicates primer-binding sites. Amp; ampicillin resistance gene, Cam; chloramphenicol resistance gene, Kan; kanamycin resistance gene, lacZα; alpha fragment of the lacZ gene, Ori; origin of replication, SmaI; recognition site for SmaI restriction endonuclease.

To facilitate an understanding of the invention, a number of terms are defined below.

As used herein, the term "nueleotide" refers to a monomeric unit of nucleic acid (e.g. DNA or RNA) consisting of a sugar moiety (pentose), a phosphate group, and a nitrogenous heterocyclic base. The base is linked to the sugar moiety via the glycosidic carbon (1' carbon of the pentose) and that combination of base and sugar is called a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence" or "nucleic acid sequence," and is represented herein by a formula whose left to right orientation is in the conventional direction of 5'-terminus to 3'-terminus.

As used herein, the term "base pair" refers to the hydrogen bonded nucleotides of, for example, adenine (A) with thymine (T), or of cytosine (C) with guanine (G) in a double stranded DNA molecule. In RNA, uracil (U) is substituted for thymine. This term base pair is also used generally as a unit of measure for DNA length. Base pairs are said to be "complementary" when their component bases pair up normally by hydrogen bonding, such as when a DNA or RNA molecule adopts a double stranded configuration.

As used herein, the terms "nucleic acid" and "nucleic acid molecule" refer to any nucleic acid containing molecule including, but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5 carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracils,5-methoxyaminomethyl-2-thiouracil, beta-D-maninosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

DNA molecules are said to have "5' ends" and "3' ends" because mononucleotides are joined to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. A double stranded nucleic acid molecule may also be said to have a 5' and 3' end, wherein the "5'" refers to the end containing the accepted beginning of the particular region, gene, or structure. A nucleic acid sequence, even if internal to a larger oligonucleotide, may also be said to have 5' and 3' ends (these ends are not 'free'). In such a case, the 5' and 3' ends of the internal nucleic acid sequence refer to the 5' and 3' ends that said fragment would have were it isolated from the larger oligonucleotide. In either a linear or circular DNA molecule, discrete elements may be referred to as being "upstream" or 5' of the "downstream" or 3' elements. Ends are said to "compatible" if a) they are both blunt or contain complementary single strand extensions (such as that created after digestion with a restriction endonuclease) and b) at least one of the ends contains a 5' phosphate group. Compatible ends are therefore capable of being ligated by a double stranded DNA ligase (e.g. T4 DNA ligase) under standard conditions.

As used herein, the term "hybridization" or "annealing" refers to the pairing of complementary nucleotide sequences (strands of nucleic acid) to form a duplex, heteroduplex, or complex containing more than two single-stranded nucleic acids, by establishing hydrogen bonds between/among complementary base pairs. Hybridization is a specific, i.e. non-random, interaction between/among complementary polynucleotides that can be competitively inhibited.

As used herein, the term "primer binding site" refers to the complimentary sequence of vector or other nucleic acid sequence to which an oligonucleotide primer can hybridize.

As used herein, the terms "insert sequence," "insert DNA," or "foreign DNA" refer to any nucleic acid sequences that are capable of being placed in a vector. Examples include, but are not limited to, random DNA libraries and known nucleic acid sequences. A particular "insert sequence," "insert DNA," or "foreign DNA" may refer to a pool or a member of a pool of identical nucleic acid molecules, a pool or a member of a pool of non-identical nucleic acid molecules, or a specific individual nucleic acid molecule.

As used herein, the term "circular vector" refers to a closed circular nucleic acid sequence capable of replicating in a host.

As used herein, the terms "vector" or "plasmid" is used in reference to extra-chromosomal nucleic acid molecules capable of replication in a cell and to which an insert sequence can be operatively linked so as to bring about replication of the insert sequence. Examples include, but are not limited to, circular DNA molecules such as plasmids constructs, phage constructs, cosmid vectors, etc., as well as linear nucleic acid constructs (e.g., lambda phage constructs, bacterial artificial chromosomes (BACs), etc.). A vector may include expression signals such as a promoter and/or a terminator, a selectable marker such as a gene conferring resistance to an antibiotic, and one or more restriction sites into which insert sequences can be cloned. Vectors can have other unique features (such as the size of DNA insert they can accommodate).

As used herein, the term "bacterial artificial chromosome" ("BAC") refers to a linear vector designed to propagate large insert sequences (e.g. approximately 50,000 to several hundred thousands bases in length) in host bacteria.

As used herein, the term "origin of replication" refers to a DNA sequence conferring functional replication capabilities in a host cell. Examples include, but are not limited to, normal or non-conditional origin of replications such as the ColE1 origin, and its derivatives, which are functional in a broad range of host cells.

As used herein, the term "conditional origin of replication" refers to an origin of replication that requires the presence of a functional trans-acting factor (e.g., a replication factor) in a prokaryotic host cell. Examples of conditional origins of replication include, but are not limited to, plasmid/bacteriophage fd hybrid replicons such as that in the plasmid pKf2, which contains the fd origin of replication. Replication of this type of plasmid requires the presence of the bacteriophage fd gene II protein. In conjunction with the host strain BHB2600, which was constructed to express the bacteriophage gene II protein, the fd origin is capable of autonomous replication and propagation. In any host lacking the trans-acting gene II protein, replication fails to occur. As used herein, a "conditional replication vector" means a vector that has a conditional origin of replication.

As used herein, the term "unique restriction enzyme site" refers to the recognition sequence for a given restriction enzyme that appears once within a nucleic acid molecule. For example, the EcoRI site is a unique restriction enzyme site within the plasmid pUC19.

As used herein, the terms "polylinker" or "multiple cloning site" refer to a cluster of restriction enzyme sites on a nucleic acid construct, which are utilized for the insertion, and/or excision of nucleic acid sequences.

As used herein, the term "host cell" refers to any cell that can be transformed with heterologous DNA (such as a vector). Examples of host cells include, but are not limited to, *E. coli* strains that contain the F or F' factor (e.g., DH5αF or DH5αF') or *E. coli* strains that lack the F or F' factor (e.g. DH10B).

As used herein, the term "direct selection vector" refers to a cloning vector that carries within it a toxic gene sequence who's effect can be suppressed (e.g. by insertion of a DNA fragment into a cloning site in the toxic gene, thereby inactivating the toxic activity of the toxic gene). When lacking a DNA insert in its cloning site, such a direct selection vector is generally lethal to a host bacterial strain. A direct selection vector containing a DNA insert within its cloning site is generally not lethal to a host bacterial strain.

The terms "nucleic acid molecule encoding," "DNA sequence encoding," and "DNA encoding" refer to a sequence of nucleotides, which upon transcription into RNA and subsequent translation into protein, would lead to the synthesis of a given peptide. Such transcription and translation may actually occur in vitro or in vivo, or it may be strictly theoretical, based on the standard genetic code.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends for a distance of about 1 kb or more on either end, such that the gene is capable of being transcribed into a full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "expression" as used herein is intended to mean the transcription (e.g. from a gene) and, in some cases, translation to gene product. In the process of expression, a DNA chain coding for the sequence of gene product is first transcribed to a complementary RNA, which is often a messenger RNA, and, in some cases, the transcribed messenger RNA is then translated into the gene protein product.

The term "prokaryotic termination sequence," "transcriptional terminator," or "terminator" refers to a nucleic acid sequence, recognized by an RNA polymerase, that results in the termination of transcription. Prokaryotic termination sequences commonly comprise a GC-rich region that has a twofold symmetry followed by an AT-rich sequence. A commonly used prokaryotic termination sequence is the T7 termination sequence. A variety of termination sequences are known in the art and may be employed in the nucleic acid constructs of the present invention, including the $T_{INT}$, $T_{L1}$, $T_{L2}$, $T_{R1}$, $R_{R2}$, $T_{6S}$ termination signals derived from the bacteriophage lambda, and termination signals derived from bacterial genes such as the trp gene of E. coli.

As used herein, the terms "selectable marker," "selectable marker sequence," or "selectable marker gene" refers to a gene, or other DNA fragment, which encodes or provides an activity that confers the ability to grow or survive in what would otherwise be a deleterious environment. For example, a selectable marker may confer resistance to an antibiotic or drug upon the cell in which the selectable marker is expressed. An origin of replication (Ori) may also be used as a selectable marker enabling propagation of a plasmid vector.

As used herein, the phrase "selectable marker region," in reference to vector sequence, refers to the portion of a vector component that contains all of the selectable marker sequences present on a particular vector component. In other words, the ends of selectable marker sequences present define the selectable marker region. For example, if a particular vector component only had one selectable marker sequence, the selectable marker region would be defined by the beginning of the selectable marker sequence and the end of the selectable marker sequence (see FIG. 16B, where the arrow tip of the Kan sequence is one end of the selectable marker region, and the other flat (non-arrow) end of the Kan sequence is the other end of the selectable marker region). If a particular vector component had, for example, two selectable marker sequences, the selectable marker region is the nucleic acid sequence between the beginning of the first selectable marker sequence and the end of the second selectable marker sequence (see FIG. 16B, where the arrow tip of the Ori sequence is one end of the selectable marker region, and the flat (non-arrow) end of the Amp sequence is the other end of the selectable marker region for this particular vector component).

As used herein, the phrase "at least one selectable marker sequence unique among said X+1 vector components," when used to describe what a particular vector component contains, indicates that a particular vector component, out of the total X+1 vector components, contains at least one selectable marker sequence that is not present on any of the other vector components (i.e. not present on any of the other X vector components). Likewise, as used herein, the phrase "two identical free ends that are unique among said X+1 insert sequences" when used to describe the identical ends of a particular insert sequence, indicates that a particular insert sequence, out of the total X+1 insert sequences, has identical ends that are not present on any of the other insert sequences (i.e. not present on any of the other X insert sequences).

As used herein, the term "unique selectable marker sequence" refers to a selectable marker that is present only on one of the vector components that are combined to form a circular vector (e.g. when a circular vector is formed having X+1 insert sequences and X+1 vector components, each of the vector components has at least one selectable marker that is not found on the other vector component making up the circular vector).

Figure 16:
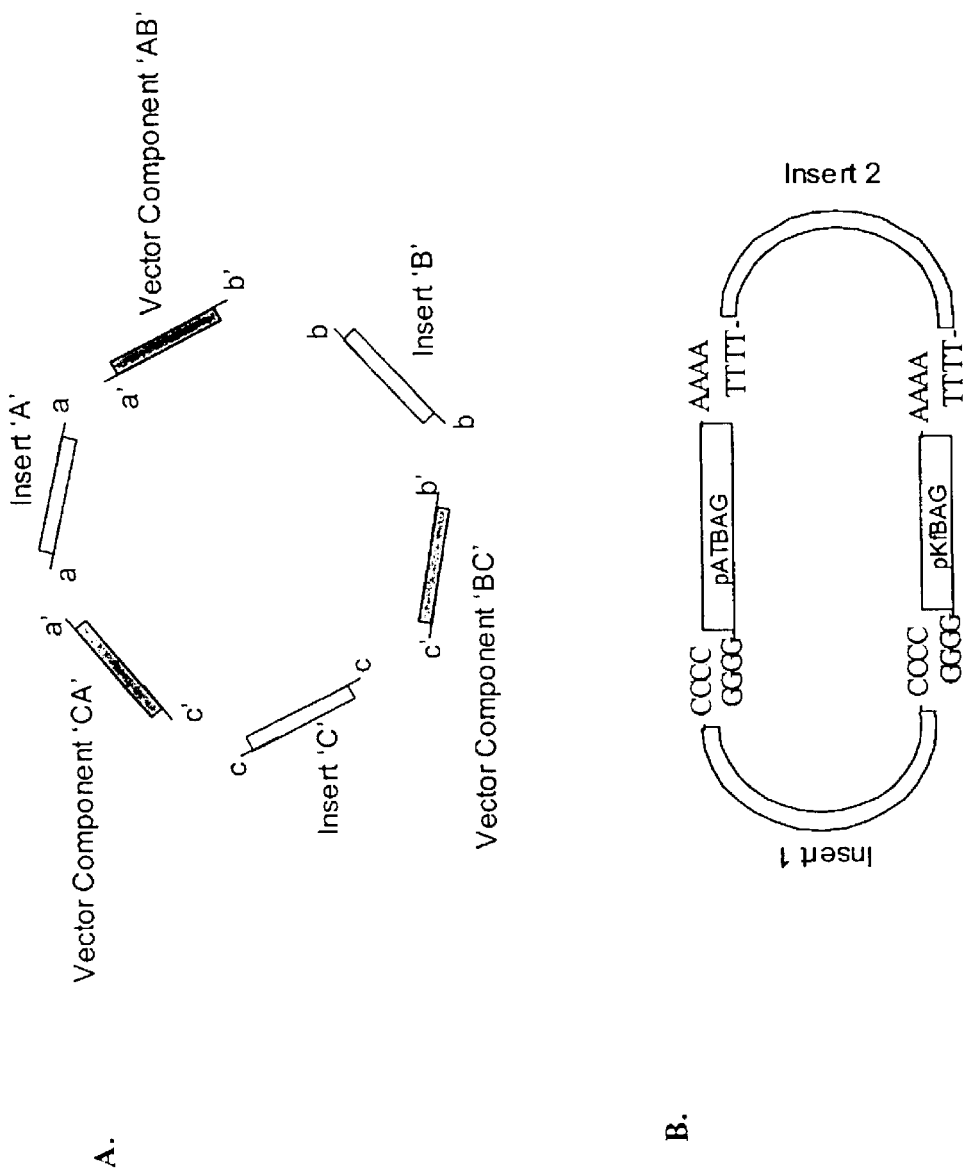
FIG. 16A shows a schematic diagram illustrating one embodiment of Fixed Orientation Multiplex Cloning in which vector components may be assembled only in a defined orientation relative to each other. Vector components AB, BC, and CA are ligated to insert DNA fragments A, B, and C. The termini of the inserts, labeled "a," "b," or "c," are compatible only to the termini labeled "a'," "b'," and "c'," respectively, which are present on the vector components.
FIG. 16B shows Fixed Orientation Multiplex Cloning as described in Example 15. Vector components pATBAG and pKfBAG were digested with BstX1 to generate termini of AAAA-3' and GGGG-3' on each component. Insert fragment pools #1 and #2 were ligated with linkers to generate termini of CCCC-3' or TTTT-3', respectively.

As used herein, the phrase "two different free ends that are non-unique among said X+1 vector components" when used to describe the different ends of a particular vector component, indicates that each of the two different free ends of a particular vector component, out of the total X+1 vector components, are identical, or nearly identical (e.g. differ by one or two bases) as at least one of the ends of another vector component. For example, FIG. 16A shows vector component "AB" that has a free end "b'". This b' free end is non-unique because it is the same as one of the ends on the vector component "BC". In preferred embodiments, each of the free ends of the vector components is only the same as the free end of one other vector component (e.g. b' in FIG. 16A only appears twice).

As used herein, the term "replicable vector" means a vector that is capable of replicating in a host cell.

The term "expression vector" as used herein refers to a recombinant DNA molecule containing a desired coding sequence and appropriate nucleic acid sequences necessary for expression of the operably linked coding sequence (e.g. insert sequence that codes for a product) in a particular host organism. Nucleic acid sequences necessary for expression in prokaryotes usually include a promoter, an operator (optional), and a ribosome binding site, often along with other sequences.

As used herein, the terms "restriction endonucleases" and "restriction enzymes" refer to enzymes (e.g. bacterial), each of which cut double-stranded DNA at or near a specific nucleotide sequence. Examples include, but are not limited to, AvaII, BamHI, EcoRI, HindIII, HincII, NcoI, SmaI, and RsaI.

As used herein, the term "restriction" refers to cleavage of DNA by a restriction enzyme at its restriction site.

As used herein, the term "restriction site" refers to a particular DNA sequence recognized by its cognate restriction endonuclease.

As used herein, the term "purified" or "to purify" refers to the removal of contaminants from a sample. For example, plasmids are grown in bacterial host cells and the plasmids are purified by the removal of host cell proteins, bacterial genomic DNA, and other contaminants. Thus the percent of plasmid DNA is thereby increased in the sample. In the case of nucleic acid sequences, "purify" refers to isolation of the individual nucleic acid sequences from each other.

As used herein, the terms "sequencing" or "DNA sequence analysis" refers to the process of determining the linear order of nucleotides bases in a nucleic acid sequence (e.g. insert sequence) or clone. These units are the C, T, A, and G bases. Generally, to sequence a section of DNA, the sequence of a short flanking region, i.e., a primer binding site, must be known. One method for sequencing is called dideoxy sequencing. One example for performing dideoxy sequencing uses the following reagents: 1) the DNA that will be used as a template (e.g. insert sequence), 2) a primer that corresponds to a known sequence that flanks the unknown sequence, 3) DNA nucleotides, to synthesize and elongate a new DNA strand, 4) dideoxynucleotides that mimic the G, A, T and C building blocks to incorporate into DNA, but that prevent chain elongation, thus acting as termination bases for a DNA polymerase (the four different dideoxynucleotides also may be labeled with different fluorescent dyes for automated DNA sequence analysis), and 5) a nucleic acid polymerizing agent (e.g., DNA polymerase or Taq polymerase, which are enzymes that catalyze synthesis of a DNA strand from another DNA template strand). When these reagents are mixed, the primer aligns with and binds the template at the primer binding site. The polymerizing agent then starts DNA elongation by adding the nucleotide building blocks to the 3' end of the primer. Randomly, a dideoxynucleotide will integrate into a growing chain. When this happens chain elongation stops, and if the dideoxynucleotide is fluorescently labeled, the label will be also be attached to the newly generated DNA strand. Multiple strands are generated from each template, each strand terminating at a different base of the template. Thus, a population is produced with strands of different sizes and different fluorescent labels, depending on the terminal dideoxynucleotide incorporated as the final base. This entire mix may, for example, be loaded onto a DNA sequencing instrument that separates DNA strands based on size and simultaneously uses a laser to detect the fluorescent label on each strand, beginning with the shortest. The sequence of the fluorescent labels, read from the shortest fragment to the longest fragment, corresponds to the sequence of the template. The reading may be done automatically, and the sequence may be captured and analyzed using appropriate software. The term "shotgun cloning" refers to the multi-step process of randomly fragmenting target DNA into smaller pieces and cloning them en masse into plasmid or phage vectors.

The term "shotgun sequencing" refers to sequencing the nucleic acid templates produced in a shotgun cloning reaction.

As used herein, the term "to clone" when used in reference to an insert sequence and vector means ligation of the insert sequence into a vector capable of replicating in a host. The term "to clone" when used in reference to an insert sequence, a vector, and a host cell refers generally to making copies of a given insert sequence. In this regard, to clone a piece of DNA (e.g., insert sequence), one would insert it into a vector (e.g., a plasmid) which may then be put into a host (usually a bacterium) so that the plasmid and insert replicate with the host. An individual bacterium is grown until visible as a single colony on nutrient media, the colony is picked and grown in liquid culture, and the plasmid containing the "cloned" DNA is re-isolated from the bacteria, at which point there will be many millions of copies of the DNA. The term "clone" can also refer either to a bacterium carrying a cloned DNA, or to the cloned DNA itself.

As used herein, the terms "clone bank" or "library" refers to a collection of insert sequences residing in transfected cells, each of which contains a single insert sequence from a cosmid, BAC, virus, genome, or other source, sub-cloned into a vector.

The term "electrophoresis" refers to the use of electrical fields to separate charged biomolecules such as DNA, RNA, and proteins. DNA and RNA carry a net negative charge because of the numerous phosphate groups in their structure. Proteins carry a charge that changes with pH, but becomes negative in the presence of certain chemical detergents. In the process of "gel electrophoresis," biomolecules are put into wells of a solid matrix typically made of an inert porous substance such as agarose. When this gel is placed into a bath and an electrical charge applied across the gel, the biomolecules migrate and separate according to size in proportion to the amount of charge they carry. The biomolecules can be stained for viewing and isolated and purified from the gels for further analysis. Electrophoresis can be used to isolate pure biomolecules from a mixture or to analyze biomolecules (such as for DNA sequencing).

As used herein, the term "PCR" refers to the polymerase chain reaction method of enzymatically amplifying a region of DNA. This exponential amplification procedure is based on repeated cycles of denaturation, oligonucleotide primer annealing, and primer extension by a DNA polymerizing agent such as a thermostable DNA polymerase (e.g. the Taq or Tfl DNA polymerase enzymes isolated from *Thermus aquaticus* or *Thermus flavus*, respectively).

As used herein, the term "dispersed restriction site cloning vector," refers to a vector (e.g. plasmid), or a collection of DNA fragments that may be assembled into a vector, with two or more restriction endonuclease sites intentionally dispersed throughout the sequence of the plasmid so as to be useful for the ligation of multiple independent DNA fragments. A dispersed restriction site cloning vector may exist only as a collection of its individual parts, i.e., the sum of the parts, alone, may in fact not be capable of being maintained as a single entity.

The term "multiplex cloning vector," refers to a vector, or a collection of DNA fragments that may be assembled into a vector, capable of co-cloning more than one independent DNA fragment at more than one cloning site (e.g. restriction site). In preferred embodiments, a multiplex cloning vector is intentionally designed with selectable markers flanked by restriction sites useful for releasing the selectable marker as a functionally intact unit after endonuclease digestion. This design facilitates the selection process for achieving multiple independent DNA fragment inserts at multiple independent insertion sites. A multiplex cloning vector may exist as a collection of its individual parts, i.e., the sum of the parts, alone, may in fact not be capable of being maintained as a single entity.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'" Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "primer" refers to an oligonucleotide, whether occurring naturally as in a purified restriction digest or produced synthetically, which is capable of acting as a point of initiation of nucleic acid synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucieotide. The primer must be sufficiently long to prime the synthesis of extension products in the presence of the inducing agent. The exact lengths of the primers will depend on many factors, including temperature, source of primer and the use of the method.

As used herein, the term "target," in regards to PCR, refers to the region of nucleic acid bounded by the primers. Thus, the "target" is sought to be sorted out from other nucleic acid sequences. A "segment" is defined as a region of nucleic acid within the target sequence.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "transformation" or "transfection" as used herein refers to the introduction of foreign DNA into cells (e.g. prokaryotic cells). Transformation may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "vector component" refers to any linear nucleic acid sequence that is capable of forming part of a circular vector when combined with at least one other vector component (e.g. in the presence of multiple insert sequences), or when combined with at least one insert sequence (e.g. SEQ ID NO:85). In preferred embodiments, a vector component comprises at least one selectable marker sequence or other features (e.g. sticky ends for the formation of a circular vector w hen combined other vector components or insert fragments, primer binding sites, transcriptional terminators, etc), which contribute to the maintenance or function of the resulting circular vector.

As used herein, the term "comprising free ends" or "having free ends" in reference to a double stranded nucleic acid molecule having blunt ends, indicates that the nucleic acid molecule is linear (the ends are not bound to additional nucleotides), with each "free end" being the position occupied by the terminal 5' and 3' bases of the nucleic acid molecule that are hybridized to each other. A linear, double stranded, blunt ended nucleic acid molecule will have two "free ends" (referred to as "blunt free ends"). As used herein, the term "free ends" in reference to a double stranded nucleic acid molecule having overhang (sticky) ends, indicates that the nucleic acid molecule is linear (the ends are not bound to additional nucleotides), with each "free end" being the positions occupied by the single stranded (overhang) region. A linear, double stranded, sticky-ended nucleic acid molecule will have two "free ends" (referred to as "sticky free ends"). Also, a double stranded, linear nucleic acid molecule may also have one "blunt free end" and one "sticky free end". Also, when a vector component or insert sequence is said to have "free ends," this indicates, for double stranded vector components and insert sequences, that the molecule is linear and that the terminal 3' base, and the terminal 5' base at each end of the molecule are not bound to other oligonucleotides.

As used herein, the term "source nucleic acid molecule" refers to any nucleic acid sequence, either linear or closed circular, that is capable of supplying at least one vector component. For example, a source nucleic acid molecule may itself be a vector component, or may become a vector component upon digestion with restriction enzymes, or may serve as a target sequences such that a portion of the source nucleic acid molecule may be subject to PCR to create a vector component. As used herein, the term "separate" in reference to at least two source nucleic acid molecules" indicates that the at least two source nucleic acid molecules are not physically linked (e.g. ligated) together, and do not have the same nucleic acid sequence. In other words, the at least two source nucleic acid molecules are separate molecules that have different nucleic acid sequences.

As used herein, the phrase "wherein said vector components are non-contiguous within said circular vector" refers to the arrangement of vector components within a circular vector such that there is at least one insert sequence between the ends of each vector component present on the circular vector, such that none of the ends of vector components are joined (e.g. ligated) together.

As used herein, the term "selective growth media" refers to growth media used to grow cells that has been supplemented with one or more selective agents (antibiotics).

As used herein, the term "non-promoter sequence" refers to any nucleic acid sequence that is unable to serve as an operable promoter element for initiating transcription in a given host cell, such as a bacterial host cell, or a eukaryotic host cell. In preferred embodiments, the host cell in which the non-promoter sequence is unable to serve as an operable promoter is an E. coli host cell.

As used herein, the phrase "wherein said identifying is at least 95% accurate" refers to the visual, chemical, mechanical, or biological identification of cells (or colonies of cells) as containing the desired number insert sequences, wherein this identification is correct 95% of the time (e.g. only 5% or less identified as containing the desired number of insert sequences are false positives). The "95%" in this phrase may be substituted for other numbers (e.g. 80%, 90%, 98%, 99%, etc.), to indicate the percent correct.

As used herein, the term "multiplex sequencing reagents," includes, but is not limited to, appropriate primers, DNA nucleotides, dideoxynucleotides, and a DNA polymerizing agent (e.g. Taq polymerase). In some embodiments, the four different dideoxynucleotides are labeled with different fluorescent dyes (e.g., for automated DNA sequence analysis).

As used herein, the phrase "wherein each of said vector components is flanked by cloning sites" means that each of the vector components to be made into a vector (e.g. circular vector) when the circular vector is formed, has cloning sites at each of its two ends (e.g. the cloning sites may be part of the vector component, or only be formed when joined to another vector component, such that each vector component has a cloning site at each of its ends).

As used herein, the symbol "X" is a number that is a positive integer greater than or equal to one.

DESCRIPTION OF THE INVENTION

The present invention relates to systems, methods, and compositions for cloning and sequencing insert nucleic acid sequences. In particular, the present invention provides vectors and vector components configured for multiplex cloning and multiplex sequencing. The present invention also provides vectors and vector components configured to reduce transcription of insert sequences.

In some embodiments, the present invention provides systems, methods, and compositions for cloning multiple insert sequences in a single vector. In particular embodiments, this vector is formed from at least two vector components containing selectable marker sequences and at least two insert DNA sequences. The formation of this vector may occur, for example, in a single ligation reaction (e.g. the two vector components and insert sequences, all separate, are joined together in a single ligation reaction). In some embodiments, the compositions of the present invention permit multiplex sequencing (e.g. from a single vector constructed from at least two vector components and at least two insert sequences). In preferred embodiments, the source nucleic acid used to form the vectors of the present invention are at least two separate source nucleic acid molecules (e.g. neither of which has all of the selectable markers as the final vector that is formed).

The present invention provides systems that facilitate multiplex DNA cloning and sequencing. In these systems, multiple DNA fragments are simultaneously and independently cloned into dispersed sites of a cloning vector, and in some embodiments, the fragments are subsequently sequenced simultaneously in a single DNA sequencing reaction. This multiplex cloning system encompasses a very low-background direct selection vector and requisite exogenous selectable DNA fragments, as well as enzymatic and physical processing of said vector and selectable fragments. This invention further provides prokaryotic host cells, cell lines and methods for processing of these cells for transformation by the cloning vectors of the present invention. The present invention also provides methods of simultaneously sequencing multiple cloned DNA fragments.

The present invention provides systems and methods for multiplex DNA cloning and sequencing. For example, the systems and methods of the present invention allow multiple insert sequences to be simultaneously and independently cloned into dispersed sites of a cloning vector, and allows the insert sequences to be subsequently sequenced simultaneously in a single DNA sequencing reaction. This multiplex cloning system, in some embodiments, has a very low background signal. The invention also provides multiplex cloning vector preparations with a background of less than 0.5% empty vector. The invention further provides methods for making multiplex cloning vector preparations with at least 99.5% recombinant insertion frequency at each restriction site and a background of less than 0.5% empty vector.

Commonly used cloning vectors are designed with one or more restriction sites clustered in one small region of the vector (FIG. 1A). This polylinker design usually limits the number of DNA fragment insertion sites to one per vector. As described above, it is possible to clone more than one fragment into the same site, but no advantage is gained for sequencing purposes, as there are only two flanking primer extension sites and sequence reads are generally limited to approximately 500–700 bases.

Nearly all of the commonly used vectors are designed such that the restriction sites suitable for cloning are located within the reading frame of a selectable marker or indicator gene. The polylinker engineered into the lacZα gene, or any of numerous other endogenous or engineered restriction sites in any antibiotic resistance gene, exemplify the predominant cloning strategy in use today.

The central dogma of cloning as it is practiced today is that one plasmid vector can propagate one DNA fragment for genomic sequence analysis. Because of the very large number of plasmid purification reactions needed to sustain genomic scale sequencing, the need exists for a method that can reduce the number of templates required for this process. True multiplex cloning vectors and systems capable of propagating multiple independent DNA fragments at multiple different sites within a single vector molecule are provided by the present invention. The benefits of the present invention, for example, are demonstrated from the following example: purifying two co-cloned DNA fragments carried by a single vector molecule is approximately twice as efficient as the current methods of purifying two separate vectors, each carrying one cloned fragment. Similarly, a quadraplex cloning vector, for example, could improve the template purification rate approximately four-fold compared to purifying four single-fragment cloning vectors. When applied to a large-scale sequencing effort (e.g. sequencing more than 10,000 templates per day), the advantages of multiple cloning and sequencing become extraordinary.

The multiplex cloning vectors of the present invention also lend themselves to a simple multiplex sequencing strategy, realizing additional advantages. Each of the unique primer binding sites in a multiplex vector has an associated unique capture sequence for affinity purification. In one embodiment of the present invention, a sextuplex sequencing scheme is carried out, in which all six primers cognate to a triplex cloning vector are added to the same reaction tube. All six sets of sequencing reactions are conducted in a single tube, extending the concept demonstrated by Creasey et al. (BioTechniques 11: 102 [1991]) and Wiemann et al. (Anal. Biochem. 224: 117 [1995]; Anal. Biochem. 234: 166 [1996]). To separate the six sequence ladders, biotin tagged peptide nucleic acid (PNA) oligomers, each specific for one of the unique capture sequences, are sequentially added to the reaction pool and removed by binding to streptavidin-coated magnetic particles. Each affinity purified reaction is analyzed on an automated DNA sequencing machine.

In a preferred embodiment, PNA oligomers are used instead of DNA oligomers because of their inherently higher affinity for DNA, even in low salt conditions (Egholm et al., Nature 365: 566 [1993]), which allows the use of shorter capture oligomers and permits higher capture efficiencies than equivalent DNA oligomers. Because the streptavidin-biotin-PNA particles can be reused 5–10 times, just as with the DNA equivalent, the additional reagent cost for this affinity purification scheme is minimal. The biotin-streptavidin purification step does increase the reagent costs slightly, but also serves to remove contaminating dye terminators, template DNA, and polymerase. This last point is particularly important as the newest generation of 96 capillary sequencing instruments are integrated into high throughput genome centers. The small bore of capillary based instruments (50 micron diameter) makes this system especially prone to failure by macromolecular contaminants, which readily occlude the injection interface.

As discussed previously, the present invention overcomes many of the problems associated with the current blue screen technology. One such problem with the blue screen technology is plasmid instability due to vector-driven transcription of the insert DNA. The lac promoter that drives transcription of the lacZ α-peptide in pUC type plasmids must be active (either constitutively or through induction, e.g., by IPTG) for the blue screen to function. Because insert DNA fragments are cloned into the lacZ α-peptide, the lac promoter will cause transcription of the inserted sequences as well. Consequently, recombinant proteins or peptides encoded by the insert sequences may be expressed. Clones that encode proteins or peptides that are toxic or deleterious to the host bacterium may result in death or slow growth of the host, likewise leading to difficulty in recovering such fragments. The present invention addresses the problem of promoter driven transcription of insert sequences, for example, by eliminating promoter elements near cloning sites, and providing terminators after selectable markers, which is made possible by the systems and methods of the present invention.

Another problem with cloning insert sequences is that transcription may be initiated from within the cloned insert DNA, particularly if the insert contains authentic transcriptional promoters or regions that behave as promoters in bacteria. In most conventional cloning vectors, including the pUC type vectors, such insert-driven transcription may proceed unimpeded into the vector portion of the plasmid. This transcription may interfere with transcription of the antibiotic resistance gene(s) encoded by the vector or with the functionality of the origin of replication. Either type of interference is likely to cause instability of the recombinant clone, leading to difficulty in cloning such fragments. In particular, inserts that are high in A-T content (e.g., more than 60% of the bases are either A or T) have an increased tendency to behave as bacterial promoters. The genomic DNA of several organisms that are highly enriched in A-T content are difficult to clone (e.g., Lactobacillus, Dictyostelium, Oxytricha, Tetrahymena, Paramecium). The present invention blocks or minimizes insert transcription, for example, by providing transcriptional terminators before and after insert sequences in vectors formed from the vector components of the present invention.

In certain embodiments, the present invention provides compositions comprising a vector component, wherein the vector component comprises: i) first and second free ends; ii) a selectable marker region, iii) a first transcriptional terminator between the first free end and the selectable marker region, and iv) a second transcriptional terminator between the second free end and the selectable marker region, and wherein the vector component is configured to form a circular vector when combined with an insert sequence. In certain embodiments, the insert sequence has at least 65% A/T content (e.g. at least 65%, 75%, 80%, or 85% A/T content).

High copy number of vectors with toxic or lethal inserts may also promote cell death, and thus, the lack of the ability to recover the sequence of the deleterious or toxic sequence from the host cell. Most cloning vectors in use today employ a derivative of the ColE1 origin of replication that is present in the pUC vectors. This origin of replication results in a high copy number (typically 300–500 copies) of the plasmid in which it is contained. Plasmid replication to high copy numbers is advantageous for recovery of increased amounts of plasmid DNA from cell cultures or for increased production of recombinant proteins encoded by such plasmids. However, plasmids that contain DNA that is deleterious to the host cell may result in slow growth or death of the cell if they are present at high copy number; hence, they may be difficult to clone in a high copy number vector. The present invention, in some embodiments, further minimizes the deleterious effects of toxic insert sequences by employing vectors and vector components configured to have a low copy number in a host cell.

As mentioned above, the present invention also provides vectors and vector components that minimize insert sequence transcription (e.g. minimize vector-driven transcription into the insert DNA and insert-driven transcription into the vector). In preferred embodiments, the reduced amount of transcription allows cloning of sequences that are toxic to the host cells (thereby allowing the sequence to be cloned when otherwise the host cell would be killed and the sequence could not be cloned). In certain embodiments, the present invention provides compositions comprising a vector component, wherein the vector component comprises: i) a selectable marker region, ii) a transcriptional terminator after the selectable marker region, and wherein the vector component is configured to form a circular vector when combined with an insert sequence. In preferred embodiments, the vector is capable of maintaining an insert sequence that is a lethal or toxic insert sequence (e.g. will not allow the host cell to form a colony if the insert sequence is transcribed). In certain embodiments, the insert sequence has at least 65% A/T content (e.g. at least 65%, 75%, 80%, or 85%; A/T content).

One problem with the ampicillin gene product beta-lactamase, found in all of the pUC series of blue screen plasmids, also contributes to the problem of false positives. Beta-lactamase can leak out of the cell to generate an antibiotic free zone surrounding the ampicillin resistant colony. This antibiotic free zone enables the growth of so called "feeder cells," which do not have a plasmid but are nonetheless capable of growing in the vicinity of ampicillin resistant colonies. These cells will be white in a blue screen system, and they are readily confused as being recombinant clones. False negative or false positive results are, in general, present with any cloning system. The degree to which a cloning strategy circumvents these issues will impact the final desired result. The present invention addresses this problem, for example, by providing a mutated ampicillin resistance sequence configured to reduce feeder colonies. In some embodiments, the mutated ampicillin resistance gene (e.g. derived from pUC19) comprises at least one mutation selected from: T to A at position 174; T to C at position 333; A to G at position 412, C to T at position 648; T to C at position 668; T to C at position 764; and combinations thereof. In preferred embodiments, the circular vector is a recombinant plasmid. In some embodiments, the native promoter of the ampicillin resistance gene is replaced with a less active promoter (e.g. chloramphenicol promoter).

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar): μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); DS (dextran sulfate); C. (degrees Centigrade); and Sigma (Sigma Chemical Co., St. Louis, Mo.).

In the experimental disclosure which follows, the following reagents and protocols were used:

Enzymes

AvaII, BamHI, EcoRI, HindIII, HincII, NcoI, SmaI, RsaI, T4 DNA ligase, T4 DNA polymerase, Vent DNA polymerase, and T4 polynucleotide kinase were obtained from New England Biolabs (Beverly, Mass.). Where indicated T4 DNA ligase was obtained from Epicenter Technologies (Madison, Wis.). Taq and Tft DNA polymerase and calf intestinal phosphatase were obtained from Promega (Madison, Wis.). Calf intestinal alkaline phosphatase and thermosensitive alkaline phosphatase was obtained from Life Technologies (Rockville, Md.). Enzymatic reactions were performed according to the manufacturers' instructions.

Media

Terrific Broth (TB) medium contained Bacto tryptone (11.8 g 1-1), yeast extract (23.6 g 1-1), dipotassium hydrogen phosphate (9.4 g 1-1) and potassium dihydrogen phosphate (2.2 g 1-1). TY plates contained Bacto tryptone (8 g 1-1), yeast extract (5 g 1-1), NaCl (5 g 1-1), and agar (15 g 1-1). Plates were supplemented with ampicillin or carbenicillin at 100 ug/ml, chloramphenicol at 10 ug/ml, kanamycin at 20 ug/ml, or gentamycin at 15 ug/ml. Media components and antibiotics were obtained from Sigma (St. Louis, Mo.).

Strains, Plasmids, and Bacteriophage DNA

Plasmid pZErO-2 is commercially available from Invitrogen Corp. (Carlsbad, Calif.). Plasmid pACYC184 is available from the American Type Culture Collection, #37033 (Chang A C and Cohen S N, J. Bacteriol. 134: 1141–1156, 1978; Rose R E, Nucleic Acids Res. 16: 355, 1988). pACYC177 is available from the American Type Culture Collection. #37031 (Chang A C and Cohen S N, supra; Rose R E, supra, pUC19 is available from the American Type Culture Collection, #37254 (Vieira J and Messing J, Gene 19: 259–268, 1982. Bacteriophage fd is available from the American Type Culture Collection, #15669-B2 (Hoffmann-Berling H, Virology 22: 305, 1964). pJQ200 is available from the American Type Culture Collection, #77482 (Quandt J and Hynes M F, Gene 127:15–21, 1993). The cell strain *E. coli* BHB2600, supE, supF, lambdaCH616, is available from the American Type Culture Collection, #47004 (Geider K et al.,Gene 33: 341–349, 1985). *E. coli* DH5αF', F' φ80dlacZ Δ(lacZYA-argF)U169 (deoR recA1 endA1 hsdR17(r.sub.k.sup.- m.sub.k.sup.+) phoA supE44 .lambda..sup.- thi-1 gyrA96 relA1 was obtained from Life Technologies (Rockville, Md.). *E. coli* DH5αFT, F' φ80dlacZ. Δ (lacZYA-argF)U169 (deoR recA1 endA1 hsdR17(r.sub.k.sup.- m.sub.k.sup.+) phoA supE44 .lambda..sup.- thi-1 gyrA96 relA1/F' proAB.sup.+ lacI.sup.qZ.deltaM15 Tn10(tet.sup.r) was obtained from Life Technologies (Rockville, Md.). *E. coli* DH5αF'IQ, F' φ80dlacZ Δ (lacZYA-argF)U169 dcoR recA1 endA1 hsdR17(r.sub.k.sup.- m.sub.k.sup.+) phoA supE44 lambda.sup.- thi-1 gyrA96 relA1/F' proAB.sup.+ lacI.sup.qZ.delta.M15 zzf::Tn5[Km.sup.r] was obtained from Life Technologies (Rockville, Md.). *E. coli* DH10B, F'.sup. mcrA Δ (mrr-hsdRMS-mcrBC) φ80dlacZ Δ M15 Δ lacX74 (deoR recA1 endA1 araD139 Δ (ara, leu)7697 galU galK lambda.sup.- rpsL nupG was obtained from Life Technologies. Bacteriophage T7 DNA was purchased from Sigma (St. Louis, Mo.) and bacteriophage lambda DNA was obtained from Promega Corporation (Madison, Wis.).

Plasmid Purification

Mini-prep, midi-prep, and large-scale plasmid DNA was purified by the alkaline lysis method (3) or with the Quantum Prep Kit (Bio-Rad Laboratories, Hercules, Calif.).

PCR Reactions

Taq or Tfl PCR reactions were performed in 50–100 μl of 1× Taq or Tfl polymerase buffer with 200 pmol each primer, 100 nM dNTP, approx. 10 ng template DNA, and 2.5 units of Taq or Tfl DNA polymerase. PCR cycle conditions were 30 seconds at 94 degrees C., 30 seconds at 60 degrees C., 2 minutes at 72 degrees C. for 30–35 cycles, followed by 10 minutes at 72 degrees C.

Vent PCR reactions were performed in 50–100 μl of 1× Vent polymerase buffer with 200 pmol each primer, 100 nM dNNTP, approx. 10–50 ng template DNA, and 2.5 units of Vent DNA polymerase. PCR cycle conditions were 15 seconds at 94 degrees C. 15 seconds at 50 degrees C., 2 minutes at 72 degrees C. for 25–30 cycles, followed by 10 minutes at 72 degrees C.

Sequencing Reactions and Analysis

The Prism Big Dye Terminator Cycle Sequencing Kit with AmpliTaq DNA Polymerase, FS, and the Prism 310 Genetic Analyzer capillary sequencing instrument were obtained from Applied Biosystems (Foster City, Calif.). The cycle sequencing reactions were performed in 10 μl of ½× buffer with 250 ng plasmid template and 3.2 picomole of oligonucleotide primer. Cycle sequencing conditions were 10 seconds at 95 degrees C., 5 seconds at 50 degrees C., 4 minutes at 60 degrees C. for 25 cycles. The reactions were purified by Sephadex G-50 centrifugal filtration for 2 minutes at 3,000 RPM. The eluate was dried at 75 degrees C. and resuspended in 25 μl formamide. This mixture was heated at 95 degrees C. for 2 minutes and placed on the auto-loading tray of the sequencing instrument for injection, electrophoresis, detection, and automated base calling.

Lipation Reactions

The ligation reactions were performed in 10 μl of 1× buffer containing DNA, 0.5 mM ATP, and 2–10 units T4 DNA ligase for 2–3 hours at room temperature. Ligation reactions were then heat-treated at 65° C. for 15 minutes to denature the ligase.

For the examples shown below, three separate ligation reactions were prepared as follows: 1) A "no ligase, no insert" control reaction to test for the level of contaminating empty vector; 2) A "plus ligase, no insert" control reaction to check for the efficiency of 5' phosphate removal; and 3) A "plus ligase, plus insert" reaction to test the cloning efficiency. The insert in this control is phage lambda DNA digested with RsaI (λ RsaI) or HincII (λHincII).

Transformation Procedure

Frozen electroporation competent *E. coli* cells were thawed, and 50 μl were combined with 1–2 μl of ligated, heat-treated DNA. This mixture was added to a chilled 0.1 cm gap electroporation cuvette. Electroporation using the Bio-Rad (Hercules, Calif.) E. coli Pulsor™ apparatus was at 1.8 kV. The cells were transferred to 950 µl of TB medium and placed in a shaking incubator at 225 rpm for 1 hour at 37° C. Varying amounts of these cells were spread on TY plates containing the appropriate concentration of antibiotic or indicator chemicals and incubated overnight at 37 C.

Transformation Results

The efficiency of the competent cells was determined by transformation with supercoiled plasmid pUC19. Typically, 10 pg of pUC19 was mixed with the competent cells, electroporated, and brought up to 1 ml in growth media for recovery at 37 C. for 1 hr. This solution was diluted ten fold, and a $\frac{1}{10}^{th}$ aliquot was spread on TY plates containing ampicillin. The number of colonies was counted to calculate the efficiency in colony forming units (CFU)/ug pUC19. The efficiency of the electro-competent cells used in the following examples ranged from $5 \times 10^8$–$5 \times 10^9$ colony forming units/ug pUC19.

Although transformation efficiencies are typically presented in terms of transformants per microgram of a supercoiled vector, these values are not directly applicable when comparing vectors of different sizes. To compensate for different sizes, a more accurate value is the number of transformants per femtomole of vector. However, because of the unknown size of inserts in a particular recombinant clone, and the large variation in the amount of DNA used between experiments, the transformation results from the cloning experiments are presented as the number of colonies per ml transformed cells. Thus, the number of colonies are counted and divided by the fraction of cells from the original 1 ml of recovery media. The amount of DNA used in a particular ligation and the fraction of the ligation used to transform the competent cells is also reported. Using this method of calculation, a transformation efficiency of $1 \times 10^9$ CFU/ug of pUC19 corresponds to approximately 10,000 colonies/ml of cells transformed with 10 pg of pUC19.

Nucleic Acid Sequences

In order to minimize extraneous sequence elements, in some examples, individual selectable markers were removed from their original context via polymerase chain reaction amplification.

PCR primers were designed to amplify a plasmid origin of replication (Ori) and four antibiotic resistance genes: ampicillin (Amp), chloramphenicol (Cam), kanamycin (Kan), and gentamycin (Gen). The PCR primers were designed to append a SmaI site to the 5' and 3' end of each selectable marker. The primer corresponding to the 5' end of each marker also contained a unique eight base restriction site, and primer corresponding to the 3' end of each antibiotic gene contained a strong transcriptional terminator. SmaI recognizes the sequence CCCGGG and cleaves between the C and G to leave blunt ends. The selectable markers were amplified from various plasmid sources, restricted with SmaI, ligated to one another or to other known plasmids, and transformed into E. coli cells. All five PCR fragments were checked for their respective biological function, associated restriction sites, and size.

The test insert DNA used throughout the Example was bacteriophage lambda (λ) DNA restricted to completion with RsaI (113 fragments) or with HincII (35 fragments). RsaI recognizes the sequence GTAC and cleaves between the T and A to leave blunt ends. HincII recognizes the sequence GT(T/C)(A/G)AC and cleaves between the (T/C) and (A/G) to leave blunt ends. The λHincII DNA was precipitated with PEG8000/MgCl$_2$, which results in loss of fragments less than approximately 300 bp in length. In the examples below, λ fragments were present at approximately 3–4 fold molar excess of DNA ends over the selectable marker fragments.

EXAMPLE 1

Conventional Cloning with a Blue Screen Vector

Blue screen cloning with the vector pUC19 is commonly used for cloning experiments, including the construction of template libraries for genomic sequencing. The blue screen vector pUC19, shown schematically in FIG. 1A, was restricted with SmaI and treated with alkaline phosphatase (AP) to remove the 5' terminal phosphate groups (pUC19 SmaI/AP). Since ligase requires a 5' phosphate group on at least one of the DNA termini in a ligation reaction, removal of the 5' phosphates of the vector inhibits rejoining of the ends of the vector. This type of dephosphiorylation is commonly used to decrease the vector background in cloning strategies. Three separate ligation reactions were prepared as follows: 1) A no ligase, no insert control reaction to test for the level of undigested, empty vector background (pUC19/SmaI/AP–ligase); 2) A plus ligase, no insert control reaction to check for the efficiency of 5' phosphate removal (pUC19/SmaI/AP+ligase); and 3) A plus ligase, plus insert reaction to test the cloning efficiency of this vector system (pUC19/SmaI/AP+λRsaI+ligase). The ligation reaction contained 130 ng pUC19 SmaI/AP and approximately one fifth of this reaction was transformed into E. coli DH5αF'. An aliquot of the transformed cells was spread onto TY agar plates containing ampicillin plus XGAL. The transformation results are presented in Table 1.

TABLE 1

Efficiency of blue screen cloning

| Ligation reaction | Antibiotic plate | Blue colonies ml transformed cells | White colonies ml transformed cells |
|---|---|---|---|
| pUC19/SmaI/AP – ligase | amp + XGAL | 667,000 | 0 |
| pUC19/SmaI/AP + ligase | amp + XGAL | 40,000 | 3,300 |
| pUC19/SmaI/AP + λRsaI + ligase | amp + XGAL | 43,000 | 53,000 |

The pUC19/SmaI/AP–ligase control reaction resulted in a high background of colonies in the absence of ligase. As expected, the colonies resulting from this reaction had a blue phenotype. The pUC19/SmaI/AP+ligase reaction also produced a large number of colonies in the absence of insert DNA. Approximately 8% (3300/[3300+40,000]×100) of the resulting colonies had a white phenotype, indicating disruption of the lacZα gene even in the absence of insert DNA. In the presence of insert DNA, this cloning experiment resulted in approximately 53,000 white colonies, or putative recombinant clones, per ml of transformed cell (pUC19/SmaI/AP+λRsaI+ligase). The background of true negative clones, i.e., the ratio of empty vector to putative recombinants, was approximately 54.9% ([43,000/[43000+53000×100). The frequency of putative false positive clones, i.e., white colonies obtained in the absence of insert DNA was approximately 6.2% (3300/53,000×100). This high level of empty vector background and high frequency of false positives is a common problem when using the blue screen system to clone blunt-ended fragments.

EXAMPLE 2

Standard Direct Selection Cloning

This example describes a standard direct selection cloning procedure. The pZErO-2 cloning vector, commercially available from Invitrogen (catalog number K2600-01, Carlsbad, Calif.), allows direct selection of inserts via disruption of the lethal gene ccdB. The CcdB protein acts by inhibiting the essential enzyme topoisomerase II (DNA gyrase) of the host bacteria. The ccdB gene is fused in-frame to the C-terminus of the lacZα gene in the pZErO construct, putting it under control of the lac promoter. Thus, the chemical IPTG is required to induce its expression in cells that carry the once-expressing lacI$^4$ allele of the lac repressor.

pZErO-2 was restricted with SmaI and treated with alkaline phosphatase. Three separate ligation reactions were prepared as follows: 1) A no ligase, no insert control reaction to test for the level of uncut empty vector (pZErO-2/SmaI/AP–ligase); 2) A plus ligase, no insert control reaction to check for the efficiency of 5' phosphate removal (pZErO-2/SmaI/AP+ligase); and 3) A plus ligase, plus insert reaction to test the cloning efficiency (pZErO-2/SmaI/AP+λRsaI+ligase). The ligation reaction contained 10 ng pZErO-2 SmaI/AP. 1/20 of this reaction was transformed into *E. coli* DH5αF', and an aliquot was spread on TY agar plates containing kanamycin plus or minus IPTG. The transformation results are presented in Table 2.

TABLE 2

Efficiency of direct selection cloning with pZErO-2

| Ligation rx | Antibiotic plate | # colonies/ml transformed cells |
|---|---|---|
| pZErO-2/SmaI/AP − ligase | kan | 10,000 |
| pZErO-2/SmaI/AP + ligase | kan | >200,000 |
| pZErO-2/SmaI/AP + λRsaI + ligase | kan | >200,000 |
| pZErO-2/SmaI/AP − ligase | kan + IPTG | 0 |
| pZErO-2/SmaI/AP + ligase | kan + IPTG | 3245 |
| pZErO-2/SmaI/AP + λRsaI + ligase | kan + IPTG | 88,600 |

As seen in Table 2, the pZErO-2/SmaI/AP–ligase and pZErO-2/SmaI/AP+ligase control reactions produced very high backgrounds of colonies when plated on kan minus IPTG plates. This result is expected and demonstrates that it is essential to include the chemical inducer IPTG when using this vector. When plated on kan plus IPTG plates, the pZErO-2/SmaI/AP–ligase control reaction did not produce a background of colonies. However, the pZErO-2/SmaI/AP+ligase reaction resulted in approx. 3200 colonies in the absence of insert DNA. In the presence of insert DNA, 88,600 colonies were observed (pZErO-2/SmaI/AP+λRsaI+ligase). Thus, the background of empty vector to putative recombinants was approximately 3.7% (3002/88600×100). The frequency of false positive or false negative results using this system cannot be estimated without significant additional analysis.

EXAMPLE 3

Multiplex Cloning Using Standard Methods

Figure 2:
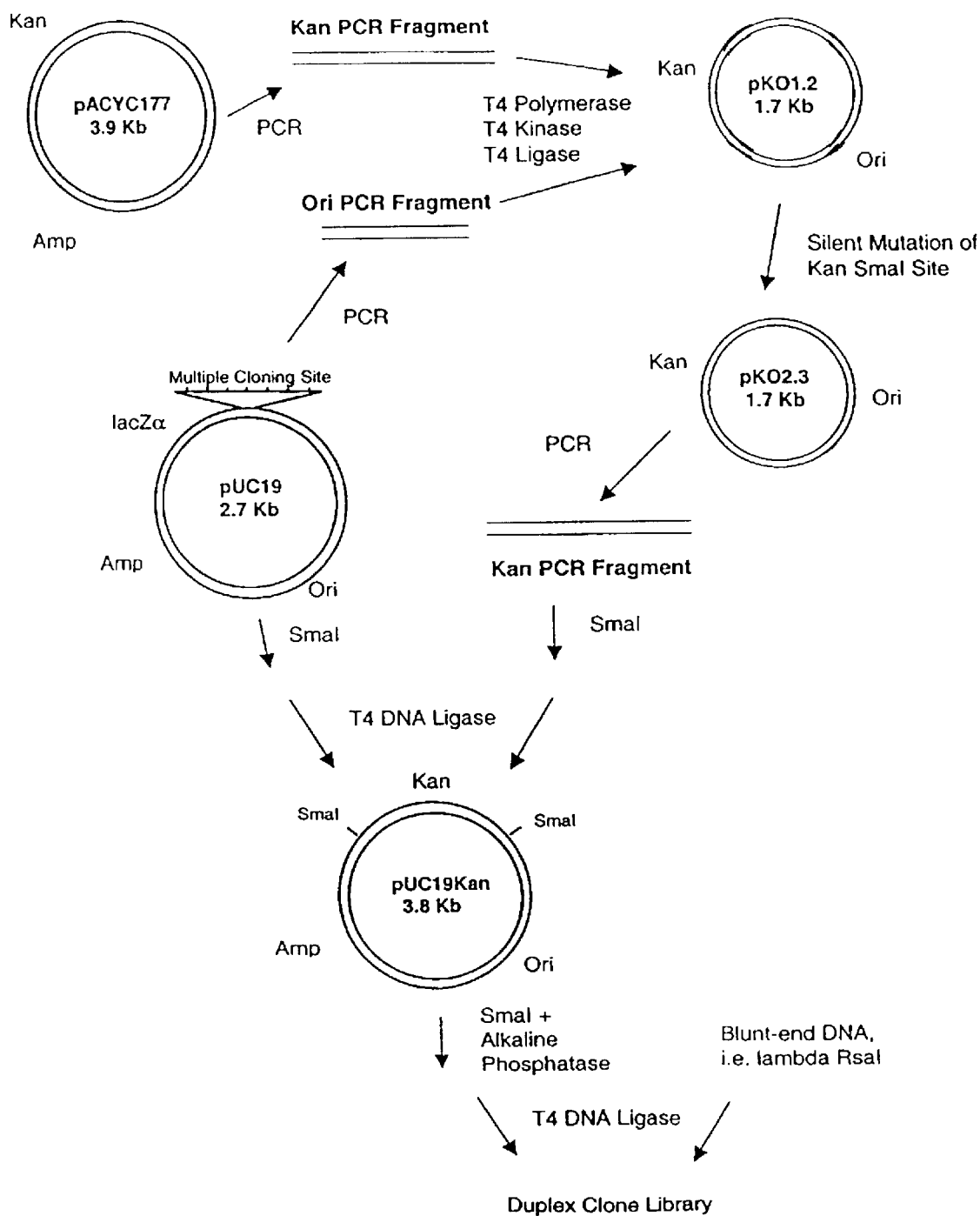
FIG. 2 shows a schematic diagram illustrating the construction of a duplex cloning vector (pUC19Kan is shown) and a duplex shotgun cloning library. The hash marks indicate restriction sites.

The quadraplex cloning concept illustrated in FIG. 1B shows a plasmid vector with multiple selectable markers separated by the restriction enzyme SmaI. Using this same model, a duplex cloning system using conventional vector fragments and processing methods was tested. FIG. 2 shows construction of the duplex cloning vector pUC19Kan, created from pUC19 restricted with SmaI and a kanamycin selectable marker with SmaI restricted ends. The kanamycin gene was initially amplified from pACYC177 using the flanking oligonucleotide primers KML.2 (5'-CAC TGT TAA CCC GGG TTT AAA CGT TGT GTC TCA AAA TAT CTG ATG T-3', SEQ ID NO:1) and KMR2 (5'-CAC TGT TCC CGG GAG TCA AAA GCC TCC GG T CGG AGG CTT TTG ACT TTC TGC TTA GAA AAA CTC ATC GAG CAT CAA ATG-3', SEQ ID NO:2) to generate the plasmid pKO1.2. The kan gene in pKO1.2 was modified to silently mutate an internal SmaI site and add a tonB transcriptional terminator (Reynolds et al. J. Mol. Biol., 224:31 [1992]) to the 3' end of the gene, using the PCR primers KDSL2: TGG GAT CGC AGT GGT GAG TAA CCA TGC ATC A (SEQ ID NO:27) and KDSR2: GGG AAA ACA GCA TTC CAG GTA TTA GAA (SEQ ID NO:28). The resulting plasmid was designated pKO2.3. The primers KML2 and KMR2 were then used to amplify the kanamycin gene from the plasmid pKO2.3.

The vector pUC19Kan was restricted with SmaI and treated with alkaline phosphatase to generate two separate selectable markers from one vector (note that Ori was not tested as a selectable marker in this Example). A duplex cloning experiment was set up with 3 separate reactions as follows: 1) A no ligase, no insert control reaction to test for the level of uncut empty vector background (pUC19Kan/SmaI/AP–ligase); 2) A plus ligase, no insert control reaction to check for the efficiency of 5' phosphate removal (pUC19Kan/SmaI/AP+ligase); 3) A plus ligase, plus insert reaction to test the overall efficiency of duplex cloning (pUC19Kan/SmaI/AP+λRsaI+ligase). The ligation reaction contained 130 ng pUC19Kan/SmaI/AP. One tenth of this reaction was transformed into *E. coli* DH5αFT, and an aliquot was spread onto TY agar plates containing ampicillin plus kanamycin. The transformation results are presented in Table 3.

TABLE 3

Efficiency of duplex cloning using the pUC19Kan vector preparation

| Ligation rx | Antibiotic plate | # colonies/ml transformed cells |
|---|---|---|
| pUC19Kan/SmaI/AP − ligase | amp + kan | 49,000 |
| pUC19Kan/SmaI/AP + ligase | amp + kan | 21,000 |
| pUC19Kan/SmaI/AP + λRsaI + ligase | amp + kan | 75,000 |

The pUC19Kan/SmaI/AP–ligase control reaction resulted in a significantly high background of transformants (approx. 49,000 colonies). The plus ligase reaction also resulted in a large number of colonies (approx. 21,000) in the absence of insert DNA. This duplex cloning experiment resulted in approximately 75,000 putative recombinant clones (pUC19Kan/SmaI/AP+λRsaI+ligase). The frequency of empty vector versus ligation events containing insert DNA was 28% (21000/75000×100). It is not uncommon to find such a high level of empty vector background using conventional cloning vectors.

EXAMPLE 4

Multiplex Cloning with Partial Source Nucleic Acid

This Example describes multiplex cloning with partial source nucleic acid. In particular, to reduce the background due to denatured plasmid DNA the two selectable markers are purified from different plasmid 'partial sources' and combined in one ligation reaction (as opposed to obtaining the two selectable markers from a single plasmid backbone containing both selectable markers, e.g., pUC19Kan in Example 3). Because neither source contains both selectable markers (i.e. both sources are 'partial sources'), intact partial source DNA in the ligation and transformation reaction is selected against under dual selection. Multiplex cloning reactions with three combinations of partial source DNA were tested. The first is the combination of two different plasmids, with different selectable markers, which have been processed for ligation and cloning. The second is the combination of selectable marker fragments amplified by PCR from two separate vector backbones. The third combination is a plasmid with one selectable marker and a PCR amplified selectable marker from a separate vector.

Figure 3:
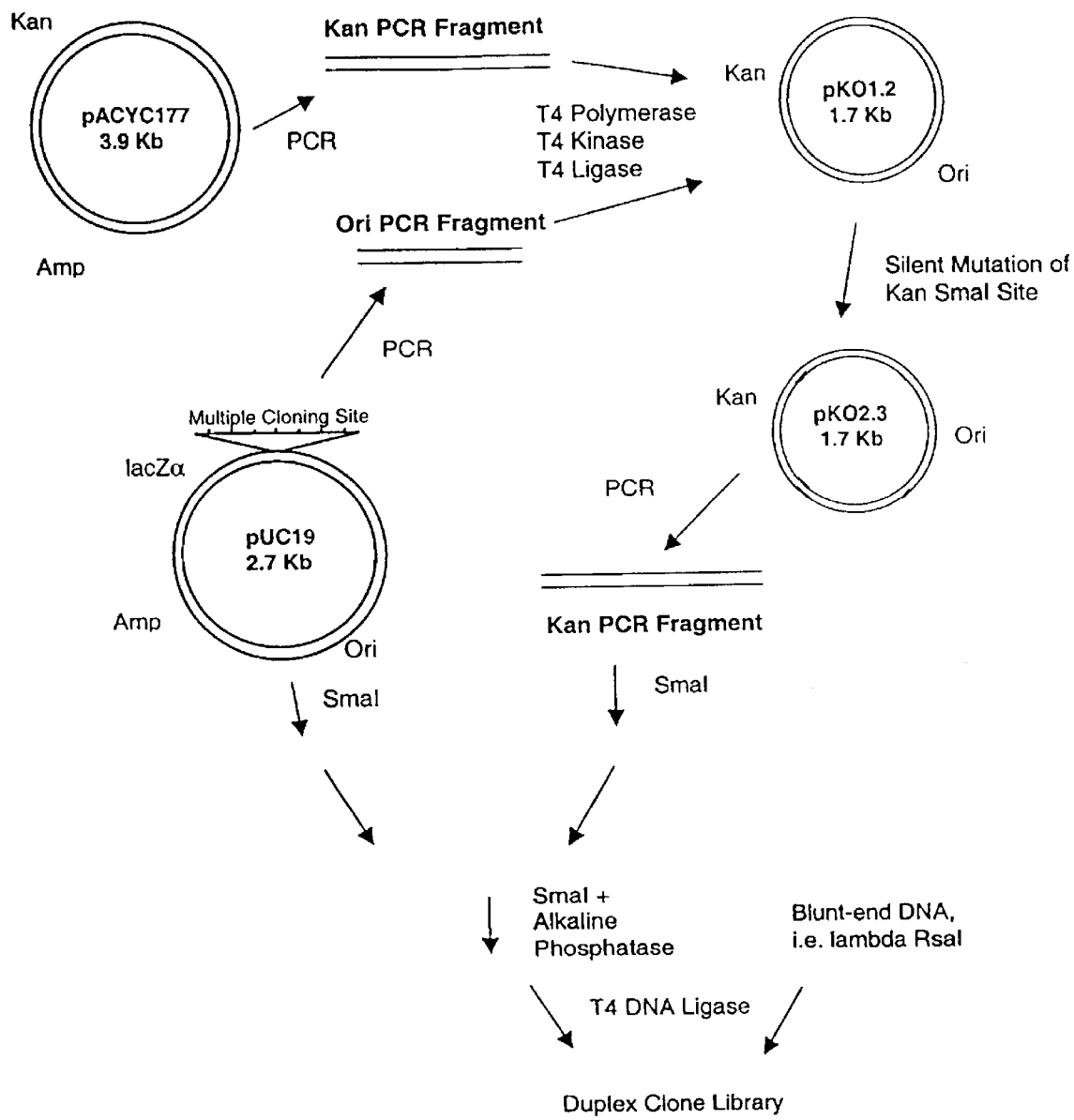
FIG. 3 shows the construction of a duplex clone library using two sources to supply the vector components.

A. Duplex Cloning with Partial Source Nucleic Acid from Plasmid and Partial Source Nucleic Acid from PCR A duplex clone library was constructed using two selectable markers, one obtained by PCR amplification of the Kan gene and the other from the plasmid pUC19. FIG. 3 shows the origin of the selectable markers and how they were processed to make the duplex shotgun library. This duplex cloning experiment combined SmaI restricted and alkaline phosphatase treated pUC19 with the PCR amplified Kan fragment treated with T4 DNA polymerase to make the ends blunt. These components were combined in 3 separate reactions as follows: 1) A no ligase, no insert control reaction to test for the level of empty vector background (pUC19/SmaI/AP+Kan−ligase); 2) A plus ligase, no insert control reaction to check for the level of self ligation (pUC19/SmaI/AP+Kan+ligase); 3) A plus ligase, plus insert reaction to test the overall efficiency of duplex cloning (pUC19/SmaI/AP+Kan+λRsaI+ligase). The ligation reactions contained a total of 200 ng pUC19 SmaI/AP+Kan PCR in equal molar amounts. Approximately one fifth of this reaction was transformed into *E. coli* DH5αFT, and an aliquot was spread on TY agar plates containing ampicillin or ampicillin plus kanamycin. The transformation results are presented in Table 4.

TABLE 4

Efficiency of duplex cloning combining a plasmid and PCR amplified selectable marker from partial sources

| Ligation reaction | Antibiotic plate | # colonies/ ml transformed cells |
|---|---|---|
| pUC19/SmaI/AP + Kan − ligase | amp | 56,000 |
| pUC19/SmaI/AP + Kan + ligase | amp | 66,000 |
| pUC19/SmaI/AP + Kan + λRsaI + ligase | amp | 120,000 |
| pUC19/SmaI/AP + Kan − ligase | amp + kan | 0 |
| pUC19/SmaI/AP + Kan + ligase | amp + kan | 0 |
| pUC19/SmaI/AP + Kan + λRsaI + ligase | amp + kan | 360 |

The pUC19/SmaI/AP+Kan−ligase reaction is a control containing only selectable marker fragments to test the degree of background due to intact source DNA. The high background of intact pUC19 vector alone is readily seen when plated on amp agar plates (approx. 56,000 colonies). However, plating the same mixture on the combination of amp+kan antibiotic prevented this background event in this Example. Thus, using separate partial sources to provide the selectable components of the duplex vector, pUC19 for the Amp gene and pKO2.3 to provide the Kan gene by PCR amplification, eliminated the background associated with conventional plasmid cloning methods.

The pUC19/SmaI/AP+Kan+ligase reaction is a control containing the selectable marker DNAs in the presence of ligase. On amp+kan agar plates no colonies were detectable, demonstrating that the level of dephosphorylation was sufficiently high. The background of intact plus relegated pUC19 vector is readily seen when plated on amp (approx. 66,000 colonies). This duplex cloning experiment resulted in approximately 360 recombinant clones.

B. Triplex Cloning with Partial Source Nucleic Acid from PCR

Figure 4:
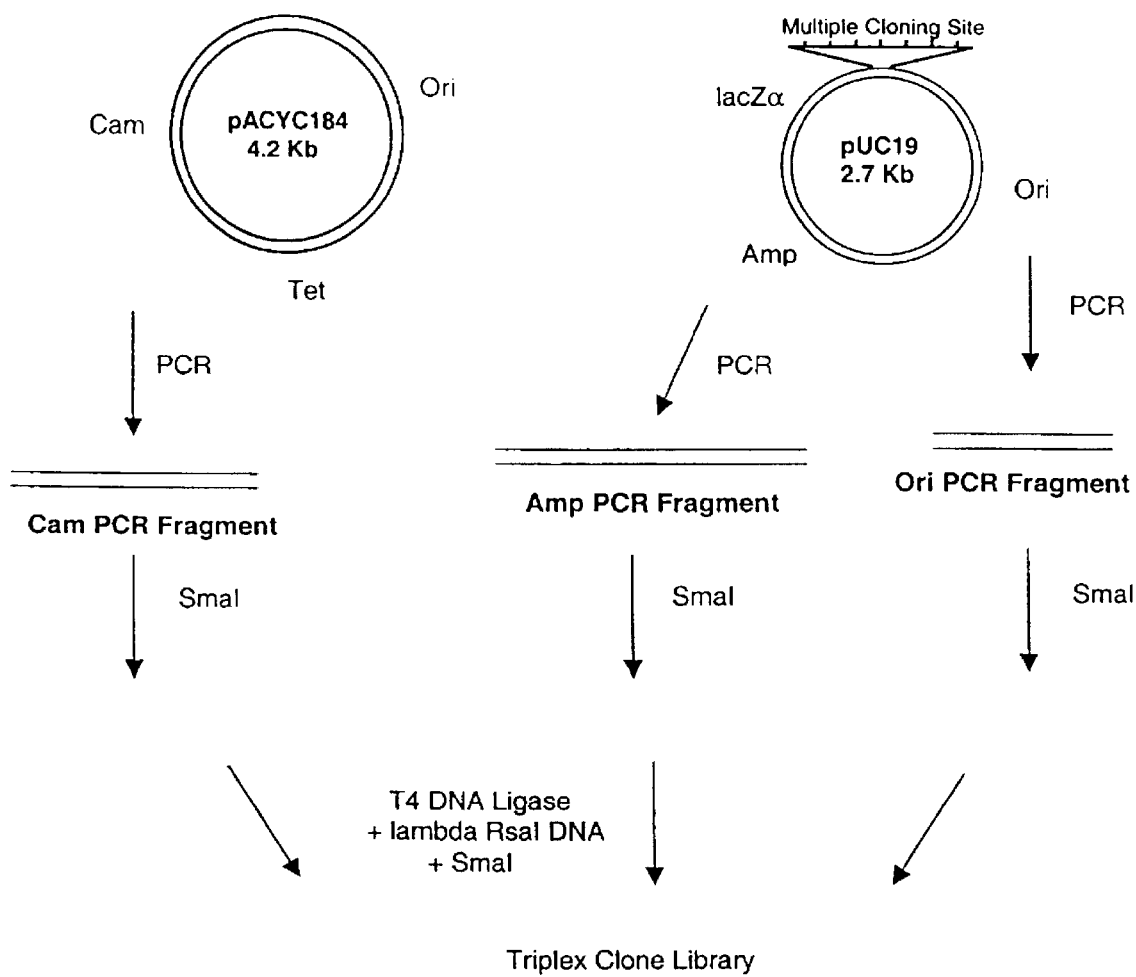
FIG. 4 shows the construction of a triplex clone library using PCR amplified selectable markers from independent plasmid vectors. Amp; ampicillin resistance gene, Cam; chloramphenicol resistance gene, Tet; tetracycline resistance gene, lacZα; alpha fragment of the lacZ gene, Ori; origin of replication, SmaI; recognition site for SmaI restriction endonuclease.

A triplex clone library was constructed by combining three selectable marker fragments, obtained by three PCR amplifications from two separate partial source plasmid templates, in a single ligation reaction. FIG. 4 shows the origin of the selectable markers and how they were processed to make the triplex shotgun clone library. The chloramphenicol-resistance gene (camR or Cam) from plasmid pACYC184 was amplified by PCR using the flanking oligonucleotide primers CML.2 (5'-TGG ACG TTA ACC CGG GCC TAC TAG GCC TTG ATC GGC ACG TAA GAG GTT CCA-3', SEQ ID NO:3) and CMR2 (5'-TTA CGC CCC GCC CTG CCA CTC A-3', SEQ ID NO:4). The ampicillin-resistance gene (ampR) was obtained from pUC19 using the primers APL2 (5' -CTG TTA ACC CGG GCG CGC CTG TGC GCG AAA CCC CTA TTT GTT TAT TTT C-3', SEQ ID NO:5) and APR2 (5'-TGG ACG TAC CCG GGC GCA GAA AGG CCA CCC GAA GGT GAG CCA GTG TGA TTA CAT TTA CCA ATG CTT AAT CAG TGA GGC ACC T-3', SEQ ID NO:6). A minimal origin of replication from pUC19 was amplified by PCR using the primers ORIL2 (5'-CTG TTA ACC CGG GAT TTA AAT CGT TGC TGG CGT TTT TCC ATA GGC TC-3', SEQ ID NO:7) and ORR1 (5'-TGG ACG TTA ACC CGG GTA GAA AAG ATC AAA GGA TCT-3', SEQ ID NO:8). After PCR amplification each of the fragments were restricted with SmaI and ligated in equal molar mass to DNA prepared from RsaI digested lambda DNA. No attempt was made to dephosphorylate the selectable marker fragments after cleavage with SmaI in this Example.

To demonstrate feasibility of triplex cloning, SmaI restricted, PCR amplified Amp, Cam, and Ori selectable marker DNA fragments were combined in 3 separate reactions as follows: 1) A no ligase, no insert control reaction to test for the level of empty vector background (Amp+Cam+ Ori−ligase); 2) A plus ligase, no insert control reaction to check for multiple marker insertion events and the size of empty vector DNA (Amp+Cam+Ori+ligase); 3) A plus ligase, plus insert reaction to test the overall efficiency of triplex cloning (Amp+Cam+Ori+λRsaI+ligase+SmaI). To enrich for the desired final result of 100% recombinants, the last ligation reaction also included SmaI to recleave any vector ends, which recreate a SmaI site, and thereby force the cloning of insert DNA (Liu and Schwartz, Biotechniques 12:28–30, 1992). A total of 250 ng of selectable marker DNA was used in each reaction. Approximately one tenth of the ligation reaction was transformed into *E. coli* DH5αF'IQ, and an aliquot was spread on TY agar plates containing ampicillin plus chloramphenicol. The cell transformation results are presented in Table 5.

TABLE 5

Efficiency of cloning three DNA fragments using PCR amplified selectable markers.

| Ligation reaction | Antibiotic plate | # colonies/ml transformed cells |
| --- | --- | --- |
| SmaI Amp + Cam + Ori − ligase | amp | 8000 |
| SmaI Amp + Cam + Ori − ligase | cam | 8000 |
| SmaI Amp + Cam + Ori − ligase | amp + cam | 0 |
| SmaI Amp + Cam + Ori + ligase | amp + cam | 400 |
| SmaI Amp + Cam + Ori + λRSaI + ligase + SmaI | amp + cam | 3000 |

The Amp+Cam+Ori−ligase reaction is a control containing only selectable marker fragments to test the degree of background from intact vector source DNA. Significantly, the use of partial source nucleic acid, namely PCR fragments from pUC19 for Amp and Ori and from pACYC184 for Cam, to provide the components of the complete triplex vector eliminated the background associated with conventional plasmid cloning methods.

The Amp+Cam+Ori+ligase reaction is a control containing selectable marker DNA only. As expected, the three selectable markers generated viable clones in the presence of ligase, as seen by the 400 colonies/ml of transformed cells. To study the possibility of multiple marker insert events (e.g. two or more copies of the Amp, or Cam, or Ori markers in any one plasmid), six colonies were picked and grown, and the plasmid DNA was extracted for size analysis by agarose gel electrophoresis. All 6 plasmids migrated equally and were the size predicted for the 3 fragments being correctly joined as one.

This triplex cloning Example resulted in approximately 3000 recombinant clones/ml of transformed cells using 25 ng of vector fragment DNAs (10% of the 250 ng of starting material) to transform electrocompetent cells. Restriction analysis of 12 recombinant clones showed that all 12 were larger than the predicted empty vector. In addition, the number of inserts in each clone could be estimated by SmaI restriction analysis, as each insertion eliminates the SmaI site that would be recreated by joining of vector fragments. This analysis indicated that 8/12 clones had inserts in all 3 sites, 2/12 had two inserts, and 2/12 had 1 insert. The four clones that showed evidence of restriction by SmaI apparently escaped the selective pressure of SmaI in the ligation reaction.

C. Quadraplex Cloning with Partial Source Plasmid Nucleic Acid

This Example describes quadraplex cloning with partial source plasmid nucleic acid. Two partial source plasmids were constructed as follows: 1) Amp+Cam+Ori, or pACO3, and 2) Kan+Ori, or pKO2.3 (described in Example 3).

Figure 5:
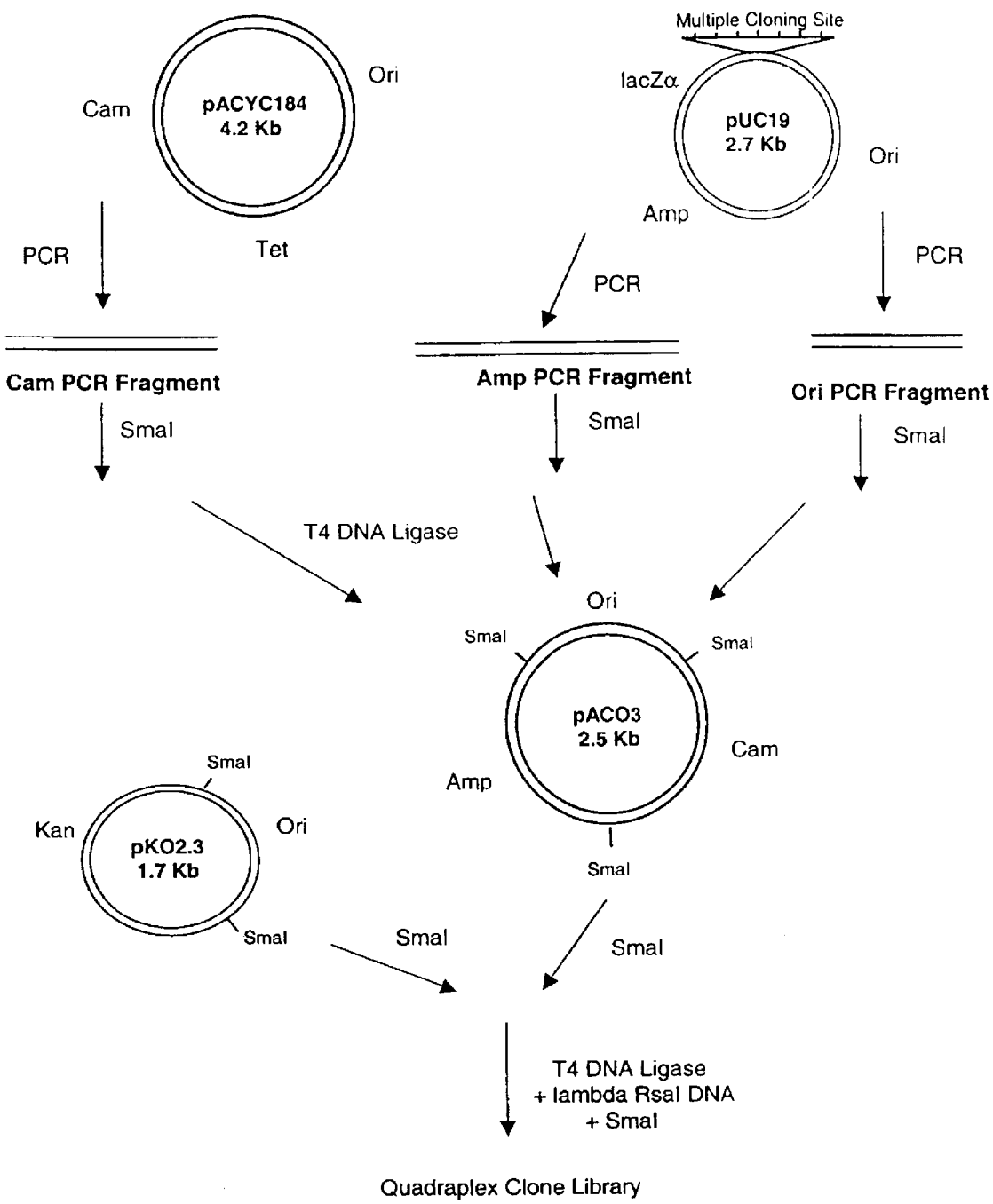
FIG. 5 shows the construction of a quadraplex clone library construction using two independent plasmid vectors.

FIG. 5 shows the origin of the selectable markers and how they were processed to make the quadraplex shotgun clone library. The chloramphenicol gene, ampicillin gene, and origin of replication from pUC19 were amplified by PCR using the primers described in Example 4B. After PCR amplification, each of the fragments was restricted with SmaI and ligated in equal molar mass to create pACO3. To generate the fragments for quadraplex cloning, pACO3 and pKO2.3 DNAs were purified and restricted with SmaI, and the resulting fragments (SmaI pACO+pKO) were ligated to DNA prepared from RsaI digested lambda DNA. To demonstrate quadraplex cloning a total of 200 ng of selectable marker DNA was combined, with or without ligase or test insert DNA. Approximately one tenth of the ligation reaction was transformed into E. coli DH5αF′IQ, and an aliquot was spread on various antibiotic containing agar plates, with cell transformation results shown in Table 6.

TABLE 6

Efficiency of cloning four DNA fragments using two partial source vectors.

| Ligation reaction | Antibiotic plate | # colonies/ml transformed cells |
| --- | --- | --- |
| SmaI pACO + pKO − ligase | amp + cam | 20,480 |
| SmaI pACO + pKO − ligase | kan | 18,720 |
| SmaI pACO + pKO − ligase | amp + cam + kan | 0 |
| SmaI pACO + pKO + ligase | amp + cam + kan | 40,000 |
| SmaI pACO + pKO + λRsaI + ligase + SmaI | amp + cam + kan | 1260 |

The SmaI pACO+pKO−ligase reaction is a control containing only selectable marker fragments to test the degree of background contamination due to uncut vector commonly seen in conventional cloning. The use of separate, starting vectors, pACO and pKO2.3 in this instance, which are restricted and mixed to provide the components of the complete quadraplex vector, combined with selection against each of the individual starting plasmids, eliminated background problems due to uncut vectors. The background of pACO vector or pKO2.3 vector alone is readily seen when the transformants were plated on amp+cam or kan, respectively. However, plating the same mixture on the combination of amp+cam+kan antibiotics prevented this unwanted background event. Significantly, this Example demonstrates the co-cloning of four DNA fragments with four selectable markers in one plasmid vector. The quadraplex cloning experiment resulted in approximately 1260 recombinant clones/ml transformed cells using 10% of the ligation reaction (100%=200 ng). As with the triplex experiment above, SmaI was included in the reaction with lambda DNA fragments to force the co-cloning of insert DNA. The number of inserts in each clone was estimated by SmaI restriction analysis (the lack of SmaI restriction indicating foreign DNA insertion), with the following results: 5/12 had inserts in all 4 sites, none of the clones contained three inserts, 2/12 had 2 inserts, 3/12 had one insert and 2/12 had no inserts.

D. Pentaplex Cloning with Partial Source Nucleic Acid from a Plasmid

Figure 6:
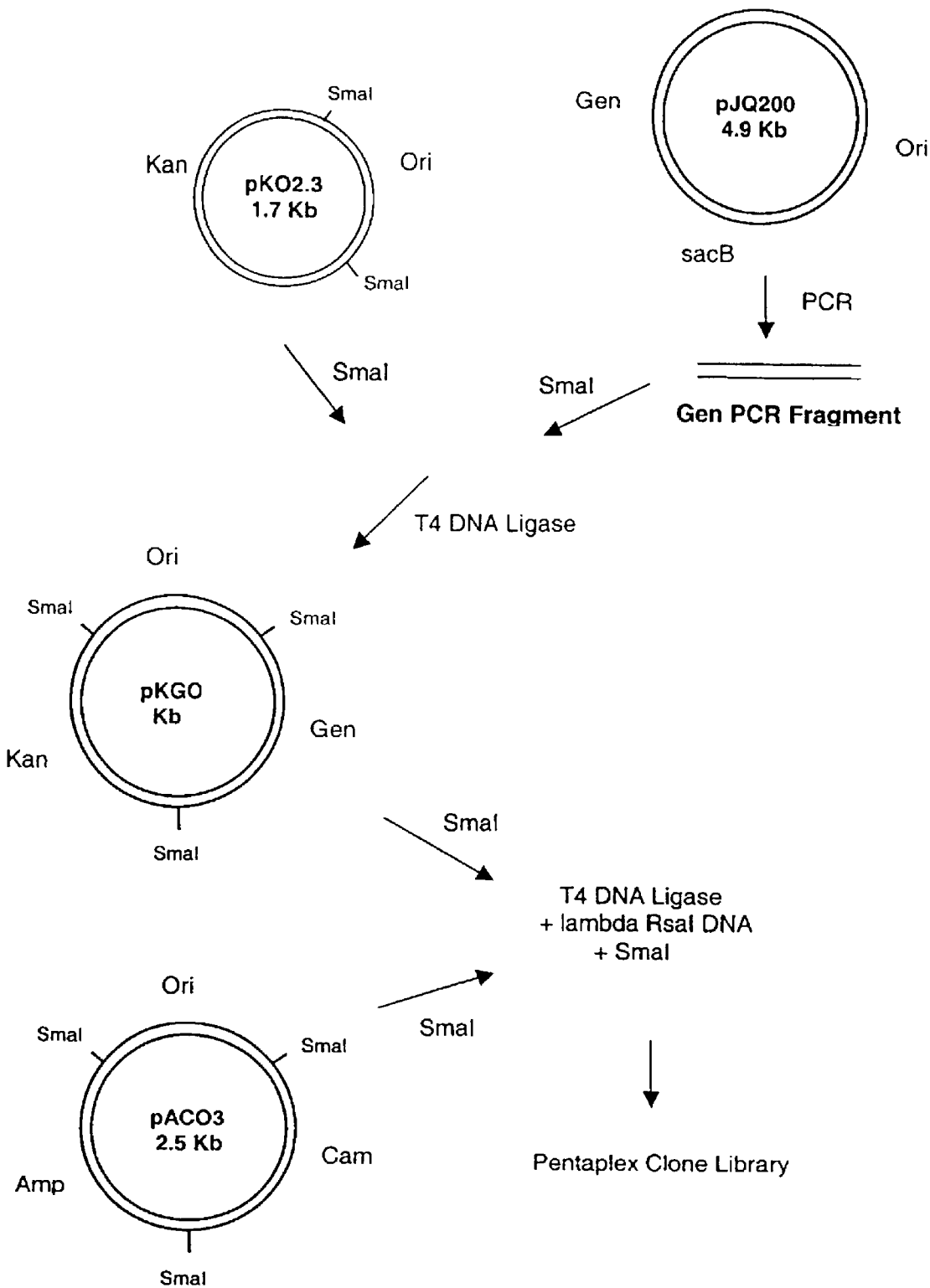
FIG. 6 shows the construction of a pentaplex clone library using two independent plasmid vectors.

A pentaplex clone library was constructed using two plasmids to supply the necessary selectable components. The plasmids were constructed as follows: 1) Amp+Cam+Ori, or pACO3 (described in Example 4C), and 2) Kan+Gen+Ori, or pKGO. FIG. 6 shows the origin of the selectable markers and how they were processed to make the pentaplex shotgun clone library. The gentamycin gene from plasmid pJQ200 was amplified by PCR using the flanking oligonucleotide primers GML1 (5′-CACTGTTAACCCGGGAATTGACATAAGCCTGTTCG GTTCGTAAACT-3′, SEQ ID NO:9) and GMR1 (5′-GTGACAACCCGGGCAGATTAAAACGAAAGGCCCA GTCTTTCGACTGAGCCTTTCGTTTTATTTGTTTAGG TGGCGGTACTTGGGTCGATATCA-3′, SEQ ID NO:10). After PCR amplification, the Gen fragment was restricted with SmaI and ligated to SmaI restricted pKO2.3 (described in Example 3) to generate pKGO. For pentaplex cloning pACO and pKGO were separately restricted with SmaI to liberate the individual selectable marker fragments. In this Example, a total of 200 ng of the selectable fragments was used in each reaction, with or without ligase or test insert. Approximately 80% of the ligation reaction was transformed into DH5αF′IQ, and an aliquot was spread on various antibiotic containing agar plates, with cell transformation results shown in Table 7.

TABLE 7

Efficiency of cloning five DNA
fragments using two partial source vectors

| Ligation reaction | Antibiotic plate | # colonies/ml transformed cells |
|---|---|---|
| SmaI pACO + pKGO − ligase | amp + cam | 20,000 |
| SmaI pACO + pKGO − ligase | kan + gen | 4080 |
| SmaI pACO + pKGO − ligase | amp + cam + kan + gen | 0 |
| SmaI pACO + pKGO + ligase | amp + cam + kan + gen | 8000 |
| SmaI pACO + pKGO + λRsaI + ligase + SmaI | amp + cam + kan + gen | 70 |

The SmaI pACO+pKGO+ligase reaction is a control containing only selectable marker fragments to test the background contamination due to uncut vector commonly seen in conventional cloning. The use of separate starting vectors, pACO and pKGO in this instance, to provide the components of the complete pentaplex vector eliminated the intact vector background (commonly seen in cloning experiments). The background of pACO vector or pKGO vector alone is readily seen on amp+cam or kan+gen, respectively. However, plating the same mixture on the combination of amp+cam+kan+gen antibiotic plates prevents this unwanted background event.

Significantly, this Example demonstrates the co-cloning of five DNA fragments with five selectable markers in one plasmid vector. This pentaplex cloning reaction resulted in approximately 70 recombinant clones/ml transformed cells. Higher concentrations of SmaI than that added in the quadraplex experiment above was used to force the co-cloning of insert DNA. Estimating the number of inserts by SmaI restriction analysis revealed that all 10 had inserts at all 5 sites. Although only 70 pentaplex clones were recovered in this experiment, it is notable that this number would be sufficient to sequence a 100 kb BAC with more than 3 fold redundancy, assuming 2 kb inserts at all five sites.

EXAMPLE 5

Triplex Cloning with Foreign Fragment Insertion Approaching 100%

This Example describes triplex cloning with the efficiency of foreign fragment insertion approaching 100%. The use of a restriction endonuclease, such as SmaI in the above Examples, to lower the probability of empty insertion sites is not a desirable option for generation of random shotgun libraries, because this approach, while selecting against empty insertion sites, also selects against recombinant clones with internal SmaI sites. Another approach to inhibit self-ligation of vector DNA, or DNA fragments with selectable markers, is to eliminate their 5' phosphate groups, thereby forcing ligation to the insert DNA, which does contain 5' phosphate groups. There are several methods for achieving this goal. One is to directly ligate synthetic oligonucleotides, which normally lack terminal phosphate groups, to the ends of the vector DNA. Another method is to use PCR amplified fragments, which likewise lack 5' phosphates due to the incorporation of the synthetic oligonucleotide printers at their 5' termini. Another method is to dephosphorylate the DNA with alkaline phosphatase (AP).

In this Example, triplex cloning with high efficiency fragment insertion was achieved using the Amp, Cam, and Ori selectable markers that were PCR amplified as described in Example 4B above. However, the fragments were end-repaired with T4 DNA polymerase rather than SmaI restricted. Thus, the selectable marker DNAs lacked phosphate groups at their ends, forcing ligation to the insert DNA, which bears phosphate groups. This Example demonstrates triplex cloning by combining the selectable marker DNA fragments in 3 separate reactions as follows: 1) A no ligase, no insert control reaction to test for empty vector background (Amp+Cam+Ori−ligase); 2) A plus ligase, no insert control reaction to assay self-ligation using end-repaired PCR fragments (Amp+Cam+Ori+ligase); and 3) A plus ligase, plus insert reaction to test the overall efficiency of triplex cloning (Amp+Cam−Ori+λRsaI+ligase). A total of 177 ng of selectable marker DNA was used in each reaction, with or without ligase or test insert. Approximately one fifth of the ligation reaction was transformed into DH5αF'IQ, and an aliquot was spread onto antibiotic containing agar plates, with cell transformation results shown in Table 8.

TABLE 8

Triplex cloning using end-repaired
PCR amplified selectable markers.

| Ligation reaction | Antibiotic plate | # colonies/ml transformed cells |
|---|---|---|
| Amp + Cam + Ori − ligase | amp + cam | 5 |
| Amp + Cam + Ori + ligase | amp + cam | 15 |
| Amp + Cam + Ori + λRsaI + ligase | amp + cam | 1895 |

Because the partial source backbone vectors used to generate the selectable markers have compatible origins of replication they can survive together in a single cell. This triplex cloning experiment resulted in approximately 1895 recombinant clones, with only 15 clones recovered from ligations lacking insert DNA. Thus, the efficiency of recovering recombinant clones is over 99%, as the background of empty vector transformation is 0.79% (15/1895×100).

To facilitate analysis of the number of copies of each selectable marker, a unique eight base restriction site was incorporated into the 5' end of each marker as follows: Amp, SwaI; Cam, AseI; and Ori, SfiI. Digestion of a triplex vector with each of these enzymes yields a single restriction fragment if one copy of each marker is present. Each additional copy of a selectable marker will result in one additional fragment from digestion with the respective enzyme (the random presence of any of these restriction sites in the cloned insert DNA will be uncommon due to the rare occurrence of these sites). By this analysis, it was estimated that multiple insertions occurred in 12/87 clones or 13.80%. However, the unusable fraction of sequencing reactions possible from the recombinant triplex clones is actually lower than 13.8%. There are 6 primer extension sites in each template in the triplex cloning situation, only two of which are unusable due to multiple insertions. The 87 clones will yield a total of 87×6 or 522 DNA sequence reactions. The 12 clones with multiple insertions will each yield 2 unreadable DNA sequence reactions, or 24 total. Therefore, 24/522 or 4.2% of the reactions will be unreadable due to multiple insertions of a given selectable marker.

EXAMPLE 6

Construction of a Direct Selection Cloning Vector

Using antibiotic selectable markers from partial source plasmid backbones is an efficient method of reducing the contaminating background of empty vector in a multiplex cloning experiment. It was determined, however, that this method is not always 100% efficient, as a low but measurable number of clones (approximately 0.1–0.5%) contained two separate plasmids in a single cell. Size analysis revealed that the presence of two plasmids was the result of a double transformation event with two empty vectors. This result is not unexpected, given the mixture of two or more plasmids in the multiplex ligation reactions, the high transformation efficiency of denatured but un-cleaved DNA, and the low transformation efficiency of restricted, re-ligated DNA.

This Example describes the construction of direct selection vector based on the bacteriophage T7 gene 1.2., in addition to its use in a conventional (single insert) cloning reaction. Three potential positive selection cloning systems, based on the sacB gene, the Bax, and the bacteriophage T7 1.2 gene (Schmitt et al., J Bacteriol., 173:1536–43, 1991), were designed and tested as adjuncts for low background cloning. The sacB gene mediating sucrose sensitivity had been developed previously by other researchers as a direct selection cloning scheme for use in E. coli. For unknown reasons we were not able to readily obtain these results in this Example. The Bax gene has been shown previously to be highly toxic when expressed in E. coli, but for unknown reasons we were not able to readily control the expression of this gene. Expression of bacteriophage T7 gene 1.2 is lethal to F' containing E. coli but not F minus strains. Thus, plasmid-based expression of this gene product should be lethal in male E. coli cells but not female strains.

Figure 7:
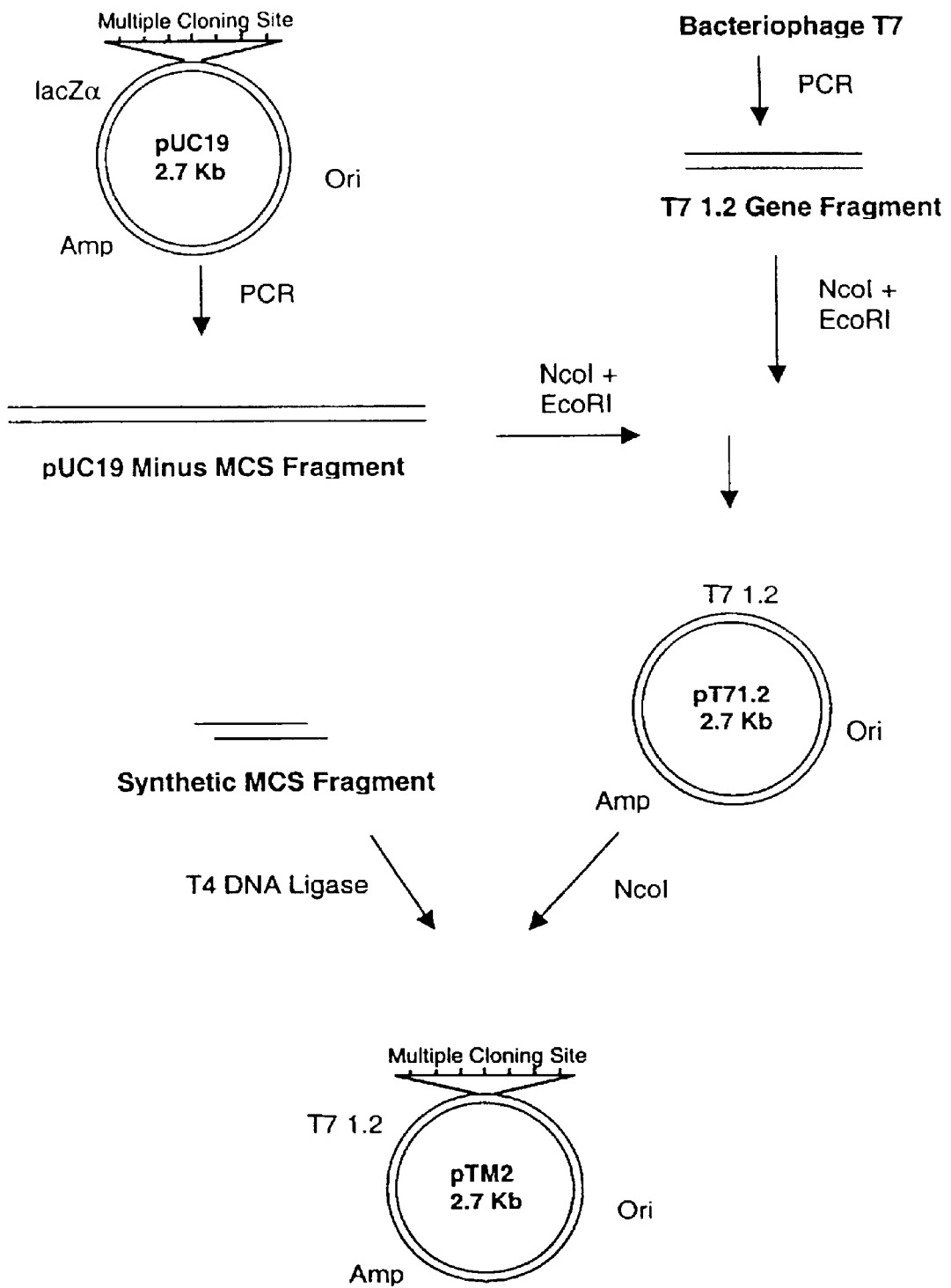
FIG. 7 shoves the construction of T7 gene 1.2 based direct selection vectors.

Of the three systems tested, only the bacteriophage T7 1.2 gene product provided sufficient control of the background transformants. FIG. 7 diagrams the construction of pT71.2 and pTM2, vectors employed in this Example. Combining most of pUC19 with the T7 gene 1.2 coding sequence resulted in the initial positive selection vector pT71.2. The majority of pUC19, except for the multiple cloning site and the first 7 amino acids of the lacZα gene, were amplified using the primers LACZNCOL (5'-CAGTGTCACTCCATGGCCATGATTACGCCAAGCTTGCATGCCTGCAGGTCGACTCTAG SEQ ID NO:11) and LACZNCOR (5'-CAGTGTCACTCCCATGGCTGTTTCCTGTGTGAAATTGTTATCCGCTCACAA SEQ ID NO:12). Gene 1.2 was amplified from bacteriophage T7 (J Bacteriol., 173:1536–43, 1991) using the oligonucleotides T71.2L (5'-TGTCACTCCATGGGACGTTTATATAGTGGTAATCTGGCAGCA-3' SEQ ID NO:13) and T71.2R (5'-CTGACTCGAATTCTTACTTCCAGTCCTTCAACTGGTCATAGATA-3', SEQ ID NO: 14) and cloned in frame with the lacZα start codon in pUC19.

The correct pT71.2 construct, confirmed by restriction and size analysis, was tested for lethality in two strains of E. coli: the F plus strain DH5αF'IQ and the F minus strain DH10B. As the T7 1.2 gene was inserted behind the ATG start codon of the lacZ gene in pT71.2, its expression is controlled by the lacZα promoter. The gratuitous inducer of the lacZ promoter, IPTG, is often used to increase the level of expression from this regulatory element. In the presence of IPTG, approximately 2000 fold fewer colonies were observed when supercoiled pT71.2 DNA was transformed into the F plus strain DH5αF'IQ rather than the F minus strain DH10B. In the absence of IPTG, no difference in colony forming units was observed between the two strains.

The T7 1.2 gene lacks useful restriction sites for cloning within its short coding sequence. In order to make a more functional direct selection cloning vector, a multiple cloning site identical to that found in pUC19 was inserted between the first and second codons of the T7 gene 1.2 in pT71.2, as shown in FIG. 7, resulting in the plasmid pTM2. Two synthetic oligonucleotides, T7 MCS TOP (5'-CATGCAAAGCTTGCATGCCTGCAGGTCGACTCTAG AGGATCCCCGGGTACCGAGCTCGAATTCTAG-3' SEQ ID NO:29) and T7 MCS Bottom (5'-CATGCTAGAATTCGAGCTCGGTACCCGGGGATCCT CTAGAGTCGACCTGCAGGCATGCAAGCTTTG-3'SEQ ID NO:30), were annealed to yield a double stranded multiple cloning site fragment with NcoI overhanging ends. This sequence was ligated to NcoI digested pT71.2.

The correct pTM2 construct, confirmed by restriction and size analysis, was tested for lethality in DH5αF'IQ and DH10B. pTM2 also showed a 2000 fold differential plating efficiency in DH10B versus DH5αF'IQ using supercoiled plasmid DNA, again only in the presence of IPTG.

To test the efficiency of pTM2 as a direct selection cloning vector, the plasmid was restricted with SmaI, dephosphorylated with alkaline phosphatase (AP), and incubated with or without ligase and insert DNA. The DNA was used to transform DH5αF'IQ or DH10B and plated on ampicillin plus IPTG agar.

TABLE 9

Efficiency of direct selection cloning using an engineered T7 1.2 gene construct.

| Ligation reaction | DH5αF'IQ # colonies/ ml transformation | DH10B # colonies/ ml transformation |
|---|---|---|
| SmaI pTM2/AP – ligase | 1700 | 5200 |
| SmaI pTM2/AP + ligase | 2600 | 12,300 |
| SmaI pTM2/AP + λRsaI + ligase | 416,000 | 142,000 |

In this Example, direct selection cloning resulted in approximately 416,000 recombinant clones when transformed into DH5αF'IQ. The frequency of empty vector versus insertion ligation events was 0.6% (2600/416000× 100),or 31,63 fold more colonies when insert DNA was present. The same DNA transformed into DH10B resulted in an empty parental vector background of approximately 8.6%(12300/142000×100). The transformation efficiency of the two strains, DH10B and DH5αF'IQ, was the same using a pUC19 control plasmid, confirming that the differences seen with pTM2 reflect selection against this plasmid in DH5αF'IQ, rather than simply a lower transformation efficiency of this strain.

EXAMPLE 7

Multiplex Cloning with a Direct Selection Vector

This Example describes multiplex cloning employing a direct selection vector. In particular, this Example describes duplex cloning wherein pTM2/SmaI/AP was mixed with a PCR amplified Cam gene (see e.g., Example 3B), which was end-repaired with T4 DNA polymerase. Three separate reactions were performed as follows: 1) A no ligase, no insert control reaction to test for the level of empty vector background contamination (pTM2/AP+Cam–ligase); 2) A plus ligase no insert control reaction to check the level of self-ligation (pTM2/AP+Cam+ligase); 3) A plus ligase, plus insert reaction to test the overall efficiency of duplex cloning (pTM2/AP+Cam+λRsaI+ligase). In this Example a total of 100 ng of selectable marker DNA was used in each reaction. Approximately one fifth of the ligation reaction was transformed into DH5aF'IQ, and an aliquot was spread on amp+ cam antibiotic plates, with cell transformation results shown in Table 10.

TABLE 10

Multiplex cloning using a direct selection
vector and PCR amplified selectable marker.

| Ligation rx | # colonies/ ml transformation |
| --- | --- |
| pTM2/AP + Cam − ligase | 135 |
| pTM2/AP + Cam + ligase | 130 |
| pTM2/AP + Cam + λRSaI + ligase | 15,600 |

As seen in Table 10, the multiplex cloning reaction illustrated by this Example resulted in 15,600 recombinant clones. The frequency of empty vector versus insertion ligation events was 0.83% (130/15600×100). The frequency of multiple selectable marker insertion events was estimated by restriction analysis using the unique eight base restriction site associated with each marker, as described above. Three of 60 clones analyzed, or 5.0%, had multiple inserts. The three clones with multiple inserts will yield 6 unusable sequencing reactions. Compared to a total of 240 reactions from the 60 analyzed clones, 2.5% (6/240) of the sequencing reactions will be unreadable due to multiple fragment insertions.

EXAMPLE 8

Construction of Second Generation Direct Selection Multiplex Cloning Vectors

Figure 8:
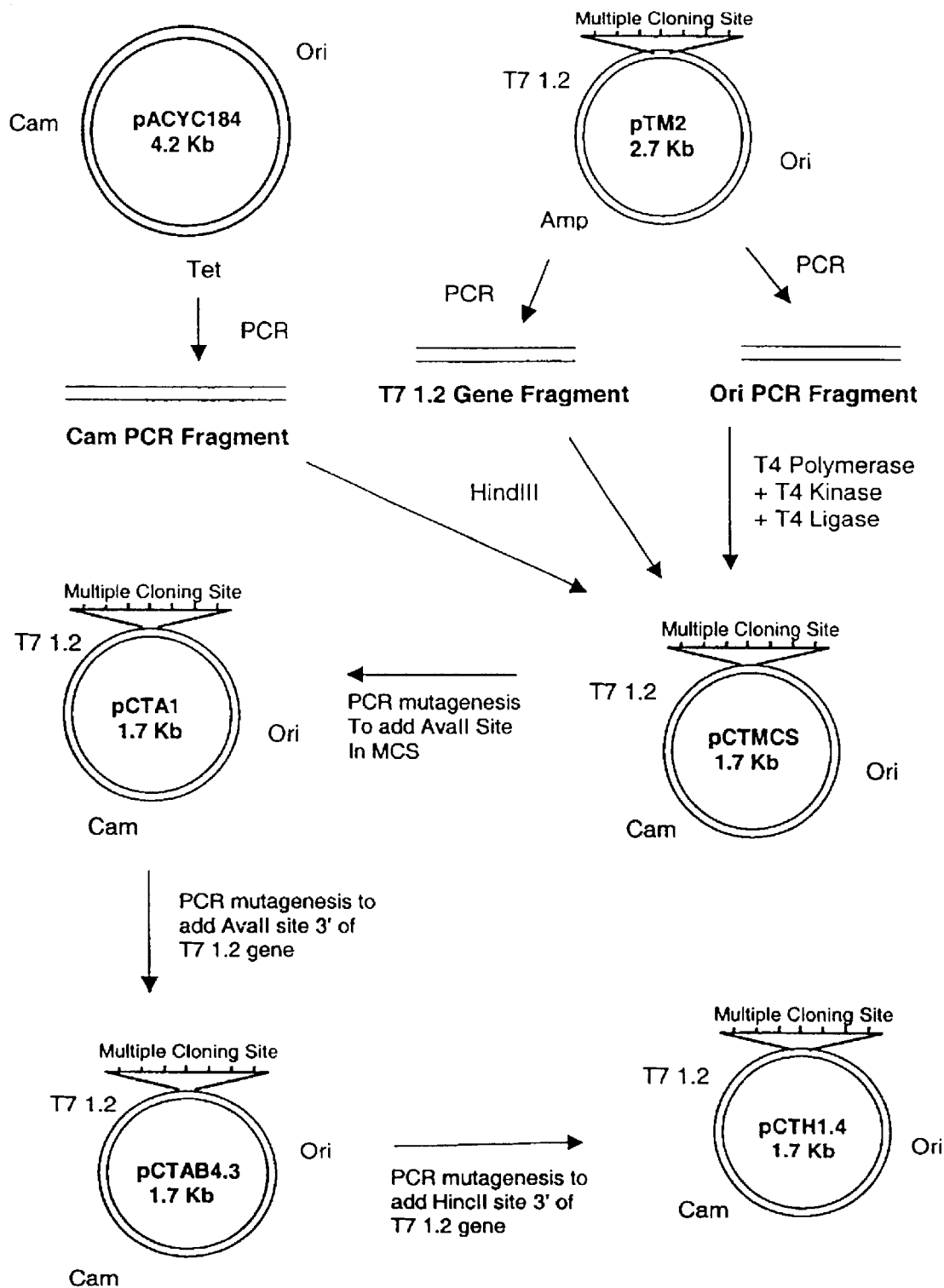
FIG. 8 shows the construction of second generation direct selection cloning vectors.

This Example describes the construction of second generation direct selection multiplex cloning vectors (e.g., smaller or amenable to excision of the direct selection fragment). FIG. 8 diagrams construction of the direct selection cloning vectors pCTA1, pCTAB4.3, and pCTH1.4. The conditionally lethal bacteriophage T7 1.2 gene, with its engineered multiple cloning site, was amplified from pTM2 (described in Example 6) using oligonucleotides LZL1(5'-CATTAGGCACCCCAGGCTTTACACTTTATG-3', SEQ ID NO: 15) and T71.2R2 (5'-TTATTACTTCCAGTCCTTCAACTGGTCATACATATG GTTC-3', SEQ ID NO:16). The chloramphenicol resistance gene was PCR amplified from pACYC184 using the primers CML2 (SEQ ID NO:3) and CMRT7 (5'-CAGACTGTGCAAGCTTTGCATTTACGCCCCGCCC TGCCACTCA-3', SEQ ID NO:18). The T7 and Cam PCR fragments were made blunt by treatment with T4 DNA polymerase, the ends were phosphorylated using T4 kinase, and both fragments were restricted with endonuclease HindIII. A minimal origin of replication was PCR amplified using the ORIL2 (SEQ ID NO:7) and ORR1 (SEQ ID NO:8) primers described earlier. The Ori PCR fragment was digested with SmaI. All three fragments were combined in a ligation reaction and transformed into DH10B cells.

The ATG start codon of the T7 1.2 gene was joined immediately after the TAG stop codon of the chloramphenicol resistance gene to form a single operon by HindIII digestion and subsequent ligation of the 3' Cam PCR fragment and 5' T7 1.2 PCR fragment. A minimal origin of replication was added to form the 1.7 kb plasmid pCTMCS which was confirmed by restriction and size analysis and was functionally tested for direct selection capabilities in DH5αF'IQ and DH10B. This plasmid has a single promoter, from the Cam gene, driving the expression of both the Cam and T7 1.2 genes. This design circumvents the need for two separate promoters and results in constitutive expression of the T7 1.2 gene, eliminating the need for IPTG induction.

Additional vectors with alternative restriction sites were constructed in this Example. The multiple cloning site of pCTMCS was modified to add an AvaII restriction site, using PCR primers AVAL(5'-TCCTCTAGAGTCGACCTGCAGGCA-3', SEQ ID NO:19) and AVAR (5'-CCGGGTACCGAGCTCGAATTCTAGCA-3', SEQ ID NO:20), which were designed so as not to disrupt the reading frame of the T7 1.2 gene. The resulting plasmid was designated pCTA1. The enzyme AvaII was chosen for its ability to leave a three base extension, which alkaline phosphatase is expected to use very efficiently as a substrate for dephosphorylation, decreasing the likelihood of vector re-ligation. Further, filling in the three base extension with T4 DNA polymerase and dNTPs results in generation of a triplet codon, which will not disrupt the reading frame of the T7 1.2 gene in those cases in which re-ligation of the vector does occur, retaining the positive selection against the re-ligated, non-recombinant vector.

The single AvaII site of pCTA1 is situated at codon 13 of the MCS T7 1.2 gene hybrid construct. The authentic second codon of T7 gene 1.2 is located 7 codons further downstream. Thus, it is possible that a DNA insertion at the AvaII site could disrupt the reading frame of the downstream T7 1.2 gene, but subsequent translation re-initiation or frame-shifting could result in an intact toxic gene product. To circumvent this possibility, three restriction endonuclease sites were added facilitate removal of the T7 1.2 gene from pCTA1, creating the plasmid pCTAB4.3 (FIG. 8). A second AvaII site was added to the 3' end of the T7 1.2 gene using PCR primers Ava2L: ACCAAAGATCTTATTACTTC-CAGTCCTTCAACTGGTCA (SEQ ID NO:31) and Ava2R: CCTGCAGGGAGCATTTAAATCGTTGCTG-GCGTTTTTCCATAGGCT (SEQ ID NO:32). The presence of AvaII sites at both ends of the T7 1.2 gene allows its complete removal upon digestion with AvaII.

In addition, two BglII sites were incorporated within the T7 1.2 gene within codons that could be mutated without changing the amino acid sequence, using PCR primers T7BL3: CTGTCCTCAATACGTAACCGTATG-CAATCTTTTCTTGTA (SEQ ID NO:33), T7BR3: ATCTG-GAAACCTGATTGATACTAGCACCTTCTACCA (SEQ ID NO:34), T7BL4: TCTGAGCTCGGTACCCGGTC-CTCTAGAGTCGA (SEQ ID NO:35) and T7BR4: TCT-TAGCATGGGACGTTTATATAGTGG-TAATCTGGCAGCA (SEQ ID NO:36). Following liberation of the T7 1.2 gene fragment by AvaII digestion, further digestion with BglII will cleave the T7 1.2 gene into segments less than 200 bases in length. This cleavage facilitates purification of the vector backbone away from the T7 1.2 sub-fragments by fractionation, for example, with diatomaceous earth (DE) or precipitation with 7% 8000 MW polyethylene glycol and 10 mM magnesium chloride (PEG8000/MgCl$_2$).

Further PCR mutagenesis reactions were employed to add a HincII restriction site to the 3' end of the T7 1.2 gene, using PCR primers CHp1138R: TAT AGT TAA CGC TCC CTG CAG GAC CA (SEQ ID NO:37) and CHp1138F: GGC AGT TAA CAT TTA AAT CGT TGC TGG CGT (SEQ ID NO:38), and to remove an unwanted HincII site between the Cam gene and Ori using PCR primers CAp29F: TAT TGG GCC CTG ATC GGC ACG TAA GAGG (SEQ ID NO:39) and CAp1772R: TCA TGGCGCC CAA AAG ATC AAA CGA TCC TCT TGA GA (SEQ ID NO:40). These HincII sites provide an alternative method to excise the T7 1.2 gene while simultaneously generating a blunt-ended vector. As shown in FIG. 8, the resulting direct selection construct is plasmid pCTH1.4 (sequence provided in FIG. 11, SEQ ID NO:41).

An indirect experiment was performed to measure the level of false negative cloning results from the T7 1.2 based suicide vectors. The plasmid vectors pCTA1 and pCTAB4.3 are nearly identical in structure and sequence, the primary difference between them being the additional AvaII restriction site in pCTA4.3 that allows the T7 1.2 gene to be excised completely.

pCTA1 and pCTAB4.3 were restricted with AvaII, dephosphorylated with Thermosensitive Alkaline Phosphatase, and treated with T4 DNA polymerase to generate blunt ends. pCTAB4.3 was further digested with BglII and purified to completely remove the T7 1.2 gene from the Cam+Ori plasmid backbone. A direct selection clone library was constructed from each of these treated vectors to determine the empty vector background and false negative cloning results. Three separate ligation reactions were prepared as follows: 1) A no ligase, no insert control reaction to test for the level of contaminating empty vector (pCTA1 or pCTAB4.3/AvaII/AP–ligase); 2) A plus ligase, no insert control reaction to check for the efficiency of 5' phosphate removal (pCTA1 or pCTAB4.3/AvaII/AP+ligase); 3) A plus ligase, plus insert reaction to test the cloning efficiency (pCTA1 or pCTAB4.3/AvaII/AP+λRsaI+ligase). The ligation reactions contained 100 ng of treated vector DNA. Approximately one fifth of this reaction was transformed into E. coli DH5αF', and an aliquot was spread onto TY agar plates containing chloramphenicol. The transformation results are presented in Table 11.

TABLE 11

Cloning assay to assess false negative results with or without the intact T7 1.2 gene

| Ligation rx | # colonies/ml transformation |
| --- | --- |
| pCTA1/AvaII/AP − ligase | 333 |
| pCTA1/AvaII/AP + ligase | 22,000 |
| pCTA1/AvaII/AP + λRsaI + ligase | 493,000 |
| pCTAB4.3/AvaII/AP − ligase | 0 |
| pCTAB4.3/AvaII/AP + ligase | 32,600 |
| pCTAB4.3/AvaII/AP + λRsaI + ligase | 1,530,000 |

The background of empty vector was similar for both treated plasmids: 4.5% using pCTA1 (22,000/493,000×100) and 2.1% using pCTAB4.3 (32,600/1,530,000×100). However, complete removal of the T7 1.2 gene in the processed pCTAB4.3 case resulted in three times as many putative recombinant clones (1,530,000 vs. 493,000). The experiment was repeated four times using fresh preparations of the processed material with similar results, pCTAB4.3 consistently yielding 3–4 fold more recombinant clones than pCTA1 while maintaining a similar level of background. The decreased number of clones from pCTA1 indicates that the T7 1.2 gene of pCTA1 generates false negatives that cannot survive to form visible colonies. These false negatives are eliminated by removing the T7 1.2 gene from the final vector preparation, as in the pCTAB preparation. It is important to note that the direct selection function provided by the T7 1.2 gene is useful to reduce the background of uncut vector.

Additional variants of pCTH1.4 were constructed to replace the camR gene with other selectable markers. The primers pCmO-R TTT AGC TTC CTT AGC TCC (SEQ ID NO:53) and gp1.2-F: ATG CAA AGC TTG CAT GCC T (SEQ ID NO:54) were used in PCR, with pCTH1.4 as a template, to amplify a fragment consisting of all of pCTH1.4 except for the coding sequence of the camR gene. The camR promoter and translation initiation signals were retained in this PCR fragment ("pCmO1.2 fragment"), along with the origin of replication and all except five codons of 5' terminus of the T7 1.2 gene. The ampR coding region, beginning at the initiating ATG codon and lacking any promoter or 5' non-translated sequences, was amplified from pUC19 by the primers AmpF: ATG AGT ATT CAA CAT TTC C (SEQ ID NO:55) and Amp1.2R: ATG CAA GCT TTG CAT TTA CCA ATG CTT AAT CAG (SEQ ID NO:56). The genR coding region was amplified from pKGO with the primers Gen-F2: ATG TTA CGC AGC AGC AAC GAT IGTT ACG CAG CAG GGC AGT (SEQ ID NO:57) and Gen1.2-R ATG CAA GCT TTG CAT TTA GGT GGC GGT ACT TGG (SEQ ID NO:58). The kanR coding region was amplified from pACYC with the primers Kan-F: ATG AGC CAT ATT CAA CGG G (SEQ ID NO:59) and K1.2Sph-R: CTG CAG GCA TGC AAG CTT TGC ATT TAG AAA AAC TCA TCG AG (SEQ ID NO:60). Each of the resulting PCR products contained the five N-terminal codons of the T7 1.2 gene fused to the 3' terminus of the respective antibiotic gene. Each PCR fragment was treated with T4 DNA polymerase to generate blunt ends. The pCmO1.2 fragment was then ligated in the presence of T4 polynucleotide kinase and T4 DNA ligase to the ampR and genR PCR fragments to generate the plasmids pATH1 and pGTH2. The pCmO1.2 fragment was similarly ligated to kanR PCR fragment; however, no kanR clones were recovered.

Cells transformed with pUC19 or with other vectors containing the native ampR gene express a high amount β-lactamase, the product of the ampR gene that confers resistance to ampicillin. Because β-lactamase is secreted by host bacteria, it inactivates the ampicillin or carbenicillin in the medium surrounding colonies of cells transformed with such plasmids. Non-transformed bacteria present in this zone of inactivated antibiotic are able to grow, resulting in "feeder" or "satellite" colonies.

Placing the ampR coding sequence under control of the promoter from the camR gene was expected to lower expression of β-lactamase in transformants, thereby reducing the growth of the surrounding ampicillin sensitive cells. Following transformation of cells with the putative pATH1 ligation reaction, colonies surrounded by a low number feeder colonies were selected for further analysis. The plasmid contained in one of these colonies was purified and designated pATH1. Sequence analysis of pATH1 confirmed that the ampR coding sequence had been fused to the camR promoter as desired. However, the sequencing data also revealed that the ampR gene in pATH1 contained several point mutations. Subsequent transformation of cells with purified pATH1 and its derivatives confirmed that it produced significantly fewer feeder colonies than cells transformed with pUC19 (see Example 23).

EXAMPLE 9

Construction of Third Generation Direct Selection Multiplex Cloning Vector

Figure 15:
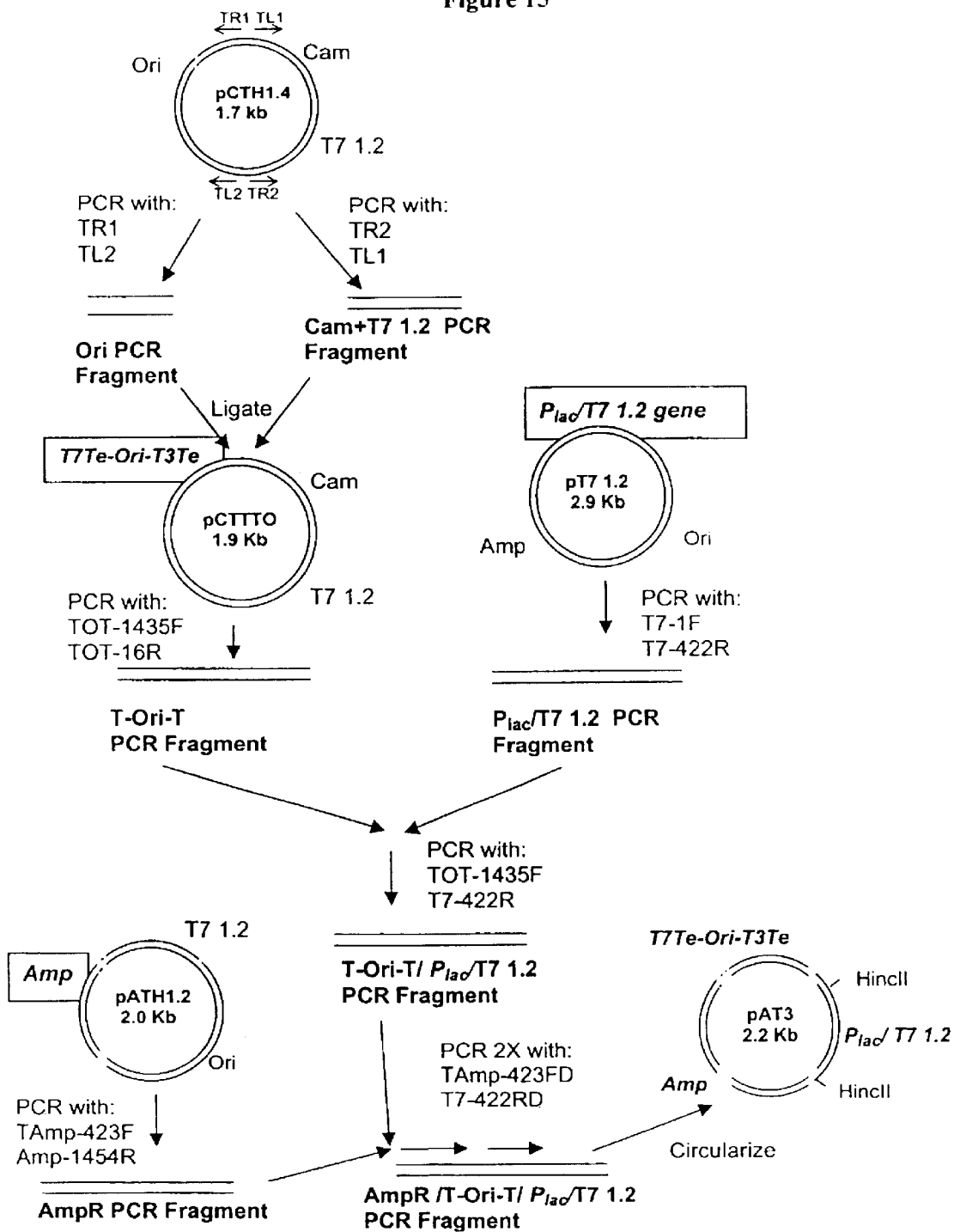
FIG. 15 shows construction of a third generation type direct selection vector.

This Example describes construction of third generation direct selection multiplex cloning vectors, which minimize vector-driven transcription into the insert DNA and insert-driven transcription into the vector. To avoid transcription of the insert DNA, the vector is configured such that transcription of the ampR coding sequence proceeds in a direction away from the cloning site. In addition, the ampR coding sequence is followed by a transcriptional terminator. No other promoters are present in the vector. A transcriptional terminator has also been placed on either side of the cloning site to block transcripts originating from within the insert DNA. The third generation multiplex cloning vector pAT3 was constructed by PCR (diagrammed in FIG. 15). The PCR primers used in this construction are as follows: TR1: CTG GCT CAC CTT CGG GTG GGC CTT TCT GCG TTG CTG GCG TTT TTC CAT (SEQ ID NO:61); TL1: TGT GAT TAC ATT TGG ACG CCT GTG AGC TTG AGG TTA ACG CTC CCT GCA GGA CCA (SEQ ID NO:62); TL2: CAC CTT CAC GGG TGG GCC TTT CTT CGG TAG AAA AGA TCA AAG GAT CTT CTT GAG (SEQ ID NO:63); TR2: AGC CAG TGA GTT GGT TAC AGT CCA GTT ACT CTC ACT GGA TGA TCG GCA CGT AAG AGG TTC CAA C (SEQ ID NO:64); TOT1435-F: GTA ATG AGG GCC CAA ATG TAA TCA CCT GG (SEQ ID NO:65); T7-1F: CCT GAA TGA TAT CAA GCT TGA ATT CGT TAA CGG CAC CCC AGG CTT TAC AC (SEQ ID NO:66); T7-422R: CTG ATT TAA ATG GTC AGT ATT GAG CGA TAT CTA GAG AAT TCG TCG ACT TAC TTC CAG TCC TTC AAC TGG (SEQ ID NO:67); TAmp423-F: TAC CTG ACC TCC ATA GCA GAA AGT CAA AAG CCT CCG ACC GGA GGC TTT TGA CTT GAT CGG CAC GTA AGA GGT TC (SEQ ID NO:68); Amp-1454R: CAT TTG GGC CCT CAT TAC CAA TGC TTA ATC AG (SEQ ID NO:69); TOT-1435F: GTA ATG AGG GCC CAA ATG TAA TCA CCT GG (SEQ ID NO:70); TOT-16R: CTT GAT ATC ATT CAG GAC GAG CCT CAG ACT CCA GTG AGC GTA ACT GGA CTG TAA TCA ACT CAC TGG (SEQ ID NO:71); TOT-16RD: CTT GAT ATC ATT CAG GAC GAG CC (SEQ ID NO:72); TAmp-423FD: TAC CTG ACC TCC ATA GCA GAA A (SEQ ID NO:73); T7-422RD: CTG ATT TAA ATG GTC AGT ATT G (SEQ ID NO:74).

As the first step in the construction of pAT3, PCR was used to insert the T3Te and T7Te transcriptional terminators into pCTH1.4 by amplification of pCTH1.4 with the primers TR1 and TL2 in one reaction and with the primers TR2 and TL1 in a second reaction. The resulting TR1/TL2 fragment contains the origin of replication from pCTH1.4, flanked by half of the T3Te terminator at one end and half the T7Te terminator on the other end. TR2/TL1 fragment contains the remaining portion of pCTH1.4, including the camR gene and T7 1.2 gene, flanked by the remaining half of the T3Te terminator at one end and the remaining half the T7Te terminator on the other end. The fragments were ligated to each other and transformed into DH10B cells. A plasmid containing the fragments ligated in the proper orientation to join the complementary portions of each terminator was designated pCTTTO-6. Sequence analysis of pCTTTO-6 revealed that it lacked a single base pair in the T7Te terminator region: however, the deletion was not in the stem-loop structure of the T7Te terminator that is considered critical to its function.

The primers TOT-1435F and TOT-16R were used to amplify a DNA fragment ("T-Ori-T" fragment) containing the T7 terminator, the origin of replication, and the T3 terminator from the plasmid pTTTO. This PCR was successful only upon lowering the annealing temperature of the reaction to 40° C. The T7 and T3 terminators in the T-Ori-T fragment are oriented such that they terminate transcripts entering from either side of this fragment. The pLac/T7 1.2 fragment, consisting of the lacZ promoter fused to the T7 1.2 gene was amplified from the plasmid pT7 1.2 by PCR with the primers T7-1F and T7-422R. The primer T7-1F shares 16 bases of homology with TOT-16R; thus, the 16 bp constituting the 3' end of the T-Ori-T fragment are identical to the 16 bp at the 5' end of the PLac/T7 1.2 fragment. The T-Ori-T and pLac/T7 1.2 fragments were gel purified, mixed, and added to the primers TOT-1435F and T7-422R in a PCR. The overlap present in these two fragments allows them to anneal to each other in the PCR. The resulting fusion of the two fragments is designated the "T-Ori-T-pLac/T7 1.2" fragment. A fragment containing the ampR coding region ("ampR" fragment") was PCR amplified from pATH1 with the primers TAmp-423F and Amp-1454R. Because the primers TAmp-1454R and TOT-1435F share 19 bases of homology, the 19 bp constituting the 3' end of the ampR fragment are identical to the 19 bp at the 5' end of the TOT fragment. The TOT-T7 and Amp fragments were gel purified, mixed, and added to the primers TAmp-423FD and T7-422RD in a PCR to create the fusion fragment "Amp-T-Ori-T-pLac/T7 1.2". This fragment was present as a faint band in the PCR products. It was gel purified and re-amplified with the same primers to generate a more intense band, which was gel purified, treated with T4 DNA polymerase, and circularized by self-ligation in the presence of T4 polynucleotide kinase and T4 DNA ligase. The T7 and ampR fragments each contained a portion of the TonB terminator, so the intact TonB terminator was formed at the junction of the two fragments. The ligated fragment was transformed into DH10B cells, and plasmid DNA was isolated from an ampicillin resistant colony.

As a functional test of the T7 1.2 gene, approximately 200 pg of intact pAT3 was transformed into DH10B (F-minus) and MC12 (F') cells. The DH10B cells are expected to show no selection against this plasmid, regardless of whether the T7 1.2 is expressed, since they lack the F plasmid required for selection. The MC12 cells are expected to show selection only when expression of the T7 1.2 gene is induced (e.g. by IPTG). The results indicated that the T7 1.2 gene functioned as expected. The DH10B cells yielded the approximately $5 \times 10^9$ colonies per ug of plasmid transformed, regardless of the presence of IPTG, which is the expected efficiency of transformation. The MC12 cells also gave about $5 \times 10^9$ colonies per ug of plasmid transformed when the cells were plated in the absence of IPTG, but only $2.5 \times 10^7$ colonies per ug transformed when the cells were plated in the presence of IPTG. Moreover, the MC12 colonies that grew in the presence of IPTG were significantly smaller than the DH10B transformants or the MC12 transformants that grew in the absence of IPTG, confirming the deleterious effects of expressing the T7 1.2 gene product.

Sequencing pAT3 revealed that the TonB terminator suffered a 6-bp deletion. The PCR primers LacO-F (5'-GAGCTGATAACAATTTCAGACAGGAAACAGCCA, SEQ ID NO:101) and TonB-R (5'-TCGGAGGCTTTTGACTTTCTGCTATGGAGGTCAGG, SEQ ID NO:108) were designed to amplify a fragment of pAT3 containing a portion of the lac promoter, the T7 1.2 gene, and a portion of the TonB terminator. This fragment incorporated changes in the lac operator that were expected to eliminate its function, resulting in constitutive expression of the T7 1.2 gene. It also restored the missing bases in the TonB terminator to restore its native sequence. The primers LacO-R (5'-ATAATTCCACACATTATACGAGCCGGAAGCATAAAG, SEQ ID NO:109) and TonB-F (5'-CCGGAGGCTTTTGACTTGATCGGCACGTAAGA, SEQ ID NO:118) amplified the remainder of the plasmid, incorporating additional mutations in the lac operator and the remaining part of the TonB terminator. These fragments were ligated to form the plasmid pAT4. Sequence analysis indicated that pAT4 carried the repaired TonB terminator and a mutated lac operator. Functional analysis of the T7 1.2 gene was performed as it was for pAT3. MC12 and DH10B cells were transformed with 200 pg of intact pAT4, and aliquots were spread on ampicillin plates with or without IPTG. The expected high transformation frequency of >10⁹ cfu/g was obtained in DH10B cells with or without IPTG. MC12 cells gave a transformation frequency of >10⁹ cfu/g without IPTG and approximately 10⁷ cfu/g with IPTG, indicating that the T7 1.2 gene was expressed only in the presence of IPTG, as in pAT3.

To create a constitutively active T7 1.2 gene, the primers LACdO-F (5' GGACTCGAGGGACGTTGCCTTACAG-GAAACAGCC
ATGGGA, SEQ ID NO:119) and LacO-R were used in a PCR to create a derivative of pAT3 that deleted the entire lac operator and replaced it with an XbaI restriction site. The resulting fragment was circularized to form the plasmid pAT5. Functional analysis of pAT5 was performed as it was for pAT3 and pAT4. The expected high transformation frequency of >10⁹ cfu/g was obtained in DH10B cells with or without IPTG. Likewise, MC12 cells also gave a transformation frequency of >10⁹ cfu/g with or without IPTG, indicating that the T7 1.2 gene was expressed constitutively in pAT5. Since pAT3 was the template for the PCR that created pAT5, the 6-bp deletion of the TonB terminator from pAT3 is present in pAT5. The primers TonB-F and TonB-R were used in a PCR to amplify a fragment from pAT5 that contained the intact TonB terminator. The fragment was re-circularized to form the plasmid pAT6-6. Functional testing of pAT6-6 indicated that the T7 1.2 gene was constitutively expressed, as it was in pAT5.

EXAMPLE 10

Construction and Use of Conditional Replication Vectors

As described in Example 3, the level of background colonies in multiplex cloning is greatly reduced by isolating the selectable markers from at least two independent partial source vectors. Nonetheless, as discussed in Example 5, there remains a detectable level of background colonies due to co transformation with both of the parental vectors. Example 5 illustrates that isolating selectable markers from a direct selection vector provides one means of decreasing this source of background. The present Example demonstrates that the background from dual parental transformants in a multiplex cloning reaction may be reduced by isolating at least one of the selectable markers from a conditional replication vector that can not grow in the same host as that used for transformation.

Figure 9:
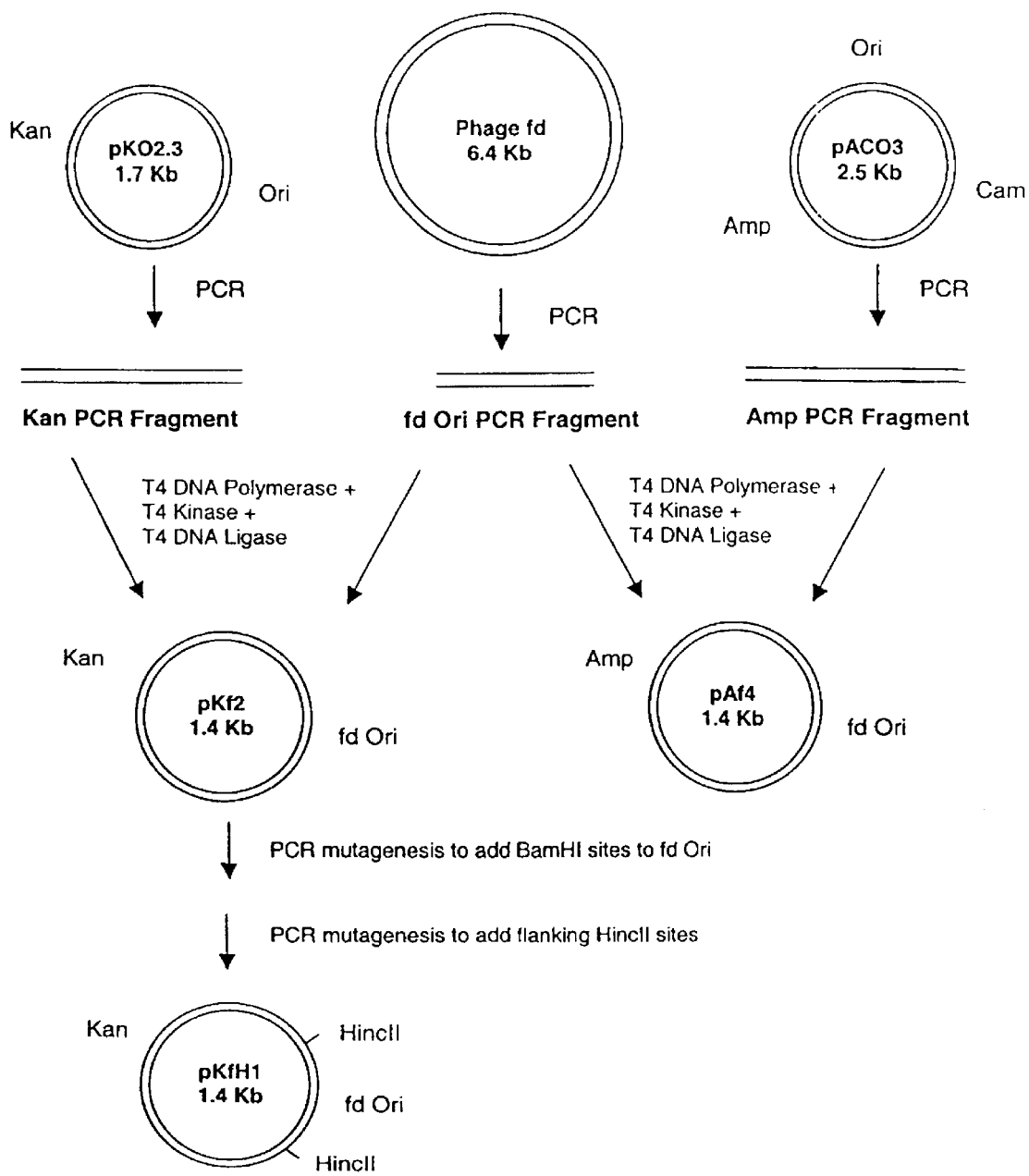
FIG. 9 shows the construction of conditional replication plasmids.

The replication origin of bacteriophage fd was used as the basis of the conditional replication plasmids diagramed in FIG. 9. Geider et al. (Gene 33:341–349, 1985) showed that approximately 300 bp of DNA from the intergenic region of bacteriophage fd is sufficient to act as an origin of replication in the presence of the fd gene 2 protein, the only viral product required for phage DNA replication. Plasmids containing the fd Ori can grow only in those E. coli strains engineered to express the bacteriophage fd gene 2 protein. One such strain such is BHB2600 (ATCC #47004).

The conditional replication vector pKP2 (FIG. 9) was constructed using the PCR amplified kanamycin gene plus TonB terminator from plasmid pKO2.3 (Example 3). The fd origin of replication was amplified from bacteriophage fd using the flanking oligonucleotide primers SSF1L2 (CTCTGAGAATTCATCTGCAGCTCGCCACGTTCGCC GGCTTTCCCCGTCA, SEQ ID NO:21) and SSF1R2 (TGCACGAATTCTTGCTGCAGTTGTAAACGTTAATA TTTTGTTAAAATTCGCGT, SEQ ID NO:22). The PCR fragments were end repaired with T4 DNA polymerase, phosphorylated using T4 kinase, ligated with T4 ligase, and transformed into BHB2600. The correct construct was identified by restriction analysis and the ability to transform kanamycin resistance to BHB2600 cells but not to DH10B cells, which lack the gene 2 protein.

To minimize the amount of unessential vector DNA in the final multiplex cloning preparation, a series of PCR mutagenesis steps were used to incorporate five additional restriction sites into pKf2. Two BamHI sites were sequentially added to the fd Ori in a series of constructions using the PCR primers SSBL12 TCCGTAAAGCACTAAATCG-GAACCCTAAAGGGAG (SEQ ID NO:42) and SSBR12 TCCTCGACCCCAAAAAACTTGATT-AGGGTGATGGTTCA (SEQ ID NO:43) and PCR primers SSBL4 CGAAAAACCGTCTATCAGGGCGATGGCCCA (SEQ ID NO:44) and SSBR4 GATCCCTTTGACGTTG-GATTCCACGTTCTTTAATAGTGGACTCTTGTTCCA (SEQ ID NO:45). The resulting plasmid was designated pKf4.8. These BamHI sites were added as a means to cleave the Ori fragment into small sub-fragments (less than 200 bp), to facilitate their removal from the Kan fragment by digestion followed by DE fractionation or PEG precipitation, as described in Example 8. Sequence analysis of pKfB4.8 revealed several mutations that were corrected in a PCR reaction using the primers K1203B-L: TCC GAA AAA CCG TCT ATC AGG GCG ATG GCC CA (SEQ ID NO:46) and K1203B-R: TCC CTT TGA CGT TGG AGT CCA CGT TGT TT (SEQ ID NO:47). An additional BamHI site was incorporated into the Ori sequence using the PCR primers B1310B-L: CTT TTG TCA TTT TCT GCT TAC TG (SEQ ID NO:48) and B1310-R: GAT CCT TAT AAA TCA AAA GAA TAG GCC GA (SEQ ID NO:49). The resulting plasmid was designated pKf7-1.

Subsequently, the PCR primers KHc1032R: TCA TGT TAA CCA GGA ATC TGG ATC CTG CAG CGC C (SEQ ID NO:50); KHc1047F: TAT AGT TAA CGC AGC TCG CCA CGT TCG CC (SEQ ID NO:51); KHp1399F: TAC TGT CGA CGC ATA TCT GGA TCC TGC AGC CGA TAC (SEQ ID NO:52); and KHp1384R: GGA GGT CGA CGC AGT TGT AAA CGT TAA TA (SEQ ID NO:17) were used to add HincII restriction sites to allow the option of excising the fd Ori from the Kan gene by HincII digestion, which leaves blunt ended fragments. The resulting construct, designated pKfH1, was confirmed by restriction analysis and DNA sequence analysis.

The TonB terminator is present in the pKf series of plasmids (e.g. pKf2, pKO2.3, pKf 4.8, pKfH1) and the pAT series of plasmids (e.g. pAT3, pAT-4, pAT-5, pAT-6, pATBst, pATR-G, pAR-G, and others). Consequently, duplex plasmids containing pKf and pAT vectors would have two copies of the TonB terminator. Since multiple copies of a DNA fragment within a plasmid may lead to instability (e.g. rearrangement or deletion), the TonB terminator of pKfH1 was replaced with the rrnB1 terminator. The primers KfR-990R: TCT TTC GAC TGA GCC TTT CGT TTT ATT TGA TTA GAA AAA CTC ATC GAG CAT C (SEQ ID NO:75) and KfR-991F: CTG AGC CTT TCG TTT TAA TCT GGA AAA ACC ACC CTG GCG CTG CAG GTT CCA GAT TCC (SEQ ID NO:76) were used in a PCR with pKfH1 as a template. The resulting fragment was re-circularized to generate the plasmid pKfHR.

The conditional replication vector pAf4 (FIG. 9) was constructed using the PCR amplified ampicillin gene from plasmid pACO3 described above. The fd origin of replication was amplified from bacteriophage fd using the flanking oligonucleotide primers ssf1L2 (SEQ ID NO:21) and ssf1R2 (SEQ ID NO:22). The PCR fragments were end repaired with T4 DNA polymerase, phosphorylated using, T4 kinase, ligated with T4 ligase, and transformed into BHB2600. The correct construct was identified by restriction analysis and the inability to transform DH10B cells to ampicillin resistance.

The present Example illustrates a duplex cloning experiment in which pCTAB4.3 (see FIG. 8) was digested with BglII and AvaII, dephosphorylated using thermosensitive alkaline phosphatase, and end-repaired using T4 DNA polymerase (abbreviated pCTAB/BATT in Table 14). The conditional replication vector pKf7.1 (see FIG. 9) was BamHI restricted, dephosphorylated, and end-repaired with T4 DNA polymerase (abbreviated pKf7.1/BTT in Table 12). These two vector preparations were mixed in equal molar amounts in the presence or absence of ligase and insert DNA. The total amount of vector DNA in the ligation reaction was 100 ng, and approximately one fifth of the reaction was used for transformation of $E.$ $coli$ DH5αF' cells. An aliquot was plated on TY agar plates containing cam plus kan to assay the background and efficiency of duplex cloning. Another aliquot was plated on cam alone to assay cloning into pCTAB alone. The results are shown in Table 12.

TABLE 12

Duplex cloning results using direct selection plus conditional replication vector preparations.

| Ligation reaction | Antibiotic plate | # Colonies/ml transformation |
|---|---|---|
| pCTAB/BATT + pKf7.1/BTT − ligase | cam + kan | 0 |
| pCTAB/BATT + pKf7.1/BTT − ligase | cam | 14 |
| pCTAB/BATT + pKf7.1/BTT + ligase | cam + kan | 0 |
| pCTAB/BATT + pKf7.1/BTT + ligase | cam | 380 |
| pCTAB/BATT + pKf7.1/BTT + λRsaI + ligase | cam + kan | 7,200 |
| pCTAB/BATT + pKf7.1/BTT + λRsaI + ligase | cam | 440,000 |

The pCTAB/BATT+pKf7.1/BTT−ligase reaction is a control containing only the selectable marker fragments to test the degree of empty vector background contamination. The background of intact pCTAB vector alone is observed on the cam only plates, whereas no background is detectable on cam plus kan plates. The pCTAB/BATT+pKf7.1/BTT+ligase is a control to test the efficiency of dephosphorylation to inhibit direct ligation of the selectable markers. Plating this reaction on cam alone reveals the low background due to pCTAB self ligation, which is less than 0.1% (380/440,000). The lack of colonies when plated on cam plus kan demonstrates that neither partial source nucleic acid is capable of producing background colonies. This Example demonstrates the use of a direct selection vector and a conditional replication vector to provide the components of a complete duplex cloning vector mix, which is capable of reducing background transformation to an undetectable level.

This duplex cloning experiment resulted in approximately 7240 recombinant clones. The ratio of empty vector versus recombinant plasmid colonies was less than 0.01% (1/7200× 100). Although no colonies were detected on the cam plus kan plates from the empty vector control reaction (pCTAB/BATT+pKf7.1/BTT+ligase), the number 1 was used in this calculation to approximate the maximum likely frequency.

EXAMPLE 11

Sequence Analysis of a Lambda DNA Multiplex Clone Library

Figure 10:
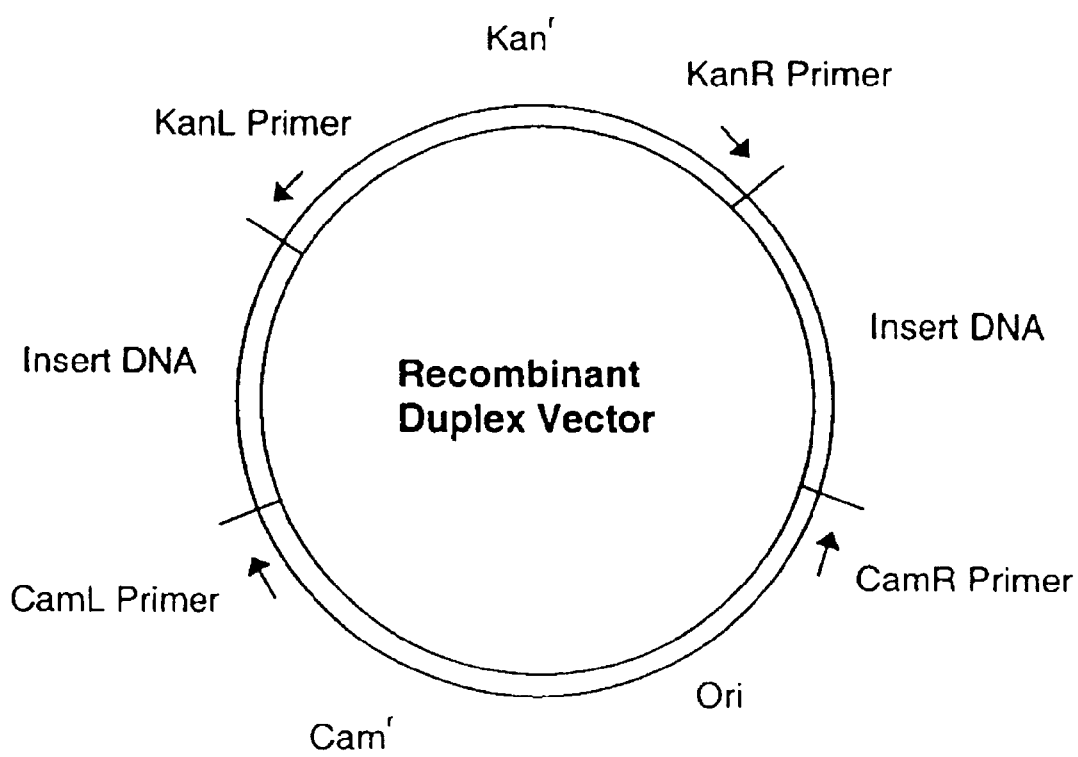
FIG. 10 shows the structure of certain recombinant duplex plasmid clones.
Figure 13:
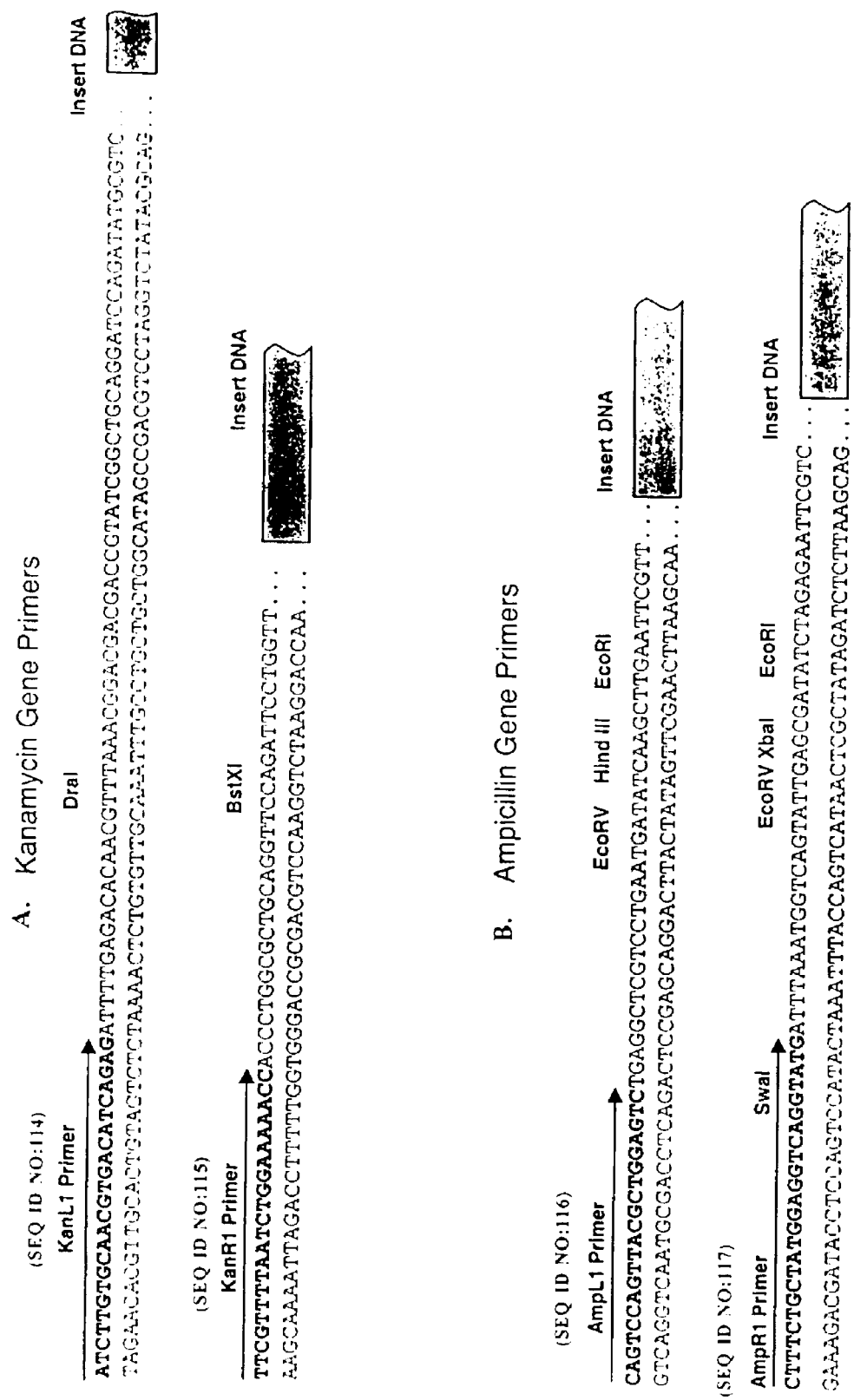
FIG. 13 shows the sequence of the primers (KanL1, SEQ ID NO:114; KanR1, SEQ ID NO:115; AmpL1, SEQ ID NO:116; and AmpR1, SEQ ID NO:117) configured for use with the vector components shown in FIGS. 12A and 12B.

The desired structure of recombinant plasmid clones produced in a duplex cloning experiment, such as that described in Example 10, is a circular DNA molecule consisting of two segments of insert DNA separated by the Kan selectable marker on one side and the Cam plus Ori marker on the other side (FIG. 10). The multiplex sequencing primers KanL4 (KAN-L4: ATC TTG TGC AAC GTG ACA TCA GAG, SEQ ID NO:23) and KanR2 (KAN-R2: CAG AAA GTC AAA AGC CTC CGA C, SEQ ID NO:24) are situated within the Kan marker such that they prime sequencing reactions that read the DNA adjacent to this marker. These primers are designated KanL and KanR in FIG. 10. Similarly, the CamL (CamL: CAG TAC TGC GAT GAG TGG CAG, SEQ ID NO:25) and C1178R (C1178R: GAT TTT TGT GAT GCT CGT CAG G, SEQ ID NO:26) primers are situated within the Cam plus Ori marker such that they prime sequencing reactions that read the DNA adjacent to this marker. These primers are designated CamL and CamR in FIG. 10. Therefore, in a recombinant plasmid assembled in the desired manner, all four of these primers are expected to yield DNA sequence reactions corresponding to insert DNA.

To confirm that the multiplex cloning scheme generated the desired recombinant plasmid constructs, 50 randomly picked clones from Example 9 were sequenced with each of the four sequencing primers described above. The colonies were grown in 2 ml of Terrific Broth at 37° C. overnight, the DNA was purified by alkaline lysis treatment, and each clone was subdivided into four reactions, one for each of the sequencing primers. The four resultant DNA sequences from each clone were compared to that of the known intact lambda DNA (GenBank Accession Number J02459) using the BLAST program of the NCBI (Lipman et al., PNAS, USA, 86:4412, 1989). Analysis of all 200 DNA sequences (50 clones sequenced using 4 flanking primers) revealed a 100% frequency of λ RsaI inserts at each of the cloning sites, a 0% frequency of empty insertion sites, and a 0% frequency of multiple marker inserts. As expected, many of the insert DNA segments consisted of multiple independent λ RsaI fragments ligated into a larger fragment, reflecting the small size and large number of λ RsaI fragments in the reaction. Significantly, vector DNA was not detected in any of the inserts. Thus, the duplex cloning experiment in Example 10 produced the desired experimental results of one foreign insert in each of two cloning sites in 100% of the recombinant clones.

EXAMPLE 12

Multiplex (Triplex) Cloning with Second Generation Direct Selection Vectors and Conditional Replication Vectors This Example describes triplex cloning with second generation direct selection vectors and conditional replication vectors. In particular, pCTA1 (see in FIG. 8) was digested with AvaII, dephosphorylated using thermosensitive alkaline phosphatase, and end-repaired using T4 DNA polymerase (abbreviated pCTA1/ATT in Table 13). pCTA1/TAA was mixed with the conditional replication vectors pAf4 and pKf2 that had been BamHI restricted, dephosphorylated, and end-repaired with T4 DNA polymerase (pAf4/BAT and pKf2/BAT, respectively). The amount of vector DNA in the ligation reaction was 200 ng, and approximately one fifth of the reaction was used to transform $E.$ $coli$ DH5αF' cells. An aliquot of the transformed cells was plated on TY agar plates containing cam plus kan. The results of this assay are presented in Table 13.

TABLE 13

Multiplex cloning using direct selection and conditional replication vectors.

| Ligation rx | # colonies/ ml transformation |
|---|---|
| pCTA1/ATT + pAf4/BAT + pKf2/BAT + ligase | 0 |
| pCTA1/ATT + pAf4/BAT + pKf2/BAT + λRsaI + ligase | 7600 |

The results presented in Table 13 indicate that this assay resulted in 7600 putative recombinant clones with no detectable background. Thus, the frequency of empty vector versus insertion ligation events was less than 0.01% (1/7600×100). Although no colonies were observed in the absence of insert DNA, the number 1 was used to estimate the maximum likely frequency.

The frequency of multiple selectable marker insertion events was estimated by restriction analysis using the unique eight base restriction site associated with each selectable marker. The results of this analysis indicated that 11/64 or 17.2% of the clones had multiple inserts. These 11 multiple inserts would render 22 sequence reactions unreadable, representing 5.700 of the 384 possible reactions (64 clones×6 reactions per clone).

EXAMPLE 13

Multiplex Sequencing from a Multiplex Cloning Vector

This Examples describes multiplex sequencing from a multiplex cloning vector. A 7.0 kb plasmid, pACR4 (See e.g. Example 7) was isolated and combined with 6 primers in a fluorescent dye-terminator cycle sequencing reaction. The table below lists the primers used, the general location of their binding sites, and the results obtained from automated sequence analysis. The results are presented as either single peaks, meaning clear sequence data was obtained, or multiple peaks, indicating the lack of interpretable results.

TABLE 14

Multiplex sequencing primers and results from sequencing electropherograms.

| Sequence reaction | Primer(s) | Streptavidin Purified | Primer Location | Peaks |
|---|---|---|---|---|
| Sample 1 | All 6 primers | No | Various locations | Multiple |
| Sample 2 | All 6 primers | Yes | Various locations | Single |
| Sample 3 | Biotin forward | No | 3' of pUC19 MCS | Single |
| Sample 4 | AMPL6 | No | 5' end of amp gene | Single |
| Sample 5 | PST CW | No | middle amp gene | Single |
| Sample 6 | PST CCW | No | middle amp gene | Single |
| Sample 7 | CML6 | No | 5' end of cam gene | Single |
| Sample 8 | Reverse | No | 5' of pUC19 MCS | Single |

The Applied Biosystems AmpliTaq FS DNA polymerase and rhodamine dye terminator chemistry were used in this experiment. One of the 6 primers contained a biotin at the 5' end ("Biotin forward" in Table 16). After the cycle sequencing reaction, streptavidin-coated paramagnetic beads and high salt binding buffer were added to bind the single modified primer. The reaction tube was placed in a magnetic field, the unbound material was aspirated, and the bound material was washed with a low salt buffer. The purified material was analyzed on an Applied Biosystems 373A DNA sequencer.

The mixture of six primers in a single sequencing reaction resulted in numerous overlapping peaks and unintelligible data when loaded onto a single lane. In contrast, the streptavidin-captured product from the "Biotin forward" primer in the same six primer reaction mix yielded well resolved peaks and intelligible data. These results clearly demonstrate the feasibility of co-sequencing multiple DNA fragments from a single multiplex vector.

EXAMPLE 14

Multiplex Cloning with Two Vector Components

This Example describes multiplex cloning using the direct selection vector pAT6-6 and the conditional replication vector pKfR. Vector components were prepared by digesting pAT6-6 with restriction enzymes HincII and StyI and digesting pKfR with restriction enzymes HincII and Sau96I. The reactions were extracted with five volumes of 6M guanidine and 100 mM Tris pH 6.5, adsorbed to diatomaceous earth, and washed with 0.4 M NaCl, 20 mM Tris pH 7.5, 0.5 mM EDTA, and 50% ethanol. The restriction fragments were eluted with distilled water, and the vector components were differentially precipitated with 7% PEG8000 and 10 mM $MgCl_2$. The fragments were dephosphorylated by treatment with calf intestinal phosphatase, extracted with phenol and chloroform, and precipitated again with PEG 8000 and $MgCl_2$. The processed vector components are designated pAT66/HSC (SEQ ID NO:85) and pKfR/HSC (SEQ ID NO:86), respectively (See, FIG. 12B and FIG. 14). Insert DNA was prepared by digesting phage lambda DNA with HincII and purifying with guanidine and diatomaceous earth. After precipitation with PEG8000 and $MgCl_2$, and the fragments were dissolved in distilled water.

Approximately equal molar amounts of the two vector components (185 µg of pAT66/HSC and 115 µg pKfR/HSC) were ligated with 500 µg of lambda/HincII fragments. Control reactions contained the vector components ligated without insert DNA or mixed without ligase or insert DNA. One-tenth of the ligation reactions were transformed into MC12 cells, and aliquots were plated onto agar plates containing carbenicillin or ampicillin plus kanamycin. The results are shown in Table 15.

TABLE 15

Duplex cloning results using direct selection plus conditional replication vector preparations.

| Ligation reaction | Antibiotic plate | # Colonies/ ml transformation |
|---|---|---|
| pAT66/HSC + pKfR/HSC − ligase | amp + kan | 0 |
| pAT66/HSC + pKfR/HSC + ligase | amp + kan | 5 |
| pAT66/HSC + pKfR/HSC + λHcII + ligase | amp + kan | 7,600 |
| pAT66/HSC + pKfR/HSC − ligase | carb | 60 |
| pAT66/HSC + pKfR/HSC + ligase | carb | 700 |
| pAT66/HSC + pKfR/HSC + λHcII + ligase | carb | 1,500,000 |

This cloning experiment resulted in approximately 7600 recombinant duplex clones and 1,500,000 recombinant single-insert clones. The pAT66/HSC+pKfR/HSC−ligase reaction is a control containing only the selectable marker fragments to test the degree of empty vector background contamination. The background of intact pAT6-6 vector, which is observed on the carb only plates, was less than 0.004% (60/1,500,000), whereas no background was detectable on amp plus kan plates. The pAT66/HSC+pKfR/HSC+ ligase is a control to test the efficiency of dephosphorylation in inhibiting direct ligation of the selectable markers. Plating this reaction on carb alone reveals the low background due to pAT6-6 self ligation, which is less than 0.05% (700/1, 500,000). The small number of colonies recovered on amp plus kan demonstrates that the level of pAT66/HSC ligation to pKfR/HSC was less than 0.07% (5/7600×100). This Example demonstrates the use of a direct selection vector and a conditional replication vector to provide the components of a complete duplex cloning vector mix, which is capable of reducing background levels in transformation to extremely low levels.

EXAMPLE 15

Construction of a Fixed Orientation Multiplex Cloning Vector

The present Example describes fixed orientation multiplex cloning, in which two vector fragments are assembled in a defined orientation relative to each other upon ligation with two insert DNA fragments. The vector pATBAG was constructed by first amplifying the T7 1.2 gene from pAT6-6 with the primers BXTLGA: AAC CAT AAA ATT GGC ACC CCA GGC TTT ACA CTT TAT GCT (SEQ ID NO:77) and BXTRGG: GAC CCA CGG GGC TGG TTA CTT CCA GTC CTT CAA CTG GTC ATA CA (SEQ ID NO:78). The resulting fragment, containing a T7 1.2 gene flanked by BstXI cloning sites, was cloned into a preparation of pAT66/HSC, generating the intact pATBAG vector. The vector pKfRBAG was constructed by first amplifying the fd replication origin of pKfHR with the primers KBst-1053F 5'-AACCCACGGGGATGGGC AGCTCGCCACGT-TCGCCGGCTT (SEQ ID NO:79) and KBst-1433R 5'-GACCATAAAA CTGGGCAGTTGTAAACGT-TAATATTTTG (SEQ ID NO:80). The resulting fragment, containing the fd replication origin flanked by BstXI cloning sites, was cloned into a preparation of pKfR/HSC, generating the intact vector pKfRBAG. Preparations of pATBAG and pKfRBAG were digested with the restriction enzymes StyI and Sau96I, respectively, and further digested with the restriction enzyme BstXI. The resulting fragments were treated with calf intestinal phosphatase to generate the vector components ATBAG/BSC and KfBAG/BSC. The ATBAG/BSC and KfRBAG/BSC vector components each have a four bp extension of . . . GGGG-3' on one end and . . . AAAA-3' on the other end (See FIG. 16B).

Insert DNA for fixed orientation multiplex cloning was generated from bacteriophage lambda DNA. The DNA was fragmented by hydrodynamic shearing and aliquotted into two pools. One pool of DNA fragments was ligated to the "C4" double-stranded linker, which has one blunt end and one 3' overhang of CCCC. The C4 double-stranded linker was generated by annealing the primers NotC4-Lnk: AGC GGC CGC AGA CTT GCC TGA CCA TTG ACC CC (SEQ ID NO:81) and Not-comp: TCA ATG GTC AGG CAA GTC TGC GGC CGC T (SEQ ID NO:82). A second pool of DNA fragments was ligated to the "T4" double-stranded linker, which has one blunt end and one 3' overhang of TTTT. The T4 double stranded linker was generated by annealing the primers Not4T-Lnk: AGC GGC CGC AGA CTT GCC TGA CCA TTG ATT TT (SEQ ID NO:83) and Not-comp (SEQ ID NO:82).

After ligation to the linkers, insert DNA fragments were fractionated by agarose gel electrophoresis to purify fragments of 2–4 kb and to remove fragments of other sizes, including un-ligated and self-ligated linkers. The insert fragments were purified from the agarose gel and ligated to the ATBAG/BSC and KfBAG/BSC vector components. The ligation reactions were transformed into MC12 cells, and transformants were selected on plates containing ampicillin and kanamycin. A total of approximately 650 transformants per ml of transformed cells were recovered. Analysis of 11 clones indicated that all had inserts of the same size. Sequence analysis of 2 of these inserts showed that the inserts were in fact identical to the sequence of the fd origin portion of the pKfRBAG vector. These clones were therefore likely to be derived from incomplete digestion of this vector, rather than to actual ligation of the fd origin segment to the ATBAG/BSC and KfBAG/BSC vector components.

This demonstration illustrates the use of a particular set of vector termini (i.e. AAAA-3' and GGGG-3') and insert termini (i.e. TTTT-3' and CCCC-3'), which may not be optimal for efficient ligation. A wide variety of other termini may be used, which conform to the general configuration for fixed orientation multiplex cloning depicted in FIG. 16B of this Example or in FIG. 16A. Such termini need not be limited to 3' extensions, to extensions of exactly four bases, nor to poly-A, poly-T, poly-C, or poly-G extensions. The following vector components and insert fragments were created to demonstrate the use of alternate termini for fixed orientation multiplex cloning.

The vector component ATBbs was constructed by amplifying the ampR gene, replication origin, and terminators of ATBAG/BSC with the primers ATBB-1F GCACCTGAC-CTCCTGTGTCTTCGACGAATTCTCTA-GATATCGCTCAA (SEQ ID NO:120) and ATBB-1845R: GCAATGGTCTGTCGCCGTCTTCAAC-GAATTCAAGCTTGATATCATTCAGGA (SEQ ID NO:121). The resulting fragment was digested with the restriction enzyme BbsI, generating ATBbs. ATBbs is analogous to ATBAG/BSC and pAT66/HSC, except that the termini of ATBbs have an extension of 5'-TCCT on one end and 5'-GTCG on the other end. The vector component KBsa was constructed by amplifying the kanR gene and terminator of KfBAG/BSC with the primers KBS-1F: GGACCTG-CAAGTCGGGAGACCGACGCATATCTGGAT CCTG-CAGCCGATAC (SEQ ID NO:122) and KBS-1073R: GGAATCCTGGTCCTCGAGACCAACCAG-GAATCTGGAACCTGCAGCGCCA (SEQ ID NO:123). The resulting fragment was digested with the restriction enzyme BsaI, generating the vector component KBsa. KBsa is analogous to KfBAG/BSC and pKfR/HSC, except that the termini of KBsa have an extension of 5'-TCCT on one end and 5'-GTCG on the other end. These termini are the same as those on ATBbs, but they are not compatible with each other or with those of ATBbs, preventing the vector components from being ligated to each other.

One of the insert DNA fragments for fixed orientation multiplex cloning was generated by PCR amplification of the lacZ gene fragment of pUC19 DNA, using the primers LacBS-1F: GGTACTTATCAGGACGAGACCCATTAG-GACCCCAGGCTTTAC (SEQ ID NO:124) and LacBS-340R: GGTCTATTAGAGGACGAGACCTTAGCGC-CATTCGCCATTCAGGCT (SEQ ID NO:125). The resulting fragment was digested with the restriction enzyme BsaI, leaving an extension of 5'-AGGA on each end. This fragment, designated LacBS, can therefore be ligated to the 5'-TCCT extension on one end of either ATBbs or KBsa.

A second pool of DNA insert fragments was generated by amplification of the gentR gene of pKGO (see FIG. 6) with the primers GenBS-1F: GGAACTTCGACGACCGAGAC-CAATTGACATAAGCCTGTTCGGTT (SEQ ID NO:126) and GenBS-765R: GTGTACAATGCGACCGAGACCT-TAGGTGGCGGT ACTTGGTCGAT (SEQ ID NO:127).

The resulting fragment was digested with the restriction enzyme BsaI, leaving an extension of 5'-CGAC on each end. This fragment, designated GenBS, can therefore be ligated to the 5'-GTCG extension on one end of either ATBbs or KBsa.

A 10-ul ligation reaction was performed containing approximately equal molar amounts of ATBbs, KBsa, LacBS, and GenBS. The amount of each DNA fragment in the ligation reaction was approximately 270 ng, 150 ng, 105 ng, and 45 ng, respectively. One tenth of the reaction was used to transform MC12 cells, which were spread on agar plates containing ampicillin and kanamycin (amp+kan); or onto plates containing kanamycin, gentamycin, X-Gal, IPTG, and ampicillin (KGXIA); or onto plates containing kanamycin, gentamycin, X-Gal, and IPTG (KGXI). The amp+kan plates select for any plasmids containing both vector fragments. The KGXIA plates select for plasmids containing both vector components as well as the GenBS insert. They allow for visual screening of the presence of the LacBS insert. The KGXI plates select for the KBsa vector component as well as for the GenBS insert, but they do not select for the ATBbs component. They also allow for visual screening of the presence of the LacBS insert. A control ligation reaction containing only the vector components was also performed. Following overnight incubation at 37° C., the following results were observed Table 16):

TABLE 16

Fixed orientation multiplex cloning.

| Ligation reaction | Plate | # Colonies/ml transformation |
|---|---|---|
| ATBbs, KBsa + ligase | amp + kan | 0 |
| ATBbs, KBsa, LacBS, GenBS + ligase | amp + kan | 350,000 (blue) |
| ATBbs, KBsa, LacBS, GenBS + ligase | KGXIA | 150,000 (blue) |
| ATBbs, KBsa, LacBS, GenBS + ligase | KGXI | 150,000 (blue) |

The results of the ATBbs, KBsa+ligase reaction presented in Table 16 indicate that there was no background due to self-ligation of the vector components. In contrast, ligation of all four fragments (ATBbs, KBsa, LacBS, GenBS), produced 350,000 colonies per ml of transformed cells. This reaction was therefore over 46-fold more efficient than the previously described multiplex cloning reaction employing blunt dephosphorylated ends (Example 14). Plating on KGXIA resulted in 150,000 colonies per ml. These colonies all must have contained both the LacBS and the GenBS insert fragments, since they were blue and resistant to gentamycin. The reduced number of colonies relative to the amp+kan result may reflect a deleterious effect of selection for triple antibiotic resistance in addition to expression of the lacZα peptide. Plating on KGXI likewise produced 150,000 blue colonies per ml, indicating that selection for both vector components was not necessary. The configuration of the ends of the vector components and the insert fragments allowed formation of a circular plasmid only by ligation of all four DNA sequences in the order ATBbs-GenBS-KBsa-LacBS (with the LacBS fragment being further ligated to the ATBbs component to form a circle), as follows:

```
            ATBbs
   LacBS            GenBS
            KBsa
```

Since inclusion of the vector components is necessitated by the configuration of the ends of the insert fragments and vector components, the vector components serve to supply sequencing primer binding sites and to separate individual insert DNA fragments from each other.

PCR amplification plus BsaI digestion of specific insert fragments was employed to generate the sticky ends in the present demonstration. For more general applications (e.g., construction of shotgun libraries), this limitation may be circumvented by appending double-stranded oligonucleotide linkers to blunt-ended insert pools, similar to addition of C4 and T4 linkers to sheared lambda DNA in the initial ligations described in this Example. For example, insert DNA is fragmented by hydrodynamic shearing and aliquotted into two pools. One pool of DNA fragments is ligated to the "AGGA" double-stranded linker, which has one blunt end and one 5' overhang of AGGA. The AGGA double-stranded linker is generated by annealing the primers AGGA-Lnk: AGC GGC CGC AGA CTT GCC TGA CCA TTG AAG GA (SEQ ID NO:128) and Not-comp (SEQ ID NO:82). A second pool of DNA fragments is ligated to the "CGAC" double-stranded linker, which has one blunt end and one 5' overhang of CGAC. The CGAC double stranded linker is generated by annealing the primers CGAC-Lnk: AGC GGC CGC AGA CTT GCC TGA CCA TTG A CGA C (SEQ ID NO:[129]84) and Not-comp (SEQ ID NO:82). After ligation to the linkers, insert DNA fragments are fractionated by agarose gel electrophoresis to purify fragments of a desired size range (e.g., 2–4 kb) and to remove fragments of other sizes, including un-ligated and self-ligated linkers. The insert fragments are purified from the agarose gel and ligated to vector components (e.g., ATBbs and KBsa) that have one end compatible to each pool of insert DNA fragments. The ligation reactions are transformed into MC12 cells, and transformants are selected on plates containing ampicillin and kanamycin. The number of insert fragment pools and vector components is not limited by the availability of selectable markers, since the vector components and insert fragments can be configured to permit formation of a closed circular plasmid only by ligation of a particular insert fragment between two particular vector components, the said insert fragment acting as a "bridge" between the two said vector components.

For cloning fragments of known sequence, the fixed orientation multiplex cloning vector can be further adapted to clone the inserts as well as the vector components in a defined orientation. For example, PCR may be used to append a unique 5' extension onto one end of an insert fragment and a different unique 5' onto the other end of the insert fragment. Likewise, a complementary unique 5' extension can be appended onto each end of two vector components, such that the insert end can bind only to these two vector components in a defined orientation. Additional inserts and vector components are likewise configured to allow assembly in a defined order, with each vector component and insert fragment in a defined orientation. After ligation and transformation, all the resulting recombinant plasmids will have an identical structure. Such a set of vector components would be particularly useful for fixed orientation expression multiplex cloning, as the vector components would have promoter regions near their termini to drive expression of insert fragments. Therefore, inserts fragments would need to be ligated in the proper orientation for expression. Further, if there are multiple different promoters present among the circular recombinant plasmid, the insert fragments would need to be ligated adjacent to a particular promoter of a particular vector component, to allow one to know which promoter will drive expression of that insert fragment. In addition, the final recombinant plasmid should be such that all promoters are oriented in the same direction (e.g., such that all transcription proceeds clockwise around the plasmid).

EXAMPLE 16

Multiplex Cloning by Dual Transformation with Independent Vectors

This Examples describes the use of multiple independent vectors to effect multiplex cloning. In this case, two vectors function as conventional single-insert cloning vectors that are co-transformed into competent cells. The vectors contain different antibiotic resistance genes, as well as identical origins of replication which are functional in the cells to be transformed. Insert DNA is cloned into each vector to form pools of recombinant circular plasmids. The recombinant plasmids formed from each vector are simultaneously transformed into competent cells. Cells are plated on media containing two antibiotics, thereby selecting for transformants that took up both vectors. Typically less than 1% of the intact DNA molecules capable of transformation are successful in generating a transformant, so the frequency of the desired dual transformation is extremely small. Further, it is generally accepted that plasmids with similar origins of replication are "incompatible," i.e. cannot co-exist stably within the same cell.

The vectors pCTAB and pATH were used to demonstrate the feasibility of dual transformation. Approximately 10 ng each of the intact vectors were mixed and used to transform MC12 cells. Transformants were selected by plating on cam alone to measure the frequency of transformation with pCTAB or on cam plus carb to measure the frequency of dual transformation. Approximately 1,000,000 pCTAB transformants were obtained on cam plates, and about 80,000 dual transformants were obtained on cam plus carb. Therefore, with intact plasmids the frequency of dual transformation w%as approximately 12-fold lower than the frequency of single transformation.

Multiplex cloning with recombinant libraries was demonstrated by separately ligating lambda/HincII DNA to either pCTAB/BATT or pATH/HSC. Approximately 500 ng of lambda/HincII DNA was ligated to approximately 100 ng of each vector. The ligations were mixed, and 1 μl was transformed into MC12 cells. Aliquots were spread on cam, carb, or cam+carb plates. The number of colonies on the cam plate and on the carb plate each corresponded to 1,800,000 colonies per ml transformed cells. The cam+carb plate represented 2300 colonies per ml, approximately 800 fold lower than the number of single-plasmid transformants. This Example illustrates that dual transformation can be used to achieve multiplex cloning, although the frequency is significantly lower with ligation reactions than with intact purified plasmids. Dual transformation has the disadvantage that the relative plasmid copy number of the two plasmids may vary among different recombinant clones or among various cultures of a single clone.

TABLE 17

Multiplex cloning by dual transformation of MC12 cells

| Transformation reaction | # Colonies/ml transformation | | |
|---|---|---|---|
| | cam | carb | cam + carb |
| pCTAB + pATH | 1,000,000 | n.d. | 80,000 |
| pCTAB/BATT + λHcII + ligase and pAT66/HSC + λHcII + ligase | 1,860,000 | 1,800,000 | 2300 |

EXAMPLE 17

Use of pAT6-6 as a Single-Insert Cloning Vector

This Examples describes the use of pAT6-6 as a low-background, highly efficient vector for cloning one fragment of DNA per vector. Further, it illustrates the advantages of using a vector containing terminators flanking the cloning site, such as pAT6-6, for cloning genomic DNA of *Lactobacillis helveticus,* which is AT-rich (i.e. has a relatively low GC-content). A preparation of pAT6-6 was digested with HincII and StyI restriction enzymes, which excises the T7 1.2 gene as two fragments. The T7 1.2 gene fragments were removed by differential precipitation of the larger vector fragment with 7%o PEG8000 and 10 mM $MgCl_2$. The vector fragment was then treated with calf intestinal phosphatase and purified by phenol/chloroform extraction and ethanol precipitation. Fifty ng of this vector preparation (designated pAT66/HSC-a, SEQ ID NO:85, see FIG. 12A and FIG. 14A) was ligated to 500 ng of HincII-digested lambda DNA, self-ligated in the absence of insert DNA, or added to ligase buffer without insert DNA or ligase. One-tenth of each reaction was transformed into MC12 cells or DH10B cells, and aliquots were plated on carbenicillin plates. The experiment was repeated with two separate preparations of pAT66/HSC-a, with very similar results. The average of the two results is shown in Table 18.

TABLE 18

Single-insert cloning with pAT66/HSC in MC12 or DH10B cells

| Ligation reaction | Cell type | # Colonies/ ml transformation |
|---|---|---|
| pAT66/HSC-a – ligase | MC12 | 5 |
| pAT66/HSC-a + ligase | MC12 | 0 |
| pAT66/HSC-a + λHcII + ligase | MC12 | 181,000 |
| pAT66/HSC-a – ligase | DH10B | 2800 |
| pAT66/HSC-a + ligase | DH10B | 100 |
| pAT66/HSC + λHcII + ligase | DH10B | 100,000 |

The results shown in Table 18 indicate that the pAT66/HSC-a preparations gave extremely low backgrounds of uncut vector (5/181,000 or 0.003%) or self-ligated vector (0/181,000 or 0%) when transformed into MC12 cells, which provide selection against intact pAT66 vector molecules. When transformed into DH10B cells, which do not provide selection against intact pAT66 vector molecules, these pAT66/HSC-a preparations yielded low, but significantly higher, backgrounds of uncut vector (2800/100,000 or 2.8%) or self-ligated vector (100/100,000 or 0.1%). The higher backgrounds seen with transformation of DH10B cells demonstrates the utility of the T7 1.2 gene in selecting against uncut vector molecules. Observing fewer colonies from self-ligated vector than from unligated vector implies that the presence of ligase decreases the efficiency of transformation. This observation is not novel, but reasons for the decrease are not known.

The preparation of pAT66/HSC-a was further treated with HincII, SnaBI (which cuts within the T7 1.2 gene, near the StyI site), and calf intestinal phosphatase. Fifty ng of this preparation, designated pAT66/HSC (SEQ ID NO:85), was tested by ligation to lambda/HcII DNA, by self-ligation, or with no ligation. Ligation and transformation conditions were similar to those employed previously with pAT66/HSC-a (See Table 18 above). One-tenth of each reaction was used to transform DH10B cells, and aliquots were spread on plates containing ampicillin or carbenicillin. The self-ligated and un-ligated background levels were greatly reduced, although the background level due to self-ligated vector was still significantly higher than that observed previously with MC12 cells. The results are listed in Table 19.

TABLE 19

Transformation of DH10B cells with extensively processed pAT66 vector.

| Ligation reaction | Cell type | # Colonies/ ml transformation |
| --- | --- | --- |
| pAT66/HSC – ligase | DH10B | 0 |
| pAT66/HSC + ligase | DH10B | 80 |
| pAT66/HSC + λHcII + ligase | DH10B | 200,000 |

The results shown in Table 19 indicate the background due to uncut vector was 0% and due to self-ligated vector was 0.04% (80/200,000).

AT-rich DNA fragments can act as transcriptional promoters in bacteria, initiating transcription into the vector sequence, which may interfere with vector replication or expression of drug resistance from the vector. The AT content of the Lactobacillus genome is approximately 65%; therefore, it is possible that the lower transformation efficiency observed with the pUC/HC vector is due to plasmid instability caused by transcription initiated by the L.h. gDNA fragments. The terminators flanking the cloning sites of pAT6-6 are employed to block such transcription.

The vector preparation pAT66/HSC was used to generate a library of genomic DNA from the bacterium *Lactobacillus helvelicus* (L.h. gDNA). The genomic DNA was hydrodynamically sheared with the HydroShear device (GeneMachines, Inc.) and repaired with the DNATerminator Kit containing T4 DNA polymerase and T4 polynucleotide kinase (LUCIGEN, Madison Wis.). Agarose gel electrophoresis was used to fractionate the sheared DNA. Those fragments of 2–3 kb in length were excised from the gel and purified. Approximately 200 ng of this genomic DNA preparation was ligated to 50 ng of pAT66/HSC. An equal amount of the genomic DNA was ligated to 50 ng of a preparation of pUC19 that had been extensively treated with HincII and CIP ("pUC/HC"). One tenth of each ligation was transformed into DH10B cells, and aliquots were plated on carbenicillin plates. The results of plating are shown in Table 20.

TABLE 20

L.h. gDNA library construction in pAT66/HSC and pUC19/HC.

| Ligation reaction | Cell type | # Colonies/ ml | % Intact clones - # tested % |
| --- | --- | --- | --- |
| pAT66/HSC + L.h. gDNA + ligase | DH10B | $11.5 \times 10^7$ | 17/36 (47%) |
| pUC/HC + L.h. gDNA + ligase | DH10B | $0.5 \times 10^7$ | 27/55 (49%) |

The results presented in Table 20 indicate that the efficiency of cloning L.h. gDNA with the pAT66 vector was 23-fold greater than that with the pUC vector. To assess the integrity of the cloned DNA, plasmid DNA was isolated from transformants from each vector, and its size was analyzed by agarose gel electrophoresis. Both vectors resulted in approximately half of the clones having inserts that were significantly smaller than the size of the fragments in the ligation reactions. Therefore, this genomic DNA appeared to be unstable in both vectors.

EXAMPLE 18

Construction and Use of a Low Copy Number Cloning Vector

This Examples describes the construction and use of a low copy number derivative of pAT6-6 for use in multiplex cloning or as a single-insert vector. The origin of replication present in pAT6-6 is nearly identical to the origin of replication in pUC19, which maintains a high plasmid copy number of about 300–500 copies per cell. DNA fragments that are deleterious to the cell or that are difficult to replicate may be particularly difficult to clone or maintain in a high copy number plasmid. Such problems may be compounded by presence of more than one such fragment per vector, as in the case of multiplex cloning.

The copy number of plasmids containing the pUC origin of replication may be substantially reduced by expressing the product of the ROP (Repressor of Primer) gene of pBR322 in the host cell. Therefore, the ROP gene was inserted into the vector pAT6-6. The ROP gene was amplified from pBR322 with the primers ATR-1646R: CAT TTG GGC CCT CAT CAG AGG TTT TCA CCG TCA TCA CC (SEQ ID NO:87) and ATR-1441G: GTG ACC AAA CAG GAA AAA ACC GCC CT (SEQ ID NO:88). The resulting fragment was digested with ApaI and treated with T4 polynucleotide kinase. The primers ATR-1626F: CCT CTG ATG AGG GCC CAA ATG TAA TCA CCT GG (SEQ ID NO:89) and Amp-964R: TTA CCA ATG CTT AAT CAG TGA G (SEQ ID NO:90) were used to amplify pAT6-6. The resulting fragment was digested with ApaI and ligated to the ApaI/kinase-treated ROP fragment to create the vector pATR-G, which was transformed into DH10B cells. This vector uses a GTG initiation codon for the ROP gene. A nearly identical vector, pATR-A, differs by only one base pair, incorporating an ATG initiation codon for the ROP gene. pATR-A was created in a similar manner as pATR-G, using the PCR primer ATR-1441 A: ATG ACC AAA CAG GAA AAA ACC GCC CT (SEQ ID NO:91) in place of the primer ATR-1441G. Plasmid DNA was isolated from colonies transformed with pATR-A or pATR-G. Both of these vectors yielded approximately 15–30 fold less plasmid DNA than the parental plasmid pAT6-6.

Because of the low copy number of these plasmids, isolation of large quantities of plasmid DNA proved difficult.

Therefore, PCR was used to generate a fragment for use as a cloning vector. The primers AT5-381F: GAC GAA TTC TCT AGA TAT CGC TCA (SEQ ID NO:92) and AT5-28R: AAC GAA TTC AAG CTT GAT ATC ATT C (SEQ ID NO:93) were used to amplify a fragment from a preparation of pATR-G that had been digested with the restriction enzymes HincII and SnaBI and subsequently treated with CIP. The PCR product was purified and treated with CIP, generating a vector fragment designated ATR-G.

L.h. gDNA was hydrodynamically sheared, repaired with the DNATerminator Kit (Lucigen, Madison Wis.), and fractionated by agarose gel electrophoresis. Fragments of 2–3 kb in length were excised and purified, and 200 ng was ligated to 50 ng of the ATR-G vector fragment. One tenth of each reaction was transformed into DH10B cells, and aliquots were grown on plates containing carbenicillin.

TABLE 21

L.h. gDNA library construction in the low copy number vector ATR-G.

| Ligation reaction | Cell type | # Colonies/ml | % Intact clones |
|---|---|---|---|
| ATR-G + L.h. gDNA + ligase | DH10B | $8 \times 10^7$ | 58/60 (97%) |

The results shown in Table 21 indicate that propagation of L.h. gDNA fragments of 2–4 kb in the vector ATR-G resulted in approximately 16-fold more colonies than obtained previously with the vector pUC/HC. Further, the frequency of intact clones made with ATR-G was approximately 2-fold greater than that observed in clones made with pUC/HC (97% v. 49%). Therefore, the total number of intact clones was nearly 30-fold greater with the vector ATR-G than with pUC/HC.

EXAMPLE 19

Construction and Use of a Barnase Direct Selection Cloning Vector

This Examples describes the construction and use of a direct selection cloning system that incorporates the barnase lethal gene from *Bacillis amyloliqueifaciens* to provide selection against intact vector molecules. The barnase gene encodes an RNase, which is lethal to host bacteria that carry it. Protection from barnase can be provided by expression of barstar, an inhibitor of barnase. To create a direct selection cloning system based on selection provided by barnase, the barnase and barstar genes were amplified by PCR from *Bacillus amyloliqueifaciens* genomic DNA.

Barstar was amplified with the primers BSL: AAG CAG TGA TCA ACG GGG AAC AAA TCA GAA GTA TCA GCG ACC TC (SEQ ID NO:94) and BSR: ATC ACC TGC AGT TAT TAA GAA AGT ATG ATG GTG ATG TCG CAG CCT (SEQ ID NO:95). The primers GBSR: CGC TCC CTG CAG AGC CTG ATC ACT GCT TTT TTC ATT TAG GTG GCG GTA CTT GGG TCG ATA TC (SEQ ID NO:96) and THL: CAGGCTCTGC AGGGAGCGTTAACATT-TAAATCGTTGCTG (SEQ ID NO:97) were used to amplify a fragment of pGTH encompassing the gentamycin resistance gene and replication origin, but lacking the T7 1.2 gene. The PCR primers are designed such that the resulting Barstar and GTH fragments each contain a PstI site on one end and a BclI site on the other end. The fragments were digested with PstI and BclI and ligated to form the plasmid pGSTAR, which was transformed into MC12 cells.

pGSTAR DNA was isolated from a transformed colony. The colony was further grown and treated by standard procedures to render the cells competent for electroporation (designated "MC/GS" cells).

Barnase was amplified with the primers BNL: 5'-GCA CAG GTG ATC AAC ACG TTT GAC GGG GTG CGG ATT ATC T (SEQ ID NO:98) and BNR: 5'-ATC ACC TGC AGT TAT TAT CTG ATT TTT GTA AAG GTC TGA TAA TGG TCC GTT (SEQ ID NO:99). The primers CBNL: CGC TCC CTG CAG GTG ATC ACC TGT GCC ATT TAC GCC CCG CCC TGC CAC TCA TCG CAG TAC TG (SEQ ID NO:100) and THL were used to amplify a fragment of pCTH encompassing the chloramphenical resistance gene and replication origin, but lacking the T7 1.2 gene. The PCR primers are designed such that the resulting Barnase and CTH fragments each contain a PstI site on one end and a BclI site on the other end. The fragments were digested with PstI and BclI, ligated, and transformed into MC/GS cells. As a control, MC/GS were transformed with 200 pg of a pCTAB-based plasmid containing an uncharacterized HincII fragment of lambda DNA. Aliquots of the cells were plated on YT agarose containing cam or cam plus gent. The results are shown in Table 22.

TABLE 22

Transformation of MC/GS cells with a Barnase ligation reaction.

| Ligation reaction | Cell type | Antibiotic | # Colonies/ml |
|---|---|---|---|
| BN PCR + CTH PCR + ligase | MC/GS | cam | 0 |
| BN PCR + CTH PCR + ligase | MC/GS | cam + gent | 0 |
| pCTAB/lambdaHc | MC/GS | cam | >15,000 |
| pCTAB/lambdaHc | MC/GS | cam + gent | >15,000 |

"BN" = Barnase

The results from Table 22 show that the Barnase+CTH ligation produced no transformants capable of surviving in the MC/GS cells. The pCTAB/lambdaHc transformation confirmed that the MC/GS cells were competent for transformation. In addition, since the transformation efficiency was not decreased by the presence of gentamycin, most of the MC/GS competent cells must have retained their gentomycin resistance plasmid pGTH. Further, they were capable of expressing resistance simultaneously to both antibiotics.

To generate a plasmid encoding a secreted Barnase gene product, the barnase gene was fused to the phoA secretion signal sequence and expressed under control of the inducible lacZ promoter of pAT3. A PCR was performed to amplify the barnase gene from *Bacillus amyloliqueifaciens* genomic DNA and simultaneously attach the 3' portion of the phoA signal sequence to the 5' terminus of the gene. The primers were Pho2BN-F: CCG TTA CTG TTT ACC CCT GTG ACA AAA GCC GCA CAG GTT ATC AAC ACG TTT G (SEQ ID NO:102) and ABN-533R: TAT CTA GAG AAT TCG TCG ACT TAT CTG ATT TTT GTA AAG GTC T (SEQ ID NO:103). The PCR product is designated pho-barnase. A second PCR was performed to append the 5' portion of the phoA signal sequence to the lacZ promoter by amplifying pAT3 with the primers Pho1-R: TAA GAG TGC CAG TGC AAT AGT GCT TTG TTT CAT GGC TGT TTC CTG TGT GAA A (SEQ ID NO:104) and ABN-493F: CCT TTA CAA AAA TCA GAT AAG TCG ACG AAT TCT CTA GAT ATC GCT C (SEQ ID NO:105). This PCR product is designated AT3-pho. The primers ABN-493F and ABN-533R share 40 bases of complementarity, therefore, the AT3-pho and pho-barnase PCR products were capable of annealing to each other in a PCR to generate a fusion fragment consisting of the AT3 vector sequence containing the pho signal sequence joined to the barnase coding region. The AT3-pho and pho-barnase PCR fragments were mixed and amplified with the primers Pho1-R and Pho2BN-F to generate the fusion fragment, which was self-ligated to generate the plasmid pAPBN. The ligation reaction was transformed into MC/GS cells Transformants were plated on carbenicillin plus gentamycin to select for cells containing pAPBN in addition to the pGSTAR previously transformed into the MC/GS cells. Sequencing the plasmid DNAs showed that several of the clones contained the expected phoA signal fused to the barnase sequence (e.g. clones pAPBN-1 and -6), whereas others lacked a single base (#A150) corresponding to the 5'-terminal base of the Pho1-R primer (e.g. clones pAPBN-14 and -21). This deletion results in a frameshift within the phoA signal sequence. While the frameshift is expected to prevent expression of barnase from the initiation codon of the phoA signal, it is possible to re-initiate translation from a GTG codon at base 169.

Approximately 200 pg of plasmid DNA from various pAPBN transformants was used to transform MC12 or MC/GS cells. Because the MC/GS cells also contain the pGSTAR plasmid, these plasmid preparations contain pGSTAR and pAPBN. The transformants were plated on gent, carb, or amp+gent plates. Plating on gentamycin selects for clones containing pGSTAR, plating on carb selects for clones containing pAPBN, and plating on amp+ gent selects for clones containing both plasmids. The results are shown in Table 23. Values represent the average number of colonies obtained from the pairs of plasmids listed.

TABLE 23

Transformation of MC12 and MC/GS cells with pAPBN plasmid preparations that also contain pGSTAR.

| Plasmids | Cell type | # Colonies/ml | | |
|---|---|---|---|---|
| | | gent | carb | amp + gent |
| pAPBN-1, -6 | MC12 | 60,000 | 0 | 75 |
| pAPBN-14, -21 | MC12 | 34,000 | 100* | 90 |
| pAPBN-1, -6 | MC/GS | Lawn (>10$^7$) | 1,000,000 | 1,000,000 |
| pAPBN-4, -21 | MC/GS | Lawn (>10$^7$) | 600,000 | 280,000 |

*extrapolated from a single clone recovered from pAPBN-21.

The results shown in Table 23 indicate that all four clones tested show lethality mediated by the barnase gene. The pGSTAR plasmid appeared to transform MC12 cells readily, as illustrated by the high number of gent-resistant clones. Because all the MC/GS cells contained pGSTAR before transformation, plating on gent does not select against non-transformed cells, The MC/GS cells grew as a confluent lawn on gent plates, representing at feast 10$^7$ cells. It is not possible to determine what fraction of these cells were transformed by the added pGSTAR plasmid. Very few MC12 clones survived selection for the pAPBN plasmid, demonstrating the toxicity of the pAPBN clones. Several clones were recovered on carb or amp+gent plates; these were likely the result of transformation with both plasmids or mutations that rendered the barnase gene ineffective. The transformation efficiency of pAPBN in MC/GS was vastly greater than in MC12, demonstrating the protective effect of pGSTAR against barnase lethality. The presence of pGSTAR increased survival by at least 3000-fold for the pAPBN-14 and -21 clones (280,000 in MC/GS vs. 90 in MC12) and possibly much more for the pAPBN-1 and -6 clones (1,000,000 in MC/GS vs. 0 in MC12).

EXAMPLE 20

Construction and Use of a Low-Copy-Number Blue Screen Cloning Vector

This Examples describes the construction of a derivative of pATRG, designated pZLC, that incorporates the lacZ-α gene fragment to provide blue/white color selection to identify recombinant clones. The pZLC vector retains important features of pATRG, including low copy number, small size, and the presence of transcriptional terminators flanking the cloning site and following the ampR gene. However, a significant difference is that the T7 1.2 gene of pATRG is absent from pZLC, and it is replaced by the lacZ-α gene fragment. pZLC therefore lacks the direct selection attribute of pATRG. In addition, DNA fragments inserted into pZLC will be under the control of the lacZ transcriptional promoter.

To create pZLC, a preparation of pATRG was digested with the restriction enzyme HincII to excise the T7 1.2 gene. The lacZ-α gene was amplified from pUC19 with the primers LZL (5'-CATTAGGCACCCCAGGCTTTACACTTTATGCT, SEQ ID NO:106) and LZR (5'-TTATTAGCGCCATTCGCCATTCAGGCTGCGCAACTGT, SEQ ID NO:107). The resulting lacZ-α gene fragment was ligated to the HincII-digested pATRG vector fragment and transformed into MC12 cells. The cells were spread onto plates containing ampicillin, XGAL, and 1PTG. pZLC plasmid DNA was isolated from a blue colony and the lacZ insert confirmed by sequence analysis.

EXAMPLE 21

Construction and Use of a High-Copy-Number Blue Screen Cloning Vector

This Examples describes the construction of a derivative of pAT6-6, designated pZHC, that incorporates the lacZ-α gene fragment to provide blue/white color selection to identify recombinant clones. The pZHC vector retains important features of pAT6-6, including high copy number, small size, reduced number of feeder colonies, and the presence of transcriptional terminators flanking the cloning site and following the ampR gene. However, a significant difference is that the T7 1.2 gene of pAT6-6 is absent from pZHC, and it is replaced by the lacZ-α gene fragment. pZHC therefore lacks the direct selection attribute of pAT6-6. In addition, DNA fragments inserted into pZHC will be under the influence of the lacZ transcriptional promoter.

To create pZHC, the lacZ-α gene was amplified from pUC19 with primers LZL and LZR. The resulting lacZ-α gene fragment was ligated to an aliquot of pATH66/HSC and transformed into MC12 cells. Cells were spread onto agar plates containing ampicillin, XGAL, and IPTG. The plasmid pZLC was isolated from a blue transformant.

EXAMPLE 22

Construction and Use of a Multiplex Expression Cloning Vector

This Examples contemplates derivatives of the multiplex cloning vector preparation described in, for example, Example 14, such derivatives being designed to effect expression of the cloned genes. By positioning a transcriptional promoter adjacent to each of the cloning sites in a multiplex cloning vector preparation, expression of two exogenous genes can be induced in a single bacterial cell.

Further, positioning different inducible promoters adjacent to each cloning site would allow production of either or both proteins encoded by the two insert DNAs, their expression dependent on the which inducers were added to the cells. Various examples of the utility of simultaneously cloning and expressing two genes or two libraries of genes have been described in scientific literature. For example, a dual-expression multiplex cloning vector would be useful i) for production of dual-subunit molecules, e.g. the heavy chain and light chain of an antibody; ii) for analyzing the interaction between two known proteins e.g. a known receptor and its known ligand, particularly if the interaction would result in a predictable or measurable response; iii) for analyzing the interaction between a known protein and a library of genes suspected to encode one or more interacting proteins, e.g. a known substrate and a cDNA library suspected of encoding enzymes specific for the known substrate, particularly if the interaction would result in a predictable or measurable response; or iv) for analyzing the interaction between two libraries of genes suspected to encode interacting proteins, e.g. cDNA libraries suspected of encoding enzymes and their substrates, particularly if the interaction would result in a predictable or measurable response.

Various other examples of the utility of a Multiplex Expression Cloning Vector are contemplated. The vector components of a fixed orientation multiplex cloning vector may be configured as described below to append promoters to the vector components. Configuring the fixed orientation multiplex cloning system as an expression vector would allow, for example, the insertion of particular genes adjacent to defined vector fragments. Large scale analysis of gene expression in normal and diseased tissue has identified numerous genes whose expression varies according to the disease state (see, Genome Sequencing and Analysis Conference, San Diego, Calif., Oct. 25–28, 2001). Cloning of such genes in an multiplex expression vector would allow expression of a group of proteins, which would facilitate analysis or determination of the function of the individual proteins or the of proteins as a group.

In this example, the vector pAT4 carries an IPTG inducible lacz promoter that drives expression of the T7 1.2 gene. A dual expression multiplex cloning vector preparation is prepared in a PCR by amplifying pAT4 with the primers LacProm-R: TCC ACA CAT TAT ACG AGC CGG AAG CAT AAA GTG TAA AGC CTG GGG TGC CGT TAG CGA ATT CAA GCT TGA TAT CAT TCA G (SEQ ID NO:110) and LacHc-F: ATT ATG GAC TCG AGG GAC GTT GCC TTA CAG GAA ACA GCC ATG GTT AAC GGA CGT TTA TAT AGT GGT AAT CTG (SEQ ID NO:111). The resulting fragment is self-ligated to form the vector pATprom, which is nearly identical to pAT4, the only difference being that the HincII site immediately preceding the lac promoter in pAT4 is destroyed, and another HincII site is created just after the translation initiation codon. Hence, digestion with HincII will excise the entire coding region of the T7 1.2 gene, except for the initiating ATG codon and a GTT codon that corresponds to half the HincII site. This GTT codon may be removed by digesting the vector with StyI or NcoI prior to digesting with HincII. Following such digestion of the pATprom vector, the lac promoter will drive expression of DNAs inserted into the cloning site.

The vector pKfprom is a derivative of pKfR designed to transcribe sequences inserted into the cloning site of pKfR. The primers pAra-F: AAG AAA CCA ATT GTC CAT ATT GCA TCA G (SEQ ID NO:112) and pAra-R: AAC CAT CGT TTC ACT CCA TCC AAA (SEQ ID NO:113) are used to amplify the arabinose BAD promoter from E. coli strain K-12. The resulting fragment is cloned into the unique HapI site of pKfR. When inserted in the proper orientation, the terminus of the promoter fragment corresponding to the pAra-F primer is adjacent to the transcriptional terminator at the 3' end of the kanR gene of the pKfR fragment. As such, a restriction site recognized by the enzymes HpaI and HincII will be recreated at the junction of the 3' terminus of the promoter fragment and the replication origin region of the vector. In this orientation, the arabinose promoter will drive expression of DNA fragments inserted into the HpaI/HincII site.

Dual expression multiplex cloning can be achieved, for example, by processing pATprom and pKfRprom in a manner similar to that described for pAT6-6 and pKfR in Example 14. Briefly, pATprom is digested with HincII and StyI, and pKfR is digested with HincII and Sau96I. The vector components for multiplex cloning are purified from the T7 1.2 gene fragments or fd origin fragments by precipitation with 7% PEG8000 and 10 mM $MgCl_2$, treated with alkaline phosphatase, and purified by guanidine extraction and adsorption to diatomaceous earth. cDNAs encoding the two subunits of a gene of interest (e.g. the p40 and p70 subunits of interleukin-12) are mixed with the processed vector components, ligated, and transformed into MC12 cells. The cells are plated on agar plates containing carbenicillin and kanamycin, and they are incubated overnight at 37° C. Plasmid DNA is isolated from transformants and screened (e.g. by sequencing) to identify those clones that contain a copy of each subunit cDNA in each cloning site in the proper orientation for expression (approximately 25% of the clones are expected to be correctly assembled). Production of both recombinant IL-12 subunits is induced by growth of such clones in 1 mM IPTG and 0.02% arabinose.

EXAMPLE 23

Feeder Colony Reducing Vectors

This Example demonstrates the reduction in feeder colonies surrounding cells transformed with pATH and its derivatives relative to pUC19. Among the derivatives of pATH are the plasmids pAT3, pAT4, pAT5, pAT6-6, pATRG, pZHC, pZLC, and others. Sequence analysis of the ampR gene of pATH, pAT3, pAT6, and pZHC revealed the presence of several mutations relative to the ampR gene of pUC19. Table 24 shows the nucleotides present in pUC19 and the mutations in the corresponding positions of the ampR gene of pATH and its derivatives. The position of the mutation refers to the base number within the ampR gene, with the first base of the ampR coding sequence designated as base #1.

TABLE 24

Mutations in the AmpR genes of pATH and plasmids derived from pATH

| | | Position in AmpR gene | | | | | |
|---|---|---|---|---|---|---|---|
| Vector | Promoter | 174 | 333 | 412 | 648 | 668 | 764 |
| pUC19 | AmpR | T | T | A | C | T | T |
| pATH | CamR | A | C | A | C | T | T |
| pAT3 | CamR | n.d. | C | A | C | C | C |
| pAT66 | CamR | A | C | G | T | C | C |
| pZHC | CamR | A | C | G | T | C | C |

TABLE 24-continued

Mutations in the AmpR genes of pATH and plasmids derived from pATH

| | | Position in AmpR gene | | | | | |
|---|---|---|---|---|---|---|---|
| Vector | Promoter | 174 | 333 | 412 | 648 | 668 | 764 |
| A.a. change: | | Phe-><br>Leu | n.c. | Thr-><br>Ala | Pro-><br>Ser | n.c. | n.c. | n.d., not determined; n.c., no change

The vectors are ordered in Table 24 such that each vector was derived from the vector listed above it. There appears to be an accumulation of mutations with successive derivatives, consistent with the mutations being caused by mis-incorporation of bases during PCR. It is possible that the reduction in feeder colonies is primarily due to the camR promoter used in the pATH-derived plasmids. However, the low background of feeder colonies may also be related to the mutations that result in changes in the amino acid sequence of the AmpR gene, i.e. A174, G412, and T648.

All of the plasmids that have been derived from pATH show a reduction of approximately 50% in the number of feeder colonies that arise on ampicillin plates following extended growth of the transformants (e.g., 16 hrs of growth at 37 C. followed by further incubation at room temperature or 37 C.). In addition, the feeder colonies surrounding the pUC19 transformants grew more robustly than those that arose from the pATH-derived transformants.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, molecular biology, or related fields and are intended to be within the scope of the following claims.

We claim:

1. A composition comprising a vector component, wherein said vector component comprises:
   i) first and second free ends;
   ii) a selectable marker region,
   iii) an origin of replication
   iv) a first transcriptional terminator between said first free end and said selectable marker region,
   v) a second transcriptional terminator between said second free end and said origin of replication, and
   vi) a third transcriptional terminator between said origin of replication and said selectable marker region,
   and wherein said vector component is configured to form a circular recombinant vector when said first and second free ends are attached to an insert sequence.

2. The composition of claim 1, wherein said first transcriptional terminator is configured to terminate RNA transcripts entering said selectable marker region from said first free end.

3. The composition of claim 1, wherein said second transcriptional terminator is configured to terminate RNA transcripts entering said selectable marker region from said second free end.

4. The composition of claim 1, wherein said third transcriptional terminator is configured to terminate RNA transcripts encoding at least one selectable marker sequence in said selectable marker region.

5. The composition of claim 1, wherein said vector component comprises a first non-promoter sequence between said first free end and said selectable marker region, and a second non-promoter sequence between said second free end and said selectable marker region, wherein each of said first and second non-promoter sequences are unable to serve as an operable promoter in a bacterial host cell.

6. The composition of claim 1, wherein said first and second free ends are dephosphorylated.

7. A composition comprising a circular vector, wherein said circular vector comprises:
   a) a nucleic acid sequence comprising; i) first and second ends, ii) a selectable marker region, iii) a first transcriptional terminator between said first end and said selectable marker region, and iv) a second transcriptional terminator between said second end and said selectable marker region; and
   b) an insert sequence, wherein said insert sequence is attached to said first and second ends, and wherein said insert sequence comprises a base composition that is at least 65% A and T.

8. The composition of claim 7, wherein said insert sequence encodes a peptide that is deleterious to a host cell.

9. The composition of claim 7, wherein said insert sequence contains transcriptional promoters or regions that behave as promoters in bacteria.

10. The composition of claim 7, wherein said first transcriptional terminator is configured to terminate RNA transcripts entering said selectable marker region from said first end.

11. The composition of claim 7, wherein said second transcriptional terminator is configured to terminate RNA transcripts entering said selectable marker region from said second end.

12. The composition of claim 7, wherein said selectable marker region comprises a transcriptional terminator configured to terminate RNA transcripts encoding at least one selectable marker sequence in said selectable marker region.

13. The composition of claim 7, wherein said nucleic acid sequence comprises a first non-promoter sequence between said first end and said selectable marker region, and a second non-promoter sequence between said second end and said selectable marker region, wherein each of said first and second non-promoter sequences are unable to serve as an operable promoter in a bacterial host cell.

14. A composition comprising a vector component, wherein said vector component comprises:
   i) first and second free ends;
   ii) a selectable marker region comprising a selectable marker sequence, wherein said selectable marker sequence comprises a first promoter,
   iii) a first transcriptional terminator between said first free end and said selectable marker region;
   iv) a second transcriptional terminator between said second free end and said selectable marker region, and
   v) a third transcriptional terminator between said second free end and said selectable marker region,
   and wherein no other promoters are present in said vector component except said first promoter and said vector component is configured to form a circular recombinant vector when said first and second free ends are attached to an insert sequence.

15. The composition of claim 14, wherein said first and second free ends are dephosphorylated.

* * * * *

SEQUENCE LISTING

<160> NUMBER OF SEQ ID NOS: 128

<210> SEQ ID NO 1
<211> LENGTH: 46
<212> TYPE: DNA
<213> ORGANISM: Artificial Sequence
<220> FEATURE:
<223> OTHER INFORMATION: Synthetic

<400> SEQUENCE: 1
cactgttaac ccgggtttaa acgttgtgtc tcaaaatatc tgatgt        46

<210> SEQ ID NO 2
<211> LENGTH: 78
<212> TYPE: DNA
<213> ORGANISM: Artificial Sequence
<220> FEATURE:
<223> OTHER INFORMATION: Synthetic

<400> SEQUENCE: 2
cactgttccc gggagtcaaa agcctccggt cggaggcttt tgactttctg cttagaaaaa        60
ctcatcgagc atcaaatg        78

<210> SEQ ID NO 3
<211> LENGTH: 51
<212> TYPE: DNA
<213> ORGANISM: Artificial Sequence
<220> FEATURE:
<223> OTHER INFORMATION: Synthetic

<400> SEQUENCE: 3
tggacgttaa cccgggccta ctaggccttg atcggcacgt aagaggttcc a        51

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4

```
ttacgccccg ccctgccact ca                                          22

<210> SEQ ID NO 5
<211> LENGTH: 49
<212> TYPE: DNA
<213> ORGANISM: Artificial Sequence
<220> FEATURE:
<223> OTHER INFORMATION: Synthetic

<400> SEQUENCE: 5
ctgttaaccc gggcgcgcct gtgcgcggaa cccctatttg tttattttc             49

<210> SEQ ID NO 6
<211> LENGTH: 82
<212> TYPE: DNA
<213> ORGANISM: Artificial Sequence
<220> FEATURE:
<223> OTHER INFORMATION: Synthetic

<400> SEQUENCE: 6
tggacgtacc cgggcgcaga aaggccaccc gaaggtgagc cagtgtgatt acatttacca 60
atgcttaatc agtgaggcac ct                                          82

<210> SEQ ID NO 7
<211> LENGTH: 47
<212> TYPE: DNA
<213> ORGANISM: Artificial Sequence
<220> FEATURE:
<223> OTHER INFORMATION: Synthetic

<400> SEQUENCE: 7
ctgttaaccc gggatttaaa tcgttgctgg cgttttccca taggctc               47

<210> SEQ ID NO 8
<211> LENGTH: 36
<212> TYPE: DNA
<213> ORGANISM: Artificial Sequence
<220> FEATURE:
<223> OTHER INFORMATION: Synthetic

<400> SEQUENCE: 8
tggacgttaa cccgggtaga aaagatcaaa ggatct                           36

<210> SEQ ID NO 9
<211> LENGTH: 46
<212> TYPE: DNA
<213> ORGANISM: Artificial Sequence
<220> FEATURE:
<223> OTHER INFORMATION: Synthetic

<400> SEQUENCE: 9
cactgttaac ccgggaattg acataagcct gttcggttcg taaact                46

<210> SEQ ID NO 10
<211> LENGTH: 93
<212> TYPE: DNA
<213> ORGANISM: Artificial Sequence
<220> FEATURE:
<223> OTHER INFORMATION: Synthetic

<400> SEQUENCE: 10
gtgacaaccc gggcagatta aaacgaaagg cccagtcttt cgactgagcc tttcgtttta 60
tttgtttagg tggcggtact tgggtcgata tca                              93
```

```
<210> SEQ ID NO 11
<211> LENGTH: 44
<212> TYPE: DNA
<213> ORGANISM: Artificial Sequence
<220> FEATURE:
<223> OTHER INFORMATION: Synthetic

<400> SEQUENCE: 11
cagtgtcact ccatggccat gattacgcca agcttgcatg cctg                44

<210> SEQ ID NO 12
<211> LENGTH: 46
<212> TYPE: DNA
<213> ORGANISM: Artificial Sequence
<220> FEATURE:
<223> OTHER INFORMATION: Synthetic

<400> SEQUENCE: 12
cagtgtcact cccatggctg tttcctgtgt gaaattgtta tccgct              46

<210> SEQ ID NO 13
<211> LENGTH: 42
<212> TYPE: DNA
<213> ORGANISM: Artificial Sequence
<220> FEATURE:
<223> OTHER INFORMATION: Synthetic

<400> SEQUENCE: 13
tgtcactcca tgggacgttt atatagtggt aatctggcag ca                  42

<210> SEQ ID NO 14
<211> LENGTH: 44
<212> TYPE: DNA
<213> ORGANISM: Artificial Sequence
<220> FEATURE:
<223> OTHER INFORMATION: Synthetic

<400> SEQUENCE: 14
ctgactcgaa ttcttacttc cagtccttca actggtcata cata                44

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
cattaggcac cccaggcttt acactttatg                                30

<210> SEQ ID NO 16
<211> LENGTH: 40
<212> TYPE: DNA
<213> ORGANISM: Artificial Sequence
<220> FEATURE:
<223> OTHER INFORMATION: Synthetic

<400> SEQUENCE: 16
ttattacttc cagtccttca actggtcata catatggttc                     40

<210> SEQ ID NO 17
<211> LENGTH: 29
<212> TYPE: DNA
<213> ORGANISM: Artificial Sequence
<220> FEATURE:
<223> OTHER INFORMATION: Synthetic
```

<400> SEQUENCE: 17
ggaggtcgac gcagttgtaa acgttaata                                29

<210> SEQ ID NO 18
<211> LENGTH: 43
<212> TYPE: DNA
<213> ORGANISM: Artificial Sequence
<220> FEATURE:
<223> OTHER INFORMATION: Synthetic

<400> SEQUENCE: 18
cagactgtgc aagctttgca tttacgcccc gccctgccac tca                43

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
tcctctagag tcgacctgca ggca                                     24

<210> SEQ ID NO 20
<211> LENGTH: 26
<212> TYPE: DNA
<213> ORGANISM: Artificial Sequence
<220> FEATURE:
<223> OTHER INFORMATION: Synthetic

<400> SEQUENCE: 20
ccgggtaccg agctcgaatt ctagca                                   26

<210> SEQ ID NO 21
<211> LENGTH: 49
<212> TYPE: DNA
<213> ORGANISM: Artificial Sequence
<220> FEATURE:
<223> OTHER INFORMATION: Synthetic

<400> SEQUENCE: 21
ctctgagaat tcatctgcag ctcgccacgt tcgccggctt tccccgtca          49

<210> SEQ ID NO 22
<211> LENGTH: 53
<212> TYPE: DNA
<213> ORGANISM: Artificial Sequence
<220> FEATURE:
<223> OTHER INFORMATION: Synthetic

<400> SEQUENCE: 22
tgcacgaatt cttgctgcag ttgtaaacgt taatattttg ttaaaattcg cgt     53

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
atcttgtgca acgtgacatc agag                                     24

<210> SEQ ID NO 24

```
<211> LENGTH: 22
<212> TYPE: DNA
<213> ORGANISM: Artificial Sequence
<220> FEATURE:
<223> OTHER INFORMATION: Synthetic

<400> SEQUENCE: 24
cagaaagtca aaagcctccg ac                                              22

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
cagtactgcg atgagtggca g                                               21

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
gatttttgtg atgctcgtca gg                                              22

<210> SEQ ID NO 27
<211> LENGTH: 31
<212> TYPE: DNA
<213> ORGANISM: Artificial Sequence
<220> FEATURE:
<223> OTHER INFORMATION: Synthetic

<400> SEQUENCE: 27
tgggatcgca gtggtgagta accatgcatc a                                    31

<210> SEQ ID NO 28
<211> LENGTH: 27
<212> TYPE: DNA
<213> ORGANISM: Artificial Sequence
<220> FEATURE:
<223> OTHER INFORMATION: Synthetic

<400> SEQUENCE: 28
gggaaaacag cattccaggt attagaa                                         27

<210> SEQ ID NO 29
<211> LENGTH: 66
<212> TYPE: DNA
<213> ORGANISM: Artificial Sequence
<220> FEATURE:
<223> OTHER INFORMATION: Synthetic

<400> SEQUENCE: 29
catgcaaagc ttgcatgcct gcaggtcgac tctagaggat ccccgggtac cgagctcgaa     60
ttctag                                                                66

<210> SEQ ID NO 30
<211> LENGTH: 66
<212> TYPE: DNA
<213> ORGANISM: Artificial Sequence
<220> FEATURE:
<223> OTHER INFORMATION: Synthetic
```

<400> SEQUENCE: 30
catgctagaa ttcgagctcg gtacccgggg atcctctaga gtcgacctgc aggcatgcaa    60
gctttg    66

<210> SEQ ID NO 31
<211> LENGTH: 38
<212> TYPE: DNA
<213> ORGANISM: Artificial Sequence
<220> FEATURE:
<223> OTHER INFORMATION: Synthetic

<400> SEQUENCE: 31
accaaagatc ttattacttc cagtccttca actggtca    38

<210> SEQ ID NO 32
<211> LENGTH: 45
<212> TYPE: DNA
<213> ORGANISM: Artificial Sequence
<220> FEATURE:
<223> OTHER INFORMATION: Synthetic

<400> SEQUENCE: 32
cctgcaggga gcatttaaat cgttgctggc gtttttccat aggct    45

<210> SEQ ID NO 33
<211> LENGTH: 39
<212> TYPE: DNA
<213> ORGANISM: Artificial Sequence
<220> FEATURE:
<223> OTHER INFORMATION: Synthetic

<400> SEQUENCE: 33
ctgtcctcaa tacgtaaccg tatgcaatct tttcttgta    39

<210> SEQ ID NO 34
<211> LENGTH: 36
<212> TYPE: DNA
<213> ORGANISM: Artificial Sequence
<220> FEATURE:
<223> OTHER INFORMATION: Synthetic

<400> SEQUENCE: 34
atctggaaac ctgattgata ctagcacctt ctacca    36

<210> SEQ ID NO 35
<211> LENGTH: 32
<212> TYPE: DNA
<213> ORGANISM: Artificial Sequence
<220> FEATURE:
<223> OTHER INFORMATION: Synthetic

<400> SEQUENCE: 35
tctgagctcg gtacccggtc ctctagagtc ga    32

<210> SEQ ID NO 36
<211> LENGTH: 40
<212> TYPE: DNA
<213> ORGANISM: Artificial Sequence
<220> FEATURE:
<223> OTHER INFORMATION: Synthetic

<400> SEQUENCE: 36
tcttagcatg ggacgtttat atagtggtaa tctggcagca    40

<210> SEQ ID NO 37
<211> LENGTH: 26
<212> TYPE: DNA
<213> ORGANISM: Artificial Sequence
<220> FEATURE:
<223> OTHER INFORMATION: Synthetic

<400> SEQUENCE: 37
tatagttaac gctccctgca ggacca           26

<210> SEQ ID NO 38
<211> LENGTH: 30
<212> TYPE: DNA
<213> ORGANISM: Artificial Sequence
<220> FEATURE:
<223> OTHER INFORMATION: Synthetic

<400> SEQUENCE: 38
ggcagttaac atttaaatcg ttgctggcgt         30

<210> SEQ ID NO 39
<211> LENGTH: 28
<212> TYPE: DNA
<213> ORGANISM: Artificial Sequence
<220> FEATURE:
<223> OTHER INFORMATION: Synthetic

<400> SEQUENCE: 39
tattgggccc tgatcggcac gtaagagg           28

<210> SEQ ID NO 40
<211> LENGTH: 35
<212> TYPE: DNA
<213> ORGANISM: Artificial Sequence
<220> FEATURE:
<223> OTHER INFORMATION: Synthetic

<400> SEQUENCE: 40
tcatgggccc aaaagatcaa acgatcctct tgaga     35

<210> SEQ ID NO 41
<211> LENGTH: 1750
<212> TYPE: DNA
<213> ORGANISM: Artificial Sequence
<220> FEATURE:
<223> OTHER INFORMATION: Synthetic

<400> SEQUENCE: 41
tgatcggcac gtaagaggtt ccaactttca ccataatgaa ataagatcac taccgggcgt    60
atttttgag ttatcgagat tttcaggagc taaggaagct aaaatggaga aaaaaatcac   120
tggatatgcc accgttgata tcccaatg gcatcgtaaa gaacattttg aggcatttca    180
gtcagttgct caatgtacct ataaccagac cgttcagctg gatactacgg cctttttaaa   240
gaccgtaaag aaaaataagc acaagtttta tccggccttt attcacattc ttgcccgcct   300
gatgaatgct catccggaat tccgtatggc agtgaaagac ggtgagctgg tgatatggga   360
tagtgttcac ccttgttaca ccgttttcca tgagcaaact gaaacgtttt catcgctctg   420
gagtgaatac cacgacgatt tccggcagtt tctacacata tattcgcaag atgtggcgtg   480
ttacggtgaa aacctggcct atttccctaa agggtttatt gagaatatgt ttttcgtctc   540
agccaatccc tgggtgagtt tcaccagttt tgatttaaac gtggccaata tggacaactt   600
cttcgccccc gttttcacca tgggcaaata ttatacgcaa ggcgacaagg tgctgatgcc   660

-continued

```
gctggcgatt caggttcatc atgccgtttg tgatggcttc catgtcggca gaatgcttaa      720
tgaattacaa cagtactgcg atgagtggca gggcggggcg taaatgcaaa gcttgcatgc      780
ctgcaggtcg actctagagg accgggtacc gagctcagat cttagcatgg gacgtttata      840
tagtggtaat ctggcagcat tcaaggcagc aacaaacaag ctgttccagt tagacttagc      900
ggtcatttat gatgactggt ataatgccta caagaaaaa gattgcatac ggttacgtat       960
tgaggacaga tctggaaacc tgattgatac tagcaccttc taccaccacg acgaggacgt     1020
tctgttcaat atgtgtactg attggttgaa ccatatgtat gaccagttga aggactggaa     1080
gtaataagat ctttggtcct gcagggagcg ttaacattta aatcgttgct ggcgttttc      1140 cataggctcc gccccctga cgagcatcac aaaaatcgac gctcaagtca gaggtggcga     1200
aacccgacag gactataaag ataccaggcg tttccccctg gaagctccct cgtgcgctct     1260
cctgttccga ccctgccgct taccggatac ctgtccgcct ttctcccttc gggaagcgtg     1320
gcgctttctc atagctcacg ctgtaggtat ctcagttcgg tgtaggtcgt tcgctccaag     1380
ctgggctgtg tgcacgaacc ccccgttcag cccgaccgct gcgccttatc cggtaactat     1440
cgtcttgagt ccaacccggt aagacacgac ttatcgccac tggcagcagc cactggtaac     1500
aggattagca gagcgaggta tgtaggcggt gctacagagt tcttgaagtg gtggcctaac     1560
tacggctaca ctagaagaac agtatttggt atctgcgctc tgctgaagcc agttaccttc     1620
ggaaaaagag ttggtagctc ttgatccggc aaacaaacca ccgctggtag cggtggtttt     1680
tttgtttgca agcagcagat tacgcgcaga aaaaaggat ctcaagagga tcgtttgatc      1740
ttttgggccc                                                           1750
```

<210> SEQ ID NO 42
<211> LENGTH: 34
<212> TYPE: DNA
<213> ORGANISM: Artificial Sequence
<220> FEATURE:
<223> OTHER INFORMATION: Synthetic

<400> SEQUENCE: 42

```
tccgtaaagc actaaatcgg aaccctaaag ggag                                  34
```

<210> SEQ ID NO 43
<211> LENGTH: 38
<212> TYPE: DNA
<213> ORGANISM: Artificial Sequence
<220> FEATURE:
<223> OTHER INFORMATION: Synthetic

<400> SEQUENCE: 43

```
tcctcgaccc caaaaaactt gattagggtg atggttca                              38
```

<210> SEQ ID NO 44
<211> LENGTH: 30
<212> TYPE: DNA
<213> ORGANISM: Artificial Sequence
<220> FEATURE:
<223> OTHER INFORMATION: Synthetic

<400> SEQUENCE: 44

```
cgaaaaaccg tctatcaggg cgatggccca                                       30
```

<210> SEQ ID NO 45
<211> LENGTH: 51
<212> TYPE: DNA

<213> ORGANISM: Artificial Sequence
<220> FEATURE:
<223> OTHER INFORMATION: Synthetic

<400> SEQUENCE: 45
gatcccttty acgttggatt ccacgttctt taatagtgga ctcttgttcc a    51

<210> SEQ ID NO 46
<211> LENGTH: 32
<212> TYPE: DNA
<213> ORGANISM: Artificial Sequence
<220> FEATURE:
<223> OTHER INFORMATION: Synthetic

<400> SEQUENCE: 46
tccgaaaaac cgtctatcag ggcgatggcc ca    32

<210> SEQ ID NO 47
<211> LENGTH: 29
<212> TYPE: DNA
<213> ORGANISM: Artificial Sequence
<220> FEATURE:
<223> OTHER INFORMATION: Synthetic

<400> SEQUENCE: 47 tcccttttgac gttggagtcc acgttgttt    29

<210> SEQ ID NO 48
<211> LENGTH: 23
<212> TYPE: DNA
<213> ORGANISM: Artificial Sequence
<220> FEATURE:
<223> OTHER INFORMATION: Synthetic

<400> SEQUENCE: 48
cttttgtcat tttctgctta ctg    23

<210> SEQ ID NO 49
<211> LENGTH: 29
<212> TYPE: DNA
<213> ORGANISM: Artificial Sequence
<220> FEATURE:
<223> OTHER INFORMATION: Synthetic

<400> SEQUENCE: 49
gatccttata aatcaaaaga ataggccga    29

<210> SEQ ID NO 50
<211> LENGTH: 34
<212> TYPE: DNA
<213> ORGANISM: Artificial Sequence
<220> FEATURE:
<223> OTHER INFORMATION: Synthetic

<400> SEQUENCE: 50
tcatgttaac caggaatctg gatcctgcag cgcc    34

<210> SEQ ID NO 51
<211> LENGTH: 29
<212> TYPE: DNA
<213> ORGANISM: Artificial Sequence
<220> FEATURE:
<223> OTHER INFORMATION: Synthetic

<400> SEQUENCE: 51
tatagttaac gcagctcgcc acgttcgcc    29

<210> SEQ ID NO 52
<211> LENGTH: 36
<212> TYPE: DNA
<213> ORGANISM: Artificial Sequence
<220> FEATURE:
<223> OTHER INFORMATION: Synthetic

<400> SEQUENCE: 52
tactgtcgac gcatatctgg atcctgcagc cgatac                    36

<210> SEQ ID NO 53
<211> LENGTH: 18
<212> TYPE: DNA
<213> ORGANISM: Artificial Sequence
<220> FEATURE:
<223> OTHER INFORMATION: Synthetic

<400> SEQUENCE: 53
tttagcttcc ttagctcc                                        18

<210> SEQ ID NO 54
<211> LENGTH: 19
<212> TYPE: DNA
<213> ORGANISM: Artificial Sequence
<220> FEATURE:
<223> OTHER INFORMATION: Synthetic

<400> SEQUENCE: 54
atgcaaagct tgcatgcct                                       19

<210> SEQ ID NO 55
<211> LENGTH: 19
<212> TYPE: DNA
<213> ORGANISM: Artificial Sequence
<220> FEATURE:
<223> OTHER INFORMATION: Synthetic

<400> SEQUENCE: 55
atgagtattc aacatttcc                                       19

<210> SEQ ID NO 56
<211> LENGTH: 33
<212> TYPE: DNA
<213> ORGANISM: Artificial Sequence
<220> FEATURE:
<223> OTHER INFORMATION: Synthetic

<400> SEQUENCE: 56
atgcaagctt tgcatttacc aatgcttaat cag                       33

<210> SEQ ID NO 57
<211> LENGTH: 39
<212> TYPE: DNA
<213> ORGANISM: Artificial Sequence
<220> FEATURE:
<223> OTHER INFORMATION: Synthetic

<400> SEQUENCE: 57
atgttacgca gcagcaacga tgttacgcag cagggcagt                 39

<210> SEQ ID NO 58
<211> LENGTH: 33
<212> TYPE: DNA
<213> ORGANISM: Artificial Sequence
<220> FEATURE:

```
<223> OTHER INFORMATION: Synthetic

<400> SEQUENCE: 58
atgcaagctt tgcatttagg tggcggtact tgg                                33

<210> SEQ ID NO 59
<211> LENGTH: 19
<212> TYPE: DNA
<213> ORGANISM: Artificial Sequence
<220> FEATURE:
<223> OTHER INFORMATION: Synthetic

<400> SEQUENCE: 59
atgagccata ttcaacggg                                                19

<210> SEQ ID NO 60
<211> LENGTH: 41
<212> TYPE: DNA
<213> ORGANISM: Artificial Sequence
<220> FEATURE:
<223> OTHER INFORMATION: Synthetic

<400> SEQUENCE: 60
ctgcaggcat gcaagctttg catttagaaa aactcatcga g                       41

<210> SEQ ID NO 61
<211> LENGTH: 48
<212> TYPE: DNA
<213> ORGANISM: Artificial Sequence
<220> FEATURE:
<223> OTHER INFORMATION: Synthetic

<400> SEQUENCE: 61
ctggctcacc ttcgggtggg cctttctgcg ttgctggcgt ttttccat                48

<210> SEQ ID NO 62
<211> LENGTH: 54
<212> TYPE: DNA
<213> ORGANISM: Artificial Sequence
<220> FEATURE:
<223> OTHER INFORMATION: Synthetic

<400> SEQUENCE: 62
tgtgattaca tttggacgcc tgtgagcttg aggttaacgc tccctgcagg acca         54

<210> SEQ ID NO 63
<211> LENGTH: 54
<212> TYPE: DNA
<213> ORGANISM: Artificial Sequence
<220> FEATURE:
<223> OTHER INFORMATION: Synthetic

<400> SEQUENCE: 63
caccttcacg ggtgggcctt tcttcggtag aaaagatcaa aggatcttct tgag         54

<210> SEQ ID NO 64
<211> LENGTH: 64
<212> TYPE: DNA
<213> ORGANISM: Artificial Sequence
<220> FEATURE:
<223> OTHER INFORMATION: Synthetic

<400> SEQUENCE: 64
agccagtgag ttggttacag tccagttact ctcactggat gatcggcacg taagaggttc  60
caac                                                                64
```

<210> SEQ ID NO 65
<211> LENGTH: 29
<212> TYPE: DNA
<213> ORGANISM: Artificial Sequence
<220> FEATURE:
<223> OTHER INFORMATION: Synthetic

<400> SEQUENCE: 65
gtaatgaggg cccaaatgta atcacctgg                                         29

<210> SEQ ID NO 66
<211> LENGTH: 50
<212> TYPE: DNA
<213> ORGANISM: Artificial Sequence
<220> FEATURE:
<223> OTHER INFORMATION: Synthetic

<400> SEQUENCE: 66
cctgaatgat atcaagcttg aattcgttaa cggcacccca ggctttacac                  50

<210> SEQ ID NO 67
<211> LENGTH: 69
<212> TYPE: DNA
<213> ORGANISM: Artificial Sequence
<220> FEATURE:
<223> OTHER INFORMATION: Synthetic

<400> SEQUENCE: 67
ctgatttaaa tggtcagtat tgagcgatat ctagagaatt cgtcgactta cttccagtcc       60
ttcaactgg                                                               69

<210> SEQ ID NO 68
<211> LENGTH: 74
<212> TYPE: DNA
<213> ORGANISM: Artificial Sequence
<220> FEATURE:
<223> OTHER INFORMATION: Synthetic

<400> SEQUENCE: 68
tacctgacct ccatagcaga aagtcaaaag cctccgaccg gaggcttttg acttgatcgg       60
cacgtaagag gttc                                                         74

<210> SEQ ID NO 69
<211> LENGTH: 32
<212> TYPE: DNA
<213> ORGANISM: Artificial Sequence
<220> FEATURE:
<223> OTHER INFORMATION: Synthetic

<400> SEQUENCE: 69
catttgggcc ctcattacca atgcttaatc ag                                     32

<210> SEQ ID NO 70
<211> LENGTH: 29
<212> TYPE: DNA
<213> ORGANISM: Artificial Sequence
<220> FEATURE:
<223> OTHER INFORMATION: Synthetic

<400> SEQUENCE: 70
gtaatgaggg cccaaatgta atcacctgg                                         29

<210> SEQ ID NO 71

<211> LENGTH: 66
<212> TYPE: DNA
<213> ORGANISM: Artificial Sequence
<220> FEATURE:
<223> OTHER INFORMATION: Synthetic

<400> SEQUENCE: 71
cttgatatca ttcaggacga gcctcagact ccagtgagcg taactggact gtaatcaact    60
cactgg                                                              66

<210> SEQ ID NO 72
<211> LENGTH: 23
<212> TYPE: DNA
<213> ORGANISM: Artificial Sequence
<220> FEATURE:
<223> OTHER INFORMATION: Synthetic

<400> SEQUENCE: 72
cttgatatca ttcaggacga gcc                                           23

<210> SEQ ID NO 73
<211> LENGTH: 22
<212> TYPE: DNA
<213> ORGANISM: Artificial Sequence
<220> FEATURE:
<223> OTHER INFORMATION: Synthetic

<400> SEQUENCE: 73
tacctgacct ccatagcaga aa                                            22

<210> SEQ ID NO 74
<211> LENGTH: 22
<212> TYPE: DNA
<213> ORGANISM: Artificial Sequence
<220> FEATURE:
<223> OTHER INFORMATION: Synthetic

<400> SEQUENCE: 74
ctgatttaaa tggtcagtat tg                                            22

<210> SEQ ID NO 75
<211> LENGTH: 52
<212> TYPE: DNA
<213> ORGANISM: Artificial Sequence
<220> FEATURE:
<223> OTHER INFORMATION: Synthetic

<400> SEQUENCE: 75
tctttcgact gagcctttcg ttttatttga ttagaaaaac tcatcgagca tc            52

<210> SEQ ID NO 76
<211> LENGTH: 57
<212> TYPE: DNA
<213> ORGANISM: Artificial Sequence
<220> FEATURE:
<223> OTHER INFORMATION: Synthetic

<400> SEQUENCE: 76
ctgagccttt cgttttaatc tggaaaaacc accctggcgc tgcaggttcc agattcc       57

<210> SEQ ID NO 77
<211> LENGTH: 39
<212> TYPE: DNA
<213> ORGANISM: Artificial Sequence
<220> FEATURE:
<223> OTHER INFORMATION: Synthetic

<400> SEQUENCE: 77
aaccataaaa ttggcacccc aggctttaca ctttatgct                39

<210> SEQ ID NO 78
<211> LENGTH: 44
<212> TYPE: DNA
<213> ORGANISM: Artificial Sequence
<220> FEATURE:
<223> OTHER INFORMATION: Synthetic

<400> SEQUENCE: 78
gacccacggg gctggttact tccagtcctt caactggtca taca          44

<210> SEQ ID NO 79
<211> LENGTH: 39
<212> TYPE: DNA
<213> ORGANISM: Artificial Sequence
<220> FEATURE:
<223> OTHER INFORMATION: Synthetic

<400> SEQUENCE: 79
aacccacggg gatgggcagc tcgccacgtt cgccggctt                39

<210> SEQ ID NO 80
<211> LENGTH: 38
<212> TYPE: DNA
<213> ORGANISM: Artificial Sequence
<220> FEATURE:
<223> OTHER INFORMATION: Synthetic

<400> SEQUENCE: 80
gaccataaaa ctgggcagtt gtaaacgtta atattttg                 38

<210> SEQ ID NO 81
<211> LENGTH: 32
<212> TYPE: DNA
<213> ORGANISM: Artificial Sequence
<220> FEATURE:
<223> OTHER INFORMATION: Synthetic

<400> SEQUENCE: 81
agcggccgca gacttgcctg accattgacc cc                       32

<210> SEQ ID NO 82
<211> LENGTH: 28
<212> TYPE: DNA
<213> ORGANISM: Artificial Sequence
<220> FEATURE:
<223> OTHER INFORMATION: Synthetic

<400> SEQUENCE: 82
tcaatggtca ggcaagtctg cggccgct                            28

<210> SEQ ID NO 83
<211> LENGTH: 32
<212> TYPE: DNA
<213> ORGANISM: Artificial Sequence
<220> FEATURE:
<223> OTHER INFORMATION: Synthetic

<400> SEQUENCE: 83
agcggccgca gacttgcctg accattgatt tt                       32

<210> SEQ ID NO 84

```
<211> LENGTH: 32
<212> TYPE: DNA
<213> ORGANISM: Artificial Sequence
<220> FEATURE:
<223> OTHER INFORMATION: Synthetic

<400> SEQUENCE: 84
agcggccgca gacttgcctg accattgacg ac                              32

<210> SEQ ID NO 85
<211> LENGTH: 1833
<212> TYPE: DNA
<213> ORGANISM: Artificial Sequence
<220> FEATURE:
<223> OTHER INFORMATION: Synthetic

<400> SEQUENCE: 85
gacgaattct ctagatatcg ctcaatactg accatttaaa tcatacctga cctccatagc    60
agaaagtcaa aagcctccga ccggaggctt ttgacttgat cggcacgtaa gaggttccaa   120 cttcaccat aatgaaataa gatcactacc gggcgtattt tttgagttat cgagattttc    180
aggagctaag gaagctaaaa tgagtattca acatttccgt gtcgccctta ttcccttttt   240
tgcggcattt tgccttcctg tttttgctca cccagaaacg ctggtgaaag taaaagatgc   300
tgaagatcag ttgggtgcac gagtgggtta catcgaactg gatctcaaca gcggtaagat   360
ccttgagagt ttacgccccg aagaacgttt tccaatgatg agcacttta aagttctgct    420 atgtggcgcg gtattatccc gtattgacgc cgggcaagag caactcggtc gccgcataca   480
ctattctcag aatgacttgg ttgagtactc accagtcaca gaaaagcatc tcacggatgg   540
catgacagta agagaattat gcagtgctgc cataaccatg agtgataaca ctgcggccaa   600
cttacttctg gcaacgatcg gaggaccgaa ggagctaacc gcttttttgc acaacatggg   660
ggatcatgta actcgccttg atcgttggga accggagctg aatgaagcca taccaaacga   720
cgagcgtgac accacgatgc ctgtagcaat ggcaacaacg ttgcgcaaac tattaactgg   780
cgaactactt actctagctt cccggcaaca attaatagac tggatggagg cggataaagt   840
tgcaggatca cttctgcgct cggcccctcc ggctggctgg tttattgctg ataaatctgg   900
agccggtgag cgtgggtctc gcggtatcat tgcagcactg gggccagatg gtaagccctc   960
ccgcatcgta gttatctaca cgacggggag tcaggcaact atggatgaac gaaatagaca  1020
gatcgctgag ataggtgcct cactgattaa gcattggtaa tgagggccca aatgtaatca  1080
cctggctcac cttcgggtgg gcctttctgc gttgctggcg ttttttccata ggctccgccc  1140 ccctgacgag catcacaaaa atcgatgctc aagtcagagg tggcgaaacc cgacaggact  1200
ataaagatac caggcgtttc cccctggaag ctccctcgtg cgctctcctg ttccgaccct  1260
gccgcttacc ggatacctgt ccgcctttct cccttcggga agcgtggcgc tttctcatag  1320
ctcacgctgt aggtatctca gttcggtgta ggtcgttcgc tccaagctgg gctgtgtgca  1380 cgaaccccc gttcagcccg accgctgcgc cttatccggt aactatcgtc ttgagtccaa  1440
cccggtaaga cacgacttat cgccactggc agcagccact ggtaacagga ttagcagagc  1500
gaggtatgta ggcggtgcta cagagttctt gaagtggtgg cctaactacg gctacactag  1560
aagaacagta tttggtatct gcgctctgct gaagccagtt accttcggaaa aagagttggt  1620 agctcttgat ccggcaaaca aaccaccgct ggtagcggtg gttttttttgt ttgcaagcag  1680 cagattacgc gcagaaaaaa aggatctcaa gaagatcctt tgattttcta ccgaagaaag  1740
gcccacccgt gaaggtgagc cagtgagttg attgcagtcc agttacgctg gagtctgagg  1800
```
ctcgtcctga atgatatcaa gcttgaattc gtt 1833

<210> SEQ ID NO 86
<211> LENGTH: 1058
<212> TYPE: DNA
<213> ORGANISM: Artificial Sequence
<220> FEATURE:
<223> OTHER INFORMATION: Synthetic

<400> SEQUENCE: 86

| | | | | | |
|---|---|---|---|---|---|
| gacgcatatc | tggatcctgc | agccgatacg | gtcgtcgtcc | gtttaaacgt | tgtgtctcaa | 60 |
| aatctctgat | gtcacgttgc | acaagataaa | aatatatcat | catgaacaat | aaaaccgtct | 120 |
| gcttacataa | acagtaatac | aagggtgtt | atgagccata | ttcaacggga | aacgtcttgc | 180 |
| tcgaggccgc | gattaaattc | caacatggat | gctgatttat | atgggtataa | atgggctcgc | 240 |
| gataatgtcg | ggcaatcagg | tgcgacaatc | tatcgattgt | atgggaagcc | cgatgcgcca | 300 |
| gagttgtttc | tgaaacatgg | caaggtagc | gttgccaatg | atgttacaga | tgagatggtc | 360 |
| aggctaaact | ggctgacgga | atttatgcct | cttccgacca | tcaagcattt | tatccgtact | 420 |
| cctgatgatg | catggttact | caccactgcg | atcccaggga | aaacagcatt | ccaggtatta | 480 |
| gaagaatatc | tgattcagg | tgaaaatatt | gttgatgcgc | tggcagtgtt | cctgcgccgg | 540 |
| ttgcattcga | ttcctgtttg | taattgtcct | tttaacggcg | atcgcgtatt | tcgtctcgct | 600 |
| caggcgcaat | cacgaatgaa | taacggtttg | gttggtgcga | gtgattttga | tgacgagcgt | 660 |
| aatggctggc | ctgttgaaca | agtctggaaa | gaaatgcata | agcttttgcc | attctcaccg | 720 |
| gattcagtcg | tcactcatgg | tgatttctca | cttgataacc | ttatttttga | cgaggggaaa | 780 |
| ttaataggtt | gtattgatgt | tggacgagtc | ggaatcgcag | accgatacca | ggatcttgcc | 840 |
| atcctatgga | actgcctcgg | tgagttttct | ccttcattac | agaaacggct | ttttcaaaaa | 900 |
| tatggtattg | ataatcctga | tatgaataaa | ttgcagtttc | acttgatgct | cgatgagttt | 960 |
| ttctaatcaa | ataaaacgaa | aggctcagtc | gaaagactga | gcctttcgtt | ttaatctgga | 1020 |
| aaaaccaccc | tggcgctgca | ggttccagat | tcctggtt | | | 1058 |

<210> SEQ ID NO 87
<211> LENGTH: 38
<212> TYPE: DNA
<213> ORGANISM: Artificial Sequence
<220> FEATURE:
<223> OTHER INFORMATION: Synthetic

<400> SEQUENCE: 87
catttgggcc ctcatcagag gttttcaccg tcatcacc 38

<210> SEQ ID NO 88
<211> LENGTH: 26
<212> TYPE: DNA
<213> ORGANISM: Artificial Sequence
<220> FEATURE:
<223> OTHER INFORMATION: Synthetic

<400> SEQUENCE: 88
gtgaccaaac aggaaaaaac cgccct 26

<210> SEQ ID NO 89
<211> LENGTH: 32
<212> TYPE: DNA
<213> ORGANISM: Artificial Sequence
<220> FEATURE:

<223> OTHER INFORMATION: Synthetic

<400> SEQUENCE: 89
cctctgatga gggcccaaat gtaatcacct gg                32

<210> SEQ ID NO 90
<211> LENGTH: 22
<212> TYPE: DNA
<213> ORGANISM: Artificial Sequence
<220> FEATURE:
<223> OTHER INFORMATION: Synthetic

<400> SEQUENCE: 90
ttaccaatgc ttaatcagtg ag                22

<210> SEQ ID NO 91
<211> LENGTH: 26
<212> TYPE: DNA
<213> ORGANISM: Artificial Sequence
<220> FEATURE:
<223> OTHER INFORMATION: Synthetic

<400> SEQUENCE: 91
atgaccaaac aggaaaaaac cgccct                26

<210> SEQ ID NO 92
<211> LENGTH: 24
<212> TYPE: DNA
<213> ORGANISM: Artificial Sequence
<220> FEATURE:
<223> OTHER INFORMATION: Synthetic

<400> SEQUENCE: 92
gacgaattct ctagatatcg ctca                24

<210> SEQ ID NO 93
<211> LENGTH: 25
<212> TYPE: DNA
<213> ORGANISM: Artificial Sequence
<220> FEATURE:
<223> OTHER INFORMATION: Synthetic

<400> SEQUENCE: 93
aacgaattca agcttgatat cattc                25

<210> SEQ ID NO 94
<211> LENGTH: 44
<212> TYPE: DNA
<213> ORGANISM: Artificial Sequence
<220> FEATURE:
<223> OTHER INFORMATION: Synthetic

<400> SEQUENCE: 94
aagcagtgat caacggggaa caaatcagaa gtatcagcga cctc                44

<210> SEQ ID NO 95
<211> LENGTH: 45
<212> TYPE: DNA
<213> ORGANISM: Artificial Sequence
<220> FEATURE:
<223> OTHER INFORMATION: Synthetic

<400> SEQUENCE: 95
atcacctgca gttattaaga agtatgatg gtgatgtcgc agcct                45

<210> SEQ ID NO 96
<211> LENGTH: 62
<212> TYPE: DNA
<213> ORGANISM: Artificial Sequence
<220> FEATURE:
<223> OTHER INFORMATION: Synthetic

<400> SEQUENCE: 96
cgctccctgc agagcctgat cactgctttt ttcatttagg tggcggtact tgggtcgata    60
tc                                                                  62

<210> SEQ ID NO 97
<211> LENGTH: 39
<212> TYPE: DNA
<213> ORGANISM: Artificial Sequence
<220> FEATURE:
<223> OTHER INFORMATION: Synthetic

<400> SEQUENCE: 97
caggctctgc agggagcgtt aacatttaaa tcgttgctg                           39

<210> SEQ ID NO 98
<211> LENGTH: 40
<212> TYPE: DNA
<213> ORGANISM: Artificial Sequence
<220> FEATURE:
<223> OTHER INFORMATION: Synthetic

<400> SEQUENCE: 98
gcacaggtga tcaacacgtt tgacggggtg cggattatct                          40

<210> SEQ ID NO 99
<211> LENGTH: 51
<212> TYPE: DNA
<213> ORGANISM: Artificial Sequence
<220> FEATURE:
<223> OTHER INFORMATION: Synthetic

<400> SEQUENCE: 99
atcacctgca gttattatct gatttttgta aaggtctgat aatggtccgt t             51

<210> SEQ ID NO 100
<211> LENGTH: 62
<212> TYPE: DNA
<213> ORGANISM: Artificial Sequence
<220> FEATURE:
<223> OTHER INFORMATION: Synthetic

<400> SEQUENCE: 100
cgctccctgc aggtgatcac ctgtgccatt tacgcccgc cctgccactc atcgcagtac    60
tg                                                                  62

<210> SEQ ID NO 101
<211> LENGTH: 33
<212> TYPE: DNA
<213> ORGANISM: Artificial Sequence
<220> FEATURE:
<223> OTHER INFORMATION: Synthetic

<400> SEQUENCE: 101
gagctgataa caatttcaga caggaaacag cca                                33

<210> SEQ ID NO 102
<211> LENGTH: 52
<212> TYPE: DNA

<213> ORGANISM: Artificial Sequence
<220> FEATURE:
<223> OTHER INFORMATION: Synthetic

<400> SEQUENCE: 102
ccgttactgt tacccctgt gacaaaagcc gcacaggtta tcaacacgtt tg        52

<210> SEQ ID NO 103
<211> LENGTH: 43
<212> TYPE: DNA
<213> ORGANISM: Artificial Sequence
<220> FEATURE:
<223> OTHER INFORMATION: Synthetic

<400> SEQUENCE: 103
tatctagaga attcgtcgac ttatctgatt tttgtaaagg tct                 43

<210> SEQ ID NO 104
<211> LENGTH: 52
<212> TYPE: DNA
<213> ORGANISM: Artificial Sequence
<220> FEATURE:
<223> OTHER INFORMATION: Synthetic

<400> SEQUENCE: 104
taagagtgcc agtgcaatag tgctttgttt catggctgtt cctgtgtga aa        52

<210> SEQ ID NO 105
<211> LENGTH: 46
<212> TYPE: DNA
<213> ORGANISM: Artificial Sequence
<220> FEATURE:
<223> OTHER INFORMATION: Synthetic

<400> SEQUENCE: 105
cctttacaaa aatcagataa gtcgacgaat tctctagata tcgctc              46

<210> SEQ ID NO 106
<211> LENGTH: 32
<212> TYPE: DNA
<213> ORGANISM: Artificial Sequence
<220> FEATURE:
<223> OTHER INFORMATION: Synthetic

<400> SEQUENCE: 106
cattaggcac cccaggcttt acactttatg ct                             32

<210> SEQ ID NO 107
<211> LENGTH: 37
<212> TYPE: DNA
<213> ORGANISM: Artificial Sequence
<220> FEATURE:
<223> OTHER INFORMATION: Synthetic

<400> SEQUENCE: 107
ttattagcgc cattcgccat tcaggctgcg caactgt                        37

<210> SEQ ID NO 108
<211> LENGTH: 35
<212> TYPE: DNA
<213> ORGANISM: Artificial Sequence
<220> FEATURE:
<223> OTHER INFORMATION: Synthetic

<400> SEQUENCE: 108
tcggaggctt ttgactttct gctatggagg tcagg                          35

<210> SEQ ID NO 109
<211> LENGTH: 36
<212> TYPE: DNA
<213> ORGANISM: Artificial Sequence
<220> FEATURE:
<223> OTHER INFORMATION: Synthetic

<400> SEQUENCE: 109
ataattccac acattatacg agccggaagc ataaag          36

<210> SEQ ID NO 110
<211> LENGTH: 79
<212> TYPE: DNA
<213> ORGANISM: Artificial Sequence
<220> FEATURE:
<223> OTHER INFORMATION: Synthetic

<400> SEQUENCE: 110
tccacacatt atacgagccg gaagcataaa gtgtaaagcc tggggtgccg ttagcgaatt    60
caagcttgat atcattcag                             79

<210> SEQ ID NO 111
<211> LENGTH: 72
<212> TYPE: DNA
<213> ORGANISM: Artificial Sequence
<220> FEATURE:
<223> OTHER INFORMATION: Synthetic

<400> SEQUENCE: 111
attatggact cgagggacgt tgccttacag gaaacagcca tggttaacgg acgtttatat    60
agtggtaatc tg                                    72

<210> SEQ ID NO 112
<211> LENGTH: 28
<212> TYPE: DNA
<213> ORGANISM: Artificial Sequence
<220> FEATURE:
<223> OTHER INFORMATION: Synthetic

<400> SEQUENCE: 112
aagaaaccaa ttgtccatat tgcatcag                   28

<210> SEQ ID NO 113
<211> LENGTH: 24
<212> TYPE: DNA
<213> ORGANISM: Artificial Sequence
<220> FEATURE:
<223> OTHER INFORMATION: Synthetic

<400> SEQUENCE: 113
aaccatcgtt tcactccatc caaa                       24

<210> SEQ ID NO 114
<211> LENGTH: 87
<212> TYPE: DNA
<213> ORGANISM: Artificial Sequence
<220> FEATURE:
<223> OTHER INFORMATION: Synthetic

<400> SEQUENCE: 114
atcttgtgca acgtgacatc agagattttg agacacaacg tttaaacgga cgacgaccgt    60
atcggctgca ggatccagat atgcgtc                    87

<210> SEQ ID NO 115
<211> LENGTH: 54
<212> TYPE: DNA
<213> ORGANISM: Artificial Sequence
<220> FEATURE:
<223> OTHER INFORMATION: Synthetic

<400> SEQUENCE: 115
ttcgttttaa tctggaaaaa ccaccctggc gctgcaggtt ccagattcct ggtt            54

<210> SEQ ID NO 116
<211> LENGTH: 59
<212> TYPE: DNA
<213> ORGANISM: Artificial Sequence
<220> FEATURE:
<223> OTHER INFORMATION: Synthetic

<400> SEQUENCE: 116
cagtccagtt acgctggagt ctgaggctcg tcctgaatga tatcaagctt gaattcgtt      59

<210> SEQ ID NO 117
<211> LENGTH: 66
<212> TYPE: DNA
<213> ORGANISM: Artificial Sequence
<220> FEATURE:
<223> OTHER INFORMATION: Synthetic

<400> SEQUENCE: 117
ctttctgcta tggaggtcag gtatgattta aatggtcagt attgagcgat atctagagaa     60
ttcgtc                                                                66

<210> SEQ ID NO 118
<211> LENGTH: 32
<212> TYPE: DNA
<213> ORGANISM: Artificial Sequence
<220> FEATURE:
<223> OTHER INFORMATION: Synthetic

<400> SEQUENCE: 118
ccggaggctt ttgacttgat cggcacgtaa ga                                   32

<210> SEQ ID NO 119
<211> LENGTH: 40
<212> TYPE: DNA
<213> ORGANISM: Artificial Sequence
<220> FEATURE:
<223> OTHER INFORMATION: Synthetic

<400> SEQUENCE: 119
ggactcgagg gacgttgcct tacaggaaac agccatggga                           40

<210> SEQ ID NO 120
<211> LENGTH: 47
<212> TYPE: DNA
<213> ORGANISM: Artificial Sequence
<220> FEATURE:
<223> OTHER INFORMATION: Synthetic

<400> SEQUENCE: 120
gcacctgacc tcctgtgtct tcgacgaatt ctctagatat cgctcaa                   47

<210> SEQ ID NO 121
<211> LENGTH: 51
<212> TYPE: DNA
<213> ORGANISM: Artificial Sequence

```
<220> FEATURE:
<223> OTHER INFORMATION: Synthetic

<400> SEQUENCE: 121
gcaatggtct gtcgccgtct tcaacgaatt caagcttgat atcattcagg a         51

<210> SEQ ID NO 122
<211> LENGTH: 50
<212> TYPE: DNA
<213> ORGANISM: Artificial Sequence
<220> FEATURE:
<223> OTHER INFORMATION: Synthetic

<400> SEQUENCE: 122
ggacctgcaa gtcgggagac cgacgcatat ctggatcctg cagccgatac           50

<210> SEQ ID NO 123
<211> LENGTH: 49
<212> TYPE: DNA
<213> ORGANISM: Artificial Sequence
<220> FEATURE:
<223> OTHER INFORMATION: Synthetic

<400> SEQUENCE: 123
ggaatcctgg tcctcgagac caaccaggaa tctggaacct gcagcgcca            49

<210> SEQ ID NO 124
<211> LENGTH: 43
<212> TYPE: DNA
<213> ORGANISM: Artificial Sequence
<220> FEATURE:
<223> OTHER INFORMATION: Synthetic

<400> SEQUENCE: 124
ggtacttatc aggacgagac ccattaggca ccccaggctt tac                  43

<210> SEQ ID NO 125
<211> LENGTH: 45
<212> TYPE: DNA
<213> ORGANISM: Artificial Sequence
<220> FEATURE:
<223> OTHER INFORMATION: Synthetic

<400> SEQUENCE: 125
ggtctattag aggacgagac cttagcgcca ttcgccattc aggct                45

<210> SEQ ID NO 126
<211> LENGTH: 44
<212> TYPE: DNA
<213> ORGANISM: Artificial Sequence
<220> FEATURE:
<223> OTHER INFORMATION: Synthetic

<400> SEQUENCE: 126
ggaacttcga cgaccgagac caattgacat aagcctgttc ggtt                 44

<210> SEQ ID NO 127
<211> LENGTH: 45
<212> TYPE: DNA
<213> ORGANISM: Artificial Sequence
<220> FEATURE:
<223> OTHER INFORMATION: Synthetic

<400> SEQUENCE: 127
gtgtacaatg cgaccgagac cttaggtggc ggtacttggg tcgat                45
```

```
<210> SEQ ID NO 128
<211> LENGTH: 32
<212> TYPE: DNA
<213> ORGANISM: Artificial Sequence
<220> FEATURE:
<223> OTHER INFORMATION: Synthetic

<400> SEQUENCE: 128
agcggccgca gacttgcctg accattgaag ga                                    32
```